United States Patent
Yamada et al.

(10) Patent No.: US 6,656,935 B2
(45) Date of Patent: Dec. 2, 2003

(54) AROMATIC NITROGEN-CONTAINING 6-MEMBERED CYCLIC COMPOUNDS

(75) Inventors: Koichiro Yamada, Saitama-ken (JP); Kenji Matsuki, Saitama-ken (JP); Kenji Omori, Saitama (JP); Kohei Kikkawa, Kawaguchi (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 0 days.

(21) Appl. No.: 09/925,892

(22) Filed: Aug. 10, 2001

(65) Prior Publication Data

US 2003/0032647 A1 Feb. 13, 2003

Related U.S. Application Data

(63) Continuation of application No. PCT/JP00/06258, filed on Sep. 13, 2000.

(30) Foreign Application Priority Data

Sep. 16, 1999 (JP) .......................... 11-261852
Apr. 28, 2000 (JP) .......................... 2000-130371

(51) Int. Cl.$^7$ .................... C07D 239/48; C07D 403/04; C07D 401/04; A61K 31/506; A61P 15/10
(52) U.S. Cl. ................. 514/230.5; 514/231.5; 514/252.01; 514/275; 544/323; 544/325; 544/105; 544/114; 544/238
(58) Field of Search ............... 544/323, 325, 544/105, 114, 238; 514/275, 230.5, 231.5, 252.01

(56) References Cited

U.S. PATENT DOCUMENTS

| 3,670,077 A | * | 6/1972 | Freeman et al. ............ 424/200 |
| 4,704,459 A | | 11/1987 | Todo et al. ................. 546/123 |
| 4,959,368 A | | 9/1990 | Aways et al. ............... 514/252 |
| 5,525,604 A | | 6/1996 | Lee et al. .................... 514/256 |
| 5,716,993 A | | 2/1998 | Ozaki et al. ................ 514/619 |

FOREIGN PATENT DOCUMENTS

| AU | 199955977 A1 | 5/2000 |
| EP | 0 722 936 A1 | 7/1996 |
| EP | 0 459 918 B1 | 8/1996 |
| EP | 0 995 750 A1 | 4/2000 |
| HU | 211 649 A9 | 11/1995 |
| JP | 54 081299 | 6/1979 |
| JP | 2000-72751 | 3/2000 |
| WO | WO 94/28902 | 12/1994 |
| WO | WO 98/23597 | 6/1998 |

OTHER PUBLICATIONS

Yurugi et al., Ann. Rept. Takeda Res. Lab. 28. 1–11 (1969).
Vemulapalli et al., Life Sciences, vol. 67, 23–29 (2000).
Watkins et al., The Journal of Clinical Investigation, vol. 106, 373–384 (2000).
Bortolotti et al., Gastroenterology, vol. 118, 253–257 (2000).
Mule et al., British Journal of Pharmacology, vol. 127, 514–520 (1999).
Turner et al., British Journal of Pharmacology, vol. 111, 1198–1204 (1994).
Bakre et al., Journal of Cellular Biochemistry, vol. 77, 159–167 (2000).
Bolell et al., The Journal of Urology, Supplement, vol. 155, No. 5, p. 495A739 (1996).
Terrett et al., Bioorganic & Medicinal Chemistry Letters, vol. 6, No. 15, 1819–1824 (1996).
Ballard et al., British Journal of Pharmacology, Proceedings Supplement, vol. 118, 153P (1996).
Goldstein et al., The New England Journal of Medicine, vol. 338, No. 20, 1397–1404 (1998).
Goldenberg, Clinical Therapeutics, vol. 20. No. 6. 1033–1048 (1998).
Morales et al., International Journal of Impotence Research, vol. 10, No. 2, 69–73 (1998).
Estrade et al., European Journal of Pharmacology, vol. 352, 157–163 (1998).
Todd et al., Journal of American Chemical Society, vol. 65, 350–355, 1943.

\* cited by examiner

*Primary Examiner*—Richard L. Raymond
*Assistant Examiner*—Venkataraman Balasubramanian
(74) *Attorney, Agent, or Firm*—Finnegan, Henderson, Farabow, Garrett & Dunner, L.L.P.

(57) ABSTRACT

An aromatic nitrogen-containing 6-membered cyclic compound of the formula (I):

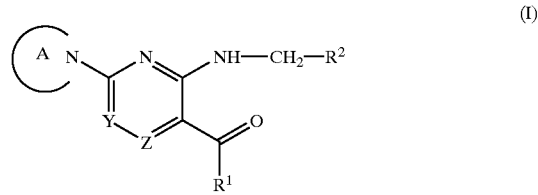

wherein Ring A is a substituted or unsubstituted nitrogen-containing heterocyclic group; $R^1$ is a substituted or unsubstituted lower alkyl group, —NH—Q—$R^3$ ($R^3$ is a substituted or unsubstituted nitrogen containing heterocyclic group, and Q is a lower alkylene group or a single bond), or —NH—$R^4$ ($R^4$ is a substituted or unsubstituted cycloalkyl group); $R^2$ is a substituted or unsubstituted aryl group; one of Y and Z is =CH—, and the other is =N—, or a pharmaceutically acceptable salt thereof, these compounds exhibiting excellent selective PDE V inhibitory activities, and hence, being useful in the prophylaxis or treatment of penile erectile dysfunction, etc.

22 Claims, No Drawings

AROMATIC NITROGEN-CONTAINING 6-MEMBERED CYCLIC COMPOUNDS

This application is a continuation application of PCT international application No. PCT/JP00/06258 which has an international filing date of Sep. 13, 2000 which designated the United States, the entire contents of which are incorporated by reference.

TECHNICAL FIELD

The present invention relates to a novel aromatic nitrogen-containing 6-membered cyclic compound exhibiting a cGMP specific phosphodiesterase (PDE) inhibitory activity (PDE V inhibitory activity) and being useful as a medicament, and a process for preparing the same.

BACKGROUND ART

In general, it is known that cGMP, which is an intracellular second messenger, is decomposed and inactivated by phosphodiesterase which widely distributes in many cell types and tissues of the living body, and when said PDE activity is inactivated, the level of cGMP in cells is increased, and as a result, various pharmacological activities, for example, relaxation of vascular smooth muscle, relaxation of bronchial smooth muscle, and inhibition of platelet aggregation are exhibited.

Moreover, it has been reported that such cGMP specific PDE inhibitors (i.e., PDE V inhibitors) are useful in the treatment of diseases caused by a functional disorder of cGMP-signaling, including hypertension, angina pectoris, myocardial infarction, chronic or acute heart failure, pulmonary hypertension, etc. (cf., PCT Patent Publication WO 96/05176, etc.), and prostatic hyperplasia (Australian Patent Publication No. 9955977). It has also been reported that PDE V inhibitors may be useful in the treatment of female sexual dysfunction (Vemulapalli et al., Life Sciences, 67, 23–29 (2000)), diabetic gastroparesis (Watkins et al., J. Clin. Invest. 106: 373–384 (2000)), achalasia (Bortolotti et al., Gastroenterology; 118: 253–257 (2000)), diarrhea (Mule et al., Br. J. Pharmacol., 127, 514–520 (1999)), constipation (Bakre et al., J. Cell. Biochem. 77: 159–167 (2000)) and asthma (Turner et al., Br. J. Pharmacol., 111, 1198–1204 (1994)).

Furthermore, it has been also reported that 1-[4-ethoxy-3-(6,7-dihydro-1-methyl-7-oxo-3-propyl-1H-pyrazolo[4,3-d]pyrimidin-5-yl)-phenylsulfonyl]-4-methylpiperazine [general name: Sildenafil] having PDE V inhibitory activity is useful in the treatment of diseases such as penile erectile dysfunction (copulative impotence), etc. (cf., Boolell et al., The Journal of Urology, Supplement, vol. 155, no. 5, p. 495A739 (1996); Terrett et al., Bioorganic & Medicinal Chemistry Letters, vol. 6, no. 15, p. 1819 (1996); and Ballard et al., British Journal of Pharmacology, Proceeding Supplement, vol. 118, p. 153 (1996)).

However, sildenafil has been reported to have side effects such as headache, facial suffusion, gut disorder, rhinitis, color sense disorder, penile erectile continuance, etc. (Irwin et al., The New England Journal of Medicine, vol. 338, no. 20, p. 1397–1404 (1998); Morales et al., International Journal of Impotence Research, vol. 10, no. 2, p. 69–73 (1998); and Goldenberg, Clinical Therapeutics, vol. 20, no. 6, p. 1033–1048 (1998)).

In addition, sildenafil has also been reported that the effects of sildenafil on light response of retina tissues and its PDE VI inhibitory activity correlate each other in the experiments on dogs (Morales et al., International Journal of Impotence Research, vol. 10, no. 2, p. 69–73 (1998)), while it has been reported that PDE VI on retina plays an importance role in the sensation of light (Morrales et al., International Journal of Impotence Research, vol. 10, no. 2, p. 69–73 (1998); Estrade et al., European Journal of Pharmacology, vol. 352, p. 157–163 (1998)).

DISCLOSURE OF INVENTION

An object of the present invention is to provide a novel aromatic nitrogen-containing 6-membered cyclic compound showing an excellent phosphodiesterase V (PDE V) inhibitory activity, and being useful as a remedy for the prophylaxis or treatment of penile erectile dysfunction with few side effects. Another object of the present invention is to provide a process for preparing such a novel aromatic nitrogen-containing 6-membered cyclic compound.

The present invention relates to an aromatic nitrogen-containing 6-membered cyclic compound of the formula (I):

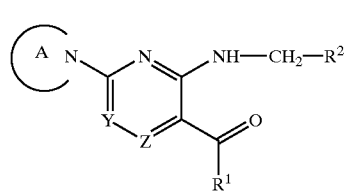

wherein Ring A is a substituted or unsubstituted nitrogen-containing heterocyclic group; $R^1$ is a substituted or unsubstituted lower alkyl group, a group of the formula: —NH—Q—$R^3$ (in which $R^3$ is a substituted or unsubstituted nitrogen-containing heterocyclic group, and Q is a lower alkylene group or a single bond), or a group of the formula: —NH—$R^4$ (in which $R^4$ is a substituted or unsubstituted cycloalkyl group); $R^2$ is a substituted or unsubstituted aryl group; one of Y and Z is a group of the formula: =CH—, and the other is a group of the formula: =N—, or a pharmaceutically acceptable salt thereof, and a process for preparing the same.

Among the compounds (I) of the present invention, the nitrogen-containing heterocyclic group of the "substituted or unsubstituted nitrogen-containing heterocyclic group" for Ring A is a 5- to 10-membered monocyclic or bicyclic nitrogen-containing heterocyclic group, more particularly, a 5- or 6-membered nitrogen-containing heteromonocyclic group and a 8- to 10-membered nitrogen-containing heterobicyclic group, and most particularly, a 5- or 6-membered non-aromatic nitrogen-containing heteromonocyclic group such as pyrrolidinyl group, piperazinyl group, piperidyl group, morpholino group, etc., a 5- or 6-membered aromatic nitrogen-containing heteromonocyclic group such as imidazolyl group, pyrrolyl group, etc., and a nitrogen-containing heterobicyclic group such as 6,7-dihydro-5H-pyrrolo[3,4-b]pyridin-6-yl group, 5,6,7,8-tetrahydroimidazo[1,2-a]pyrazin-7-yl group, 5,6,7,8-tetrahydro-1,7-naphthyridin-7-yl group, 1,2,3,4-tetrahydro-2-isoquinolinyl group, 1H-2,3,4,5,6,7-hexahydropyrazolo[4,3-c]pyridin-5-yl group, 4,5,6,7-tetrahydrothiazolo[5,4-c]-pyridin-6-yl group, 5,6,7,8-tetrahydropyrido[4,3-d]pyrimidin-6-yl group, 4,5,6,7-tetrahydro-3H-imidazo[4,5-c]pyridin-3-yl group, etc.

The nitrogen-containing heterocyclic group of the "substituted or unsubstituted nitrogen-containing heterocyclic group" for $R^3$ is a 5- or 6-membered nitrogen-containing heteromonocyclic group or a 8- to 10-membered nitrogen-containing heterobicyclic group, for example, a 5- or 6-membered non-aromatic nitrogen-containing heteromonocyclic group such as morpholinyl group, piperazinyl group, piperidyl group, thiadiazolyl group, dihydropyrimidinyl group, dihydropyrazolyl group, a 5- or 6-membered aromatic nitrogen-containing heteromonocyclic group such as pyrimidinyl group, pyridazinyl group, pyridyl group, pyrazolyl group, imidazolyl group, oxazolyl group, thiazolyl group, pyrazinyl group, and a 8- to 10-membered nitrogen-containing heterobicyclic group such as benzothiazolyl group, quinolyl group, dihydrobenzoxazolyl group, etc.

The substituent of the "substituted or unsubstituted nitrogen-containing heterocyclic group" for Ring A and $R^3$ is, for example, (1) a lower alkyl group, (2) a hydroxy-substituted lower alkyl group, (3) a formyl group, (4) an oxo group, (5) an amino group, (6) a di-(lower alkyl)amino group, (7) a hydroxy group, (8) a lower alkoxy group, (9) a lower alkoxycarbonyl group, (10) a lower alkoxy-substituted lower alkanoyl group, (11) a lower alkanoyl group, (12) a cyano-substituted lower alkyl group, and (13) a pyrimidinyl group substituted by (i) a benzylamino group substituted by a halogen atom and a lower alkoxy group and (ii) a cycloalkylcarbamoyl group substituted by a hydroxy group, etc.

The aryl group of the "substituted or unsubstituted aryl group" for $R^2$ is, for example, a 5- to 10-membered monocyclic or bicyclic aromatic hydrocarbon group such as phenyl group, naphthyl group, etc.

The substituent of the "substituted or unsubstituted aryl group" for $R^2$ is, for example, a lower alkoxy group, a halogen atom, a cyano group, a nitro group, a hydroxy group, a lower alkyl group, etc.

The substituent of the "substituted or unsubstituted lower alkyl group" for $R^1$ and the substituent of the "substituted or unsubstituted cycloalkyl group" for $R^4$ are, for example, a lower alkoxy group, a hydroxy group, a morpholinyl group, a lower alkylsulfonyl group, a di-(lower alkyl)phosphino group, a di-(lower alkyl)amino group, a pyrimidinyl-substituted lower alkylamino group, a pyridyl group, a pyridylamino group, a lower alkyl-substituted piperazinyl group, a pyrimidinyloxy group, etc.

Throughout the present description and the claims, the "lower alkyl group" means a straight chain or branched chain alkyl group having 1 to 6 carbon atoms, such as methyl, ethyl, propyl, isopropyl, butyl, isobutyl, tert-butyl, etc. The "lower alkoxy group" means a straight chain or branched chain alkoxy group having 1 to 6 carbon atoms, such as methoxy, ethoxy, propoxy, isopropyloxy, butyloxy, isobutyloxy, tert-butyloxy, etc.

The "cycloalkyl group" means a cycloalkyl having 3 to 8 carbon atoms, such as cyclopropyl, cyclobutyl, cyclopentyl, cyclohexyl, cycloheptyl, etc. The "lower alkylene group" means a straight chain or branched chain alkylene group having 1 to 6 carbon atoms, such as methylene, ethylene, trimethylene, etc.

The "halogen atom" means a fluorine atom, a chlorine atom, a bromine atom, or an iodine atom.

Among the compounds (I) of the present invention, preferable compounds are compounds of the formula (I) wherein the nitrogen-containing heterocyclic group of the "substituted or unsubstituted nitrogen-containing heterocyclic group" for Ring A is a 5- or 6-membered nitrogen-containing heteromonocyclic group or a 8- to 10-membered nitrogen-containing heterobicyclic group, and the substituent of the above "substituted or unsubstituted nitrogen-containing heterocyclic group" is selected from the group consisting of (1) a lower alkyl group, (2) a hydroxy-substituted lower alkyl group, (3) a formyl group, (4) an oxo group, (5) an amino group, (6) a hydroxy group, (7) a lower alkoxycarbonyl group, and (8) a pyrimidinyl group substituted by (i) a benzylamino group substituted by a halogen atom and a lower alkoxy group and (ii) a cycloalkylcarbamoyl group substituted by a hydroxy group, $R^1$ is a lower alkyl group which may optionally be substituted by a group selected from the group consisting of a lower alkoxy group, a hydroxy group, a morpholinyl group, a lower alkylsulfonyl group, a di-(lower alkyl)phosphino group, a di-(lower alkyl) amino group, a pyrimidinyl-substituted lower alkylamino group, a pyridyl group, a pyridylamino group, and a lower alkyl-substituted piperazinyl group, a group of the formula: —NH—Q—$R^3$, or a group of the formula: —NH—$R^4$, the nitrogen-containing heterocyclic group of the "substituted or unsubstituted nitrogen-containing heterocyclic group" for $R^3$ is a 5- or 6-membered nitrogen-containing heteromonocyclic group or a 8- to 10-membered nitrogen-containing heterobicyclic group, and the substituent of the above "substituted or unsubstituted nitrogen-containing heterocyclic group" is selected from the group consisting of a lower alkyl group, a hydroxy-substituted lower alkyl group, an oxo group, an amino group, a di-(lower alkyl)amino group, a lower alkanoyl group and a cyano-substituted lower alkyl group, $R^4$ is a cycloalkyl group being substituted by a group selected from the group consisting of hydroxy group, a lower alkoxy group and a pyrimidinyloxy group, $R^2$ is a phenyl group being substituted by a group selected from the group consisting of a lower alkoxy group, a halogen atom, a cyano group, a nitro group, a hydroxy group and a lower alkyl group.

More particularly, preferable compounds of the present invention are compounds of the formula (I), wherein the nitrogen-containing heterocyclic group of the "substituted or unsubstituted nitrogen-containing heterocyclic group" for Ring A is a 5- or 6-membered nitrogen-containing heteromonocyclic group of the formula:

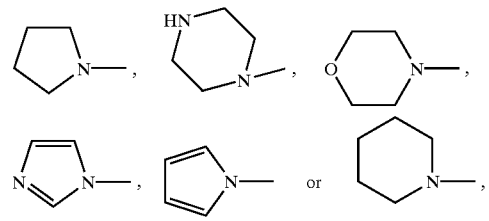

or a nitrogen-containing heterobicyclic group of the following formula wherein the above-mentioned 5- or 6-membered nitrogen-containing heteromonocyclic group and a 5- or 6-membered cyclic group are fused:

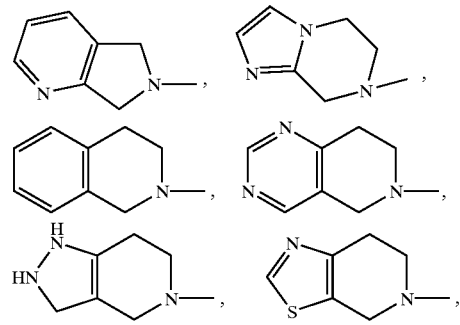

-continued

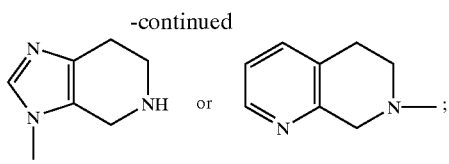

and the nitrogen-containing heterocyclic group of the "substituted or unsubstituted nitrogen-containing heterocyclic group" for $R^3$ is a non-aromatic nitrogen-containing heteromonocyclic group of the formula:

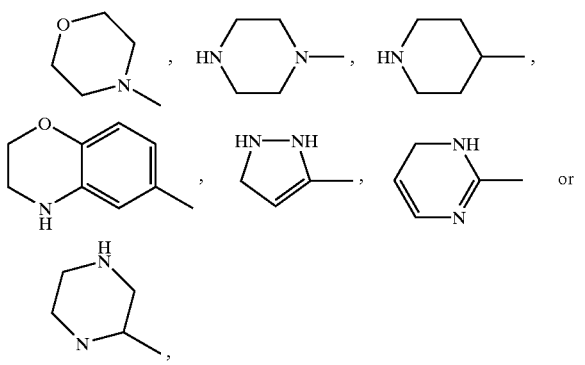

or an aromatic nitrogen-containing heterocyclic group of the formula:

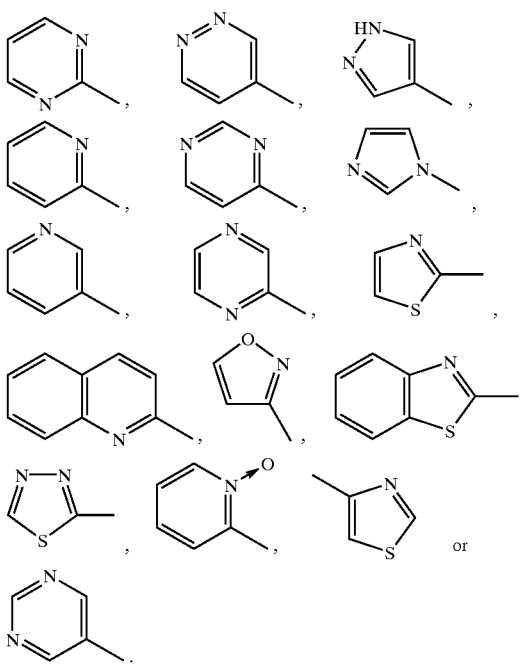

Among the compounds (I) of the present invention, other preferable compounds are compounds of the formula (I) wherein the nitrogen-containing heterocyclic group of the "substituted or unsubstituted nitrogen-containing heterocyclic group" for Ring A is a 5- or 6-membered nitrogen-containing heteromonocyclic group or a 8- to 10-membered nitrogen-containing heterobicyclic group, and the substituent of the above "substituted or unsubstituted nitrogen-containing heterocyclic group" is selected from the group consisting of a lower alkyl group, a hydroxy-substituted lower alkyl group, a formyl group and an oxo group, $R^1$ is a lower alkyl group which may optionally be substituted by a group selected from the group consisting of a lower alkoxy group and a morpholinyl group, a group of the formula: —NH—Q—$R^3$, or a group of the formula: —NH—$R^4$, the "substituted or unsubstituted nitrogen-containing heterocyclic group" for $R^3$ is a 5- or 6-membered nitrogen-containing heteromonocyclic group which may optionally be substituted by a lower alkyl group, $R^4$ is a cycloalkyl group being substituted by a group selected from the group consisting of hydroxy group and a lower alkoxy group, $R^2$ is a phenyl group being substituted by a group selected from the group consisting of a lower alkoxy group, a halogen atom and a cyano group.

More particularly, preferable compounds of the present invention are compounds of the formula (I) wherein the nitrogen-containing heterocyclic group of the "substituted or unsubstituted nitrogen-containing heterocyclic group" for Ring A is a 5- or 6-membered non-aromatic nitrogen-containing heteromonocyclic group of the formula:

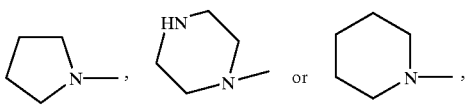

or a nitrogen-containing heterobicyclic group of the following formula wherein the above-mentioned 5- or 6-membered non-aromatic nitrogen-containing heteromonocyclic group and a 5- or 6-membered aromatic nitrogen-containing heteromonocyclic group are fused:

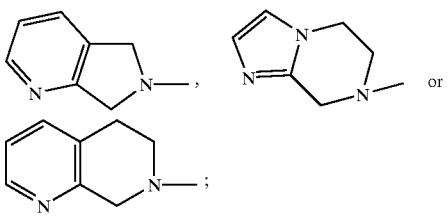

and the nitrogen-containing heterocyclic group of the "substituted or unsubstituted nitrogen-containing heterocyclic group" for $R^3$ is a non-aromatic nitrogen-containing heteromonocyclic group of the formula:

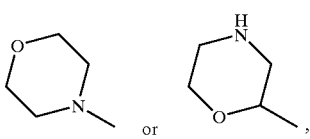

or an aromatic nitrogen-containing heteromonocyclic group of the formula:

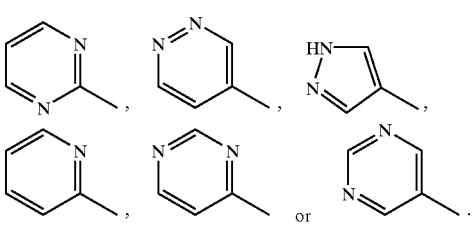

More particularly, preferable compounds of the present invention are compounds of the formula (I) wherein Ring A is a group of the formula:

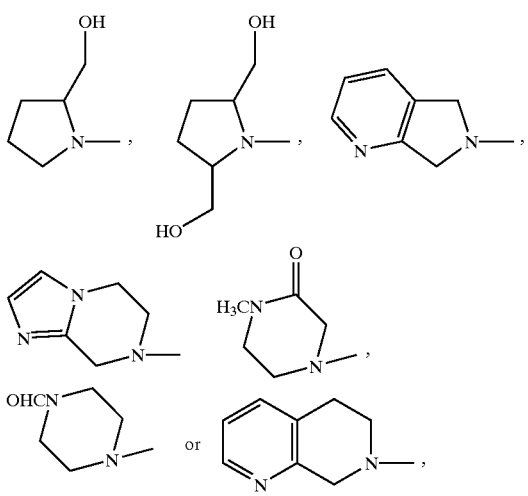

$R^1$ is a lower alkyl group, a lower alkoxy-substituted lower alkyl group, a morpholinyl-substituted lower alkyl group, a group of the formula: —NH—Q—$R^3$, or a group of the formula: —NH—$R^4$, $R^3$ is a group of the formula:

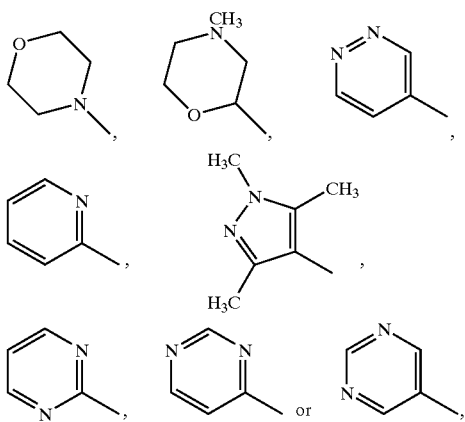

$R^4$ is a group of the formula:

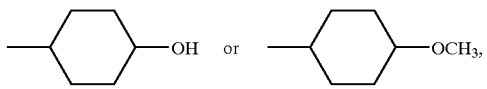

and $R^2$ is a group of the formula:

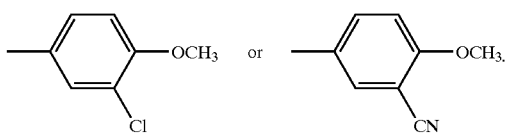

Among the compounds (I) of the present invention, more preferable compounds are compounds of the formula (I) wherein the nitrogen-containing heterocyclic group of the "substituted or unsubstituted nitrogen-containing heterocyclic group" for Ring A is a 5- or 6-membered nitrogen-containing heteromonocyclic group or a 8- to 10-membered nitrogen-containing heterobicyclic group, and the substituent of the above "substituted or unsubstituted nitrogen-containing heterocyclic group" is a group selected from the group consisting of a lower alkyl group, a hydroxy-substituted lower alkyl group, a formyl group and an oxo group, $R^1$ is a lower alkoxy-substituted lower alkyl group, a group of the formula: —NH—Q—$R^3$, or a group of the formula: —NH—$R^4$, the "substituted or unsubstituted nitrogen-containing heterocyclic group" for $R^3$ is a 5- or 6-membered nitrogen-containing heteromonocyclic group which may optionally be substituted by a lower alkyl group, $R^4$ is a hydroxy-substituted cycloalkyl group, and $R^2$ is a phenyl group being substituted by a group selected from the group consisting of a lower alkoxy group and a halogen atom.

More particularly, more preferable compounds of the present invention are compounds of the formula (I) wherein the nitrogen-containing heterocyclic group of the "substituted or unsubstituted nitrogen-containing heterocyclic group" for Ring A is a 5- or 6-membered non-aromatic nitrogen-containing heteromonocyclic group of the formula:

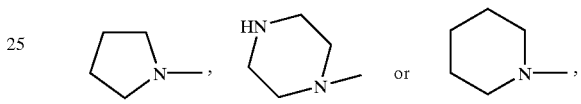

or a group of the formula:

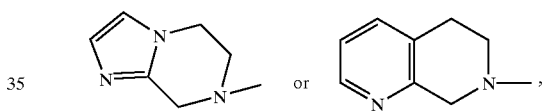

the nitrogen-containing heterocyclic group of the "substituted or unsubstituted nitrogen-containing heterocyclic group" for $R^3$ is a non-aromatic nitrogen-containing heteromonocyclic group of the formula:

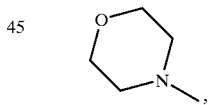

or an aromatic nitrogen-containing heteromonocyclic group of the formula:

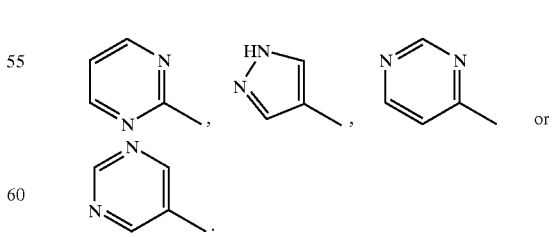

More particularly, more preferable compounds of the present compounds are compounds of the formula (I) wherein Ring A is a group of the formula:

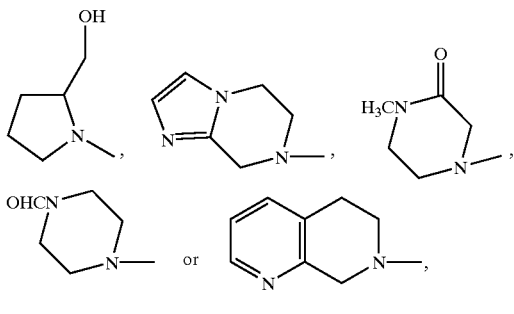

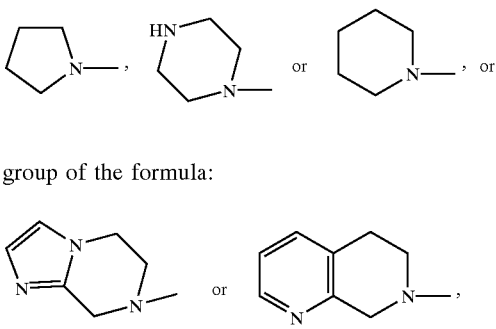

or a group of the formula:

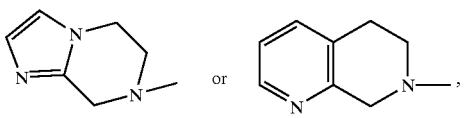

$R^1$ is a lower alkoxy-substituted lower alkyl group, a group of the formula: —NH—Q—$R^3$, or a group of the formula: —NH—$R^4$, $R^3$ is a group of the formula:

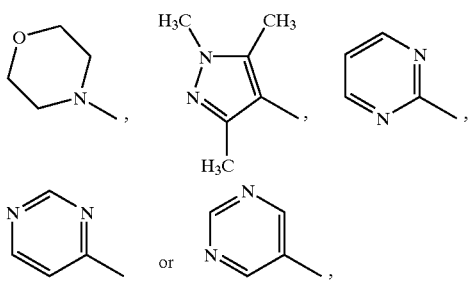

the nitrogen-containing heterocyclic group of the "substituted or unsubstituted nitrogen-containing heterocyclic group" for $R^3$ is a non-aromatic nitrogen-containing heteromonocyclic group of the formula:

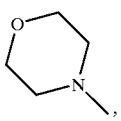

or an aromatic nitrogen-containing heteromonocyclic group of the formula:

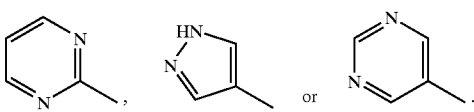

$R^1$ is a group of the formula:

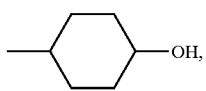

and $R^2$ is a group of the formula:

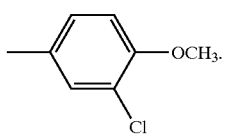

Among the compounds (I) of the present invention, further preferable compounds are compounds of the formula (I) wherein the nitrogen-containing heterocyclic group of the "substituted or unsubstituted nitrogen-containing heterocyclic group" for Ring A is a 5- or 6-membered nitrogen-containing heteromonocyclic group or a 8- to 10-membered nitrogen-containing heterobicyclic group, and the substituent of the above "substituted or unsubstituted nitrogen-containing heterocyclic group" is a hydroxy-substituted lower alkyl group, $R^1$ is a group of the formula: —NH—Q—$R^3$, the "substituted or unsubstituted nitrogen-containing heterocyclic group" for $R^1$ is a 5- or 6-membered nitrogen-containing heteromonocyclic group which may optionally be substituted by a lower alkyl group, and $R^2$ is a phenyl group being substituted by a group selected from the group consisting of a lower alkoxy group and a halogen atom.

More particularly, the more preferable compounds of the present invention are compounds of the formula (I) wherein the nitrogen-containing heterocyclic group of the "substituted or unsubstituted nitrogen-containing heterocyclic group" for Ring A is a 5- or 6-membered non-aromatic nitrogen-containing heteromonocyclic group of the formula:

More particularly, the preferable compounds of the present invention are compounds of the formula (I), wherein Ring A is a group of the formula:

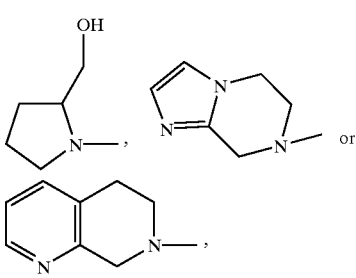

$R^1$ is a group of the formula: —NH—Q—$R^3$, $R^3$ is a group of the formula:

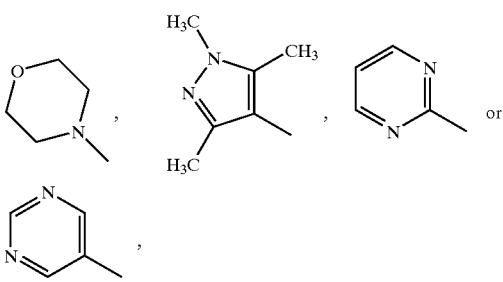

and R² is a group of the formula:

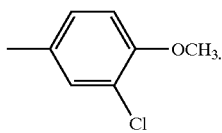

Among the compounds (I) of the present invention, the most preferable compounds are compounds of the formula (I) wherein Y is a group of the formula: =N—, and Z is a group of the formula: =CH—.

Among the compounds (I) of the present invention, pharmaceutically preferable compounds are compounds selected from the following group or a pharmaceutically acceptable salt thereof.

(S)-2-(2-hydroxymethyl-1-pyrrolidinyl)-4-(3-chloro-4-methoxybenzylamino)-5-[N-(2-pyrimidinylmethyl)carbamoyl]pyrimidine;

2-(6,7-dihydro-5H-pyrrolo[3,4-b]pyridin-6-yl)-4-(3-cyano-4-methoxybenzylamino)-5-[N-(2-pyrimidinylmethyl)carbamoyl]pyrimidine;

2-(5,6,7,8-tetrahydroimidazo[1,2-a]pyrazin-7-yl)-4-(3-chloro-4-methoxybenzylamino)-5-[N-(trans-4-methoxycyclohexyl)carbamoyl]-pyrimidine;

2-(6,7-dihydro-5H-pyrrolo[3,4-b]pyridin-6-yl)-4-(3-cyano-4-methoxybenzylamino)-5-[N-(trans-4-hydroxycyclohexyl)carbamoyl]-pyrimidine;

2-(6,7-dihydro-5H-pyrrolo[3,4-b]pyridin-6-yl)-4-(3-cyano-4-methoxybenzylamino)-5-[N-(2-morpholinoethyl)carbamoyl]pyrimidine;

(S)-2-(2-hydroxymethyl-1-pyrrolidinyl)-4-(3-chloro-4-methoxybenzylamino)-5-[N-(2-morpholinoethyl)carbamoyl]pyrimidine;

2-[(2S)-2-hydroxymethyl-1-pyrrolidinyl]-4-(3-chloro-4-methoxybenzylamino)-5-[N-[[(2R)-4-methyl-2-morpholinyl]methyl]carbamoyl]-pyrimidine;

2-[(2S)-2-hydroxymethyl-1-pyrrolidinyl]-4-(3-chloro-4-methoxybenzylamino)-5-[N-[[(2S)-4-methyl-2-morpholinyl]methyl]carbamoyl]-pyrimidine;

(S)-2-(2-hydroxymethyl-1-pyrrolidinyl)-4-(3-chloro-4-methoxybenzylamino)-5-[N-(4-pyrimidinylmethyl)carbamoyl]pyrimidine;

2-(4-methyl-3-oxo-1-piperazinyl)-4-(3-chloro-4-methoxybenzylamino)-5-[N-(trans-4-hydroxycyclohexyl)carbamoyl]pyrimidine;

2-(4-formyl-1-piperazinyl)-4-(3-chloro-4-methoxybenzylamino)-5-[N-(trans-4-hydroxycyclohexyl)carbamoyl]pyrimidine;

2-(5,6,7,8-tetrahydroimidazo[1,2-a]pyrazin-7-yl)-4-(3-chloro-4-methoxybenzylamino)-5-[N-(trans-4-hydroxycyclohexyl)carbamoyl]-pyrimidine;

2-[cis-2,5-bis(hydroxymethyl)-1-pyrrolidinyl]-4-(3-chloro-4-methoxybenzylamino)-5-[N-(2-pyrimidinylmethyl)carbamoyl]pyrimidine;

2-(5,6,7,8-tetrahydroimidazo[1,2-a]pyrazin-7-yl)-4-(3-chloro-4-methoxybenzylamino)-5-[N-(2-pyrimidinylmethyl)carbamoyl]pyrimidine;

2-(5,6,7,8-tetrahydroimidazo[1,2-a]pyrazin-7-yl)-4-(3-chloro-4-methoxybenzylamino)-5-[N-(2-morpholinoethyl)carbamoyl]pyrimidine;

2-(5,6,7,8-tetrahydro-1,7-naphthyridin-7-yl)-4-(3-chloro-4-methoxybenzylamino)-5-[N-(2-morpholinoethyl)carbamoyl]pyrimidine;

(S)-2-(2-hydroxymethyl-1-pyrrolidinyl)-4-(3-chloro-4-methoxybenzylamino)-5-acethylpyrimidine;

(S)-2-(2-hydroxymethyl-1-pyrrolidinyl)-4-(3-chloro-4-methoxybenzylamino)-5-[N-(4-pyridazinylmethyl)carbamoyl]pyrimidine;

(S)-2-(2-hydroxymethyl-1-pyrrolidinyl)-4-(3-chloro-4-methoxybenzylamino)-5-[N-(5-pyrimidinylmethyl)carbamoyl]pyrimidine;

(S)-2-(2-hydroxymethyl-1-pyrrolidinyl)-4-(3-chloro-4-methoxybenzylamino)-5-[N-(2-pyridylmethyl)carbamoyl]pyrimidine;

(S)-2-[N-(2-pyrimidinylmethyl)carbamoyl]-3-(3-chloro-4-methoxybenzylamino)-5-[2-hydroxymethyl-1-pyrrolidinyl]pyrazine;

(S)-2-(2-hydroxymethyl-1-pyrrolidinyl)-4-(3-chloro-4-methoxybenzylamino)-5-[(2-morpholinoethyl) carbonyl]pyrimidine;

2-(5,6,7,8-tetrahydroimidazo[1,2-a]pyrazin-7-yl)-4-(3-chloro-4-methoxybenzylamino)-5-[N-[(4-methyl-2-morpholinyl) methyl]-carbamoyl]pyrimidine;

(S)-2-[N-(2-morpholinoethyl)carbamoyl]-3-(3-chloro-4-methoxybenzylamino)-5-(2-hydroxymethyl-1-pyrrolidinyl)pyrazine;

2-[N-(2-pyrimidinylmethyl)carbamoyl]-3-(3-chloro-4-methoxybenzylamino)-5-(5,6,7,8-tetrahydroimidazo[1,2-a]pyrazin-7-yl)pyrazine;

(S)-2-(2-hydroxymethyl-1-pyrrolidinyl)-4-(3-chloro-4-methoxybenzylamino)-5-[(2-methoxyethyl)carbonyl]pyrimidine;

(S)-2-(2-hydroxymethyl-1-pyrrolidinyl)-4-(3-chloro-4-methoxybenzylamino)-5-[N-(1,3,5-trimethyl-4-pyrazolyl)carbamoyl]pyrimidine, or a pharmaceutically acceptable salt thereof.

Among the compounds (I) of the present invention, pharmaceutically more preferable compounds are compounds selected from the following group or a pharmaceutically acceptable salt thereof.

(S)-2-(2-hydroxymethyl-1-pyrrolidinyl)-4-(3-chloro-4-methoxybenzylamino)-5-[N-(2-pyrimidinylmethyl)carbamoyl]pyrimidine;

(S)-2-(2-hydroxymethyl-1-pyrrolidinyl)-4-(3-chloro-4-methoxybenzylamino)-5-[N-(4-pyrimidinylmethyl)carbamoyl]pyrimidine;

2-(4-methyl-3-oxo-1-piperazinyl)-4-(3-chloro-4-methoxybenzylamino)-5-[N-(trans-4-hydroxycyclohexyl)carbamoyl]pyrimidine;

2-(4-formyl-1-piperazinyl)-4-(3-chloro-4-methoxybenzylamino)-5-[N-(trans-4-hydroxycyclohexyl)carbamoyl]pyrimidine;

2-(5,6,7,8-tetrahydroimidazo[1,2-a]pyrazin-7-yl)-4-(3-chloro-4-methoxybenzylamino)-5-[N-(2-pyrimidinylmethyl)carbamoyl]pyrimidine;

2-(5,6,7,8-tetrahydroimidazo[1,2-a]pyrazin-7-yl)-4-(3-chloro-4-methoxybenzylamino)-5-[N-(2-morpholinoethyl)carbamoyl]pyrimidine;

2-(5,6,7,8-tetrahydro-1,7-naphthyridin-7-yl)-4-(3-chloro-4-methoxybenzylamino)-5-[N-(2-morpholinoethyl)carbamoyl]pyrimidine;

(S)-2-(2-hydroxymethyl-1-pyrrolidinyl)-4-(3-chloro-4-methoxybenzylamino)-5-[N-(5-pyrimidinylmethyl)carbamoyl]pyrimidine;

(S)-2-[N-(2-pyrimidinylmethyl)carbamoyl]-3-(3-chloro-4-methoxybenzylamino)-5-(2-hydroxymethyl-1-pyrrolidinyl)pyrazine;

(S)-2-(2-hydroxymethyl-1-pyrrolidinyl)-4-(3-chloro-4-methoxybenzylamino)-5-[(2-methoxyethyl)carbonyl]pyrimidine;

(S)-2-(2-hydroxymethyl-1-pyrrolidinyl)-4-(3-chloro-4-methoxybenzylamino)-5-[N-(1,3,5-trimethyl-4-pyrazolyl)carbamoyl]pyrimidine, or a pharmaceutically acceptable salt thereof.

Among the compounds (I) of the present invention, pharmaceutically preferable other compounds are compounds selected from the following group or a pharmaceutically acceptable salt thereof.

(S)-2-(2-hydroxymethyl-1-pyrrolidinyl)-4-(3-chloro-4-methoxybenzylamino)-5-[N-(2-pyrimidinylmethyl)carbamoyl]pyrimidine;

(S)-2-(2-hydroxymethyl-1-pyrrolidinyl)-4-(3-chloro-4-methoxybenzylamino)-5-[N-(2-morpholinoethyl)carbamoyl]pyrimidine;

2-(5,6,7,8-tetrahydroimidazo[1,2-a]pyrazin-7-yl)-4-(3-chloro-4-methoxybenzylamino)-5-[N-(2-pyrimidinylmethyl)carbamoyl]pyrimidine;

2-(5,6,7,8-tetrahydro-1,7-naphthyridin-7-yl)-4-(3-chloro-4-methoxybenzylamino)-5-[N-(2-morpholinoethyl)carbamoyl]pyrimidine;

(S)-2-(2-hydroxymethyl-1-pyrrolidinyl)-4-(3-chloro-4-methoxybenzylamino)-5-[N-(5-pyrimidinylmethyl)carbamoyl]pyrimidine;

(S)-2-[N-(2-pyrimidinylmethyl)carbamoyl]-3-(3-chloro-4-methoxybenzylamino)-5-(2-hydroxymethyl-1-pyrrolidinyl)pyrazine;

(S)-2-[N-(2-morpholinoethyl)carbamoyl]-3-(3-chloro-4-methoxybenzylamino)-5-(2-hydroxymethyl-1-pyrrolidinyl)pyrazine;

(S)-2-(2-hydroxymethyl-1-pyrrolidinyl)-4-(3-chloro-4-methoxybenzylamino)-5-[N-(1,3,5-trimethyl-4-pyrazolyl)carbamoyl]pyrimidine, or a pharmaceutically acceptable salt thereof.

Among the compounds (I) of the present invention, especially pharmaceutically preferable compounds are compounds selected from the following group or a pharmaceutically acceptable salt thereof.

(S)-2-(2-hydroxymethyl-1-pyrrolidinyl)-4-(3-chloro-4-methoxybenzylamino)-5-[N-(2-pyrimidinylmethyl)carbamoyl]pyrimidine, or a pharmaceutically acceptable salt thereof, 2-(5,6,7,8-tetrahydro-1,7-naphthyridin-7-yl)-4-(3-chloro-4-methoxybenzylamino)-5-[N-(2-morpholinoethyl)carbamoyl]pyrimidine, or a pharmaceutically acceptable salt thereof; and further (S)-2-(2-hydroxymethyl-1-pyrrolidinyl)-4-(3-chloro-4-methoxybenzylamino)-5-[N-(1,3,5-trimethyl-4-pyrazolyl)carbamoyl]pyrimidine, or a pharmaceutically acceptable salt thereof.

When the compound (I) of the present invention or a pharmaceutically acceptable salt thereof has an asymmetric carbon atom at Ring A, $R^1$ and/or $R^2$, it may exist in the form of an optically active isomer thereof owing to said asymmetric carbon atom thereof, and the present invention also includes these optical isomers and a mixture thereof.

The compound (I) of the present invention or a pharmaceutically acceptable salt thereof exhibits an excellent selective PDE V inhibitory activity but substantially shows few side effects such as color sense disorder, and hence, it can be used in the prophylaxis or treatment of penile erectile dysfunction.

The present compound (I) can clinically be used either in the free form or in the form of a pharmaceutically acceptable salt thereof. The pharmaceutically acceptable salt of the compound (I) includes a salt with an inorganic acid such as hydrochloride, sulfate, nitrate or hydrobromide, or a salt with an organic acid such as acetate, fumarate, oxalate, citrate, methanesulfonate, benzenesulfonate, tosylate, or maleate.

The present compound (I) or a salt thereof includes either intramolecular salt or an additive thereof, and solvates or hydrates thereof.

The present compound (I) or a pharmaceutically acceptable salt thereof can be administered either orally or parenterally, and can be formulated into a conventional pharmaceutical preparation such as tablets, granules, fine granules, pills, capsules, powders, injections, inhalants, buccal preparation, sublingual tablets, syrups, dry syrups, jellys, suppositories, ointments, elixirs, liniments, lotions, drinks, nasal drops, percutaneous preparations, and rapidly-disintegrating tablets in oral cavity, etc. These pharmaceutical preparations may be prepared by formulating with a pharmaceutically acceptable additive such as excipient, binder, wetting agent, disintegrator, thickening agent, etc., by a conventional method.

The dose of the compound (I) of the present invention or a pharmaceutically acceptable salt thereof may vary in accordance with the administration routes, and the ages, weights and conditions of the patients. For example, when administered in an injection preparation, it is usually in the range of about 0.001–100 mg/kg/day, preferably in the range of about 0.1–10 mg/kg/day. When administered in an oral preparation, it is usually in the range of about 0.1–200 mg/kg/day, preferably in the range of about 0.1–80 mg/kg/day.

Concomitantly, since the compound (I) of the present invention or a pharmaceutically acceptable salt thereof exhibits an excellent selective PDE V inhibitory activity, it also may be useful in the prophylaxis or treatment of diseases caused by a functional disorder of cGMP-signaling, such as pulmonary hypertension, diabetic gastroparesis, hypertension, angina pectoris, myocardial infarction, chronic or acute heart failure, female sexual dysfunction, prostatic hyperplasia, asthma, diarrhea, constipation and achalasia in addition to the above-mentioned erectile dysfunction.

BEST MODE FOR CARRYING OUT THE INVENTION

The compounds (I) of the present invention may be prepared by the following Processes A to F.

Process A

Among the compounds (I) of the present invention, the compound of the formula (I) wherein $R^1$ is a group of the formula: —NH—Q—$R^3$ or —NH—$R^4$, i.e., the compound of the formula (I-a):

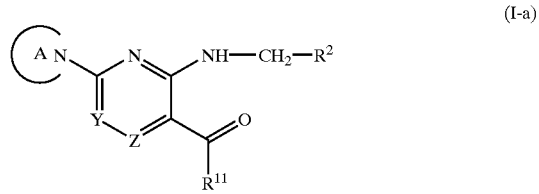

(I-a)

(wherein $R^{11}$ is a group of the formula: —NH—Q—$R^3$ or —NH—$R^4$, and the other symbols are as defined above) can be prepared by reacting a compound of the formula (II):

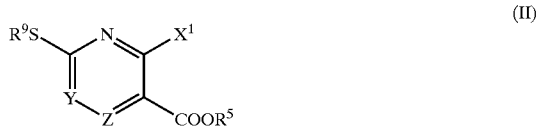

(II)

wherein $X^1$ is a halogen atom, $R^5$ is a protecting group for carboxyl group, $R^9$ is substituted or unsubstituted lower alkyl group or a substituted or unsubstituted aryl group, and the other symbols are as defined above, with a compound of the formula (III):

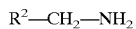
(III)

wherein the symbols are as defined above,
oxidizing the resulting compound of the formula (IV):

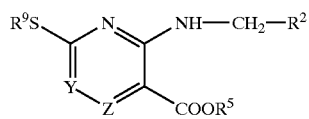
(IV)

wherein the symbols are as defined above,
to give a sulfonyl (or sulfinyl) compound of the formula (V):

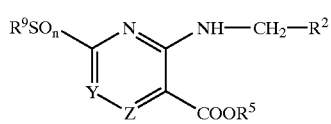
(V)

wherein n is 1 or 2, and the other symbols are as defined above,
reacting the compound (V) with a compound of the formula (VI):

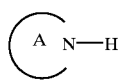
(VI)

wherein the symbol is as defined above, or a salt thereof, to give a compound of the formula (VII):

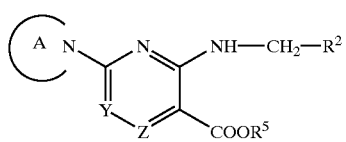
(VII)

wherein the symbols are as defined above,
removing a protecting group $R^5$ for a carboxyl group of the compound (VII) to give a compound of the formula (VIII):

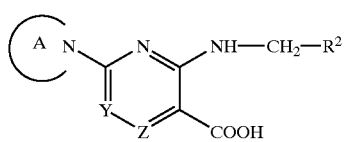
(VIII)

wherein the symbols are as defined above, and
followed by reacting the compound (VIII) with a compound of the formula (IX-a):

(IX-a)

wherein the symbols are as defined above.

The compound (I-a) can also be prepared by subjecting the compound (VIII) to halogenation to give a compound of the formula (X):

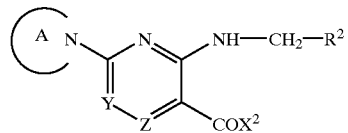
(X)

wherein $X^2$ is a halogen atom, and the other symbols are as defined above, and followed by reacting the compound (X) with the compound (IX-a).

In addition, the above compound (VII) can also be prepared by treating a dihalogeno compound of the formula (XI):

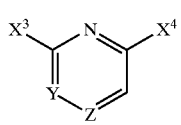
(XI)

wherein $X^3$ and $X^4$ are a halogen atom, and the other symbols are as defined above, with carbon dioxide, protecting the carboxyl group of the resulting compound of the formula (XII):

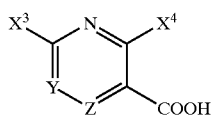
(XII)

wherein the symbols are as defined above,
to give a compound of the formula (XIII):

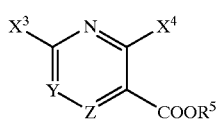
(XIII)

wherein the symbols are as defined above,
reacting the compound (XIII) with the compound (III) to give a compound of the formula (XIV):

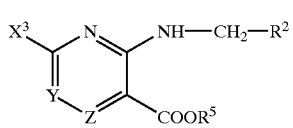
(XIV)

wherein the symbols are as defined above, and followed by reacting the compound (XIV) with the compound (VI).

Further, the above compound (XIV) can also be prepared by subjecting the compound (V) to hydrolysis, followed by halogenating the resulting compound of the formula (XV):

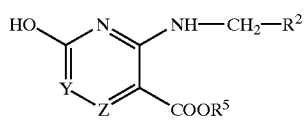

wherein the symbols are as defined above.

to Process B

Among the compounds (I) of the present invention, the compound of the formula (I) wherein $R^1$ is a substituted or unsubstituted lower alkyl group, i.e., the compound of the formula (I-b):

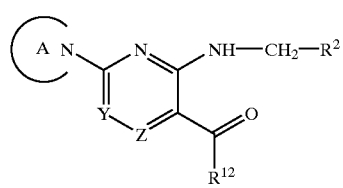

(wherein $R^{12}$ is a substituted or unsubstituted lower alkyl group, and the other symbols are as defined above) can be prepared by oxidizing a compound of the formula (XVI):

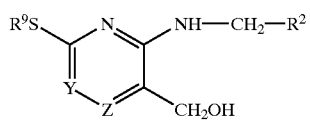

wherein the symbols are as defined above, which is obtained by reduction of the compound (IV), to give a compound of the formula (XVII):

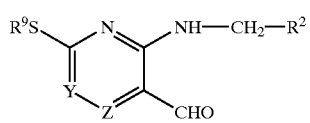

wherein the symbols are as defined above, further oxidizing the compound (XVII) to give a compound of the formula (XVIII):

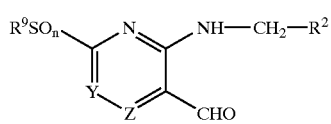

wherein the symbols are as defined above, reacting the compound (XVIII) with the compound (VI) to give a compound of the formula (XIX):

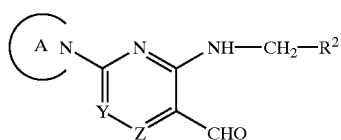

wherein the symbols are as defined above, reacting the compound (XIX) with a metal salt of a compound of the formula (IX-b):

wherein $R^{12}$ is as defined above, to give a compound of the formula (XX):

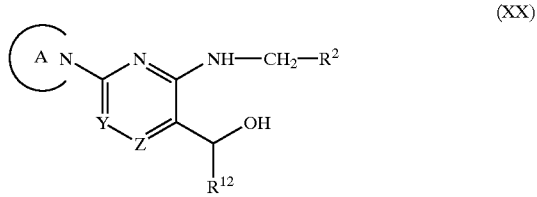

wherein the symbols are as defined above, followed by oxidizing the compound (XX).

In addition, among the compounds (I) of the present invention, the compound of the formula (I) wherein a group $R^1$ is a lower alkoxy-substituted ethyl group, a morpholino-substituted ethyl group, a 4-lower alkylpiperazinyl group-substituted ethyl group, a 3-pyridylamino-substituted ethyl group, a 2-pyridyl-lower alkylamino group-substituted ethyl group, a di-lower alkylaminoethyl group or a hydroxyethyl group, i.e., the compound of the formula (I-c):

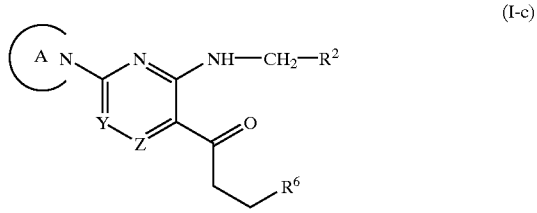

wherein $R^6$ is a lower alkoxy group, a morpholino group, a 4-lower alkylpiperazinyl group, a 3-pyridylamino group, a 2-pyrimidyl-lower alkylamino group, a di-lower alkylamino group or a hydroxy group, and the other symbols are as defined above, can be prepared by reacting the compound (XIX) with a Grignard compound of the formula:

to give a compound of the formula (XXII):

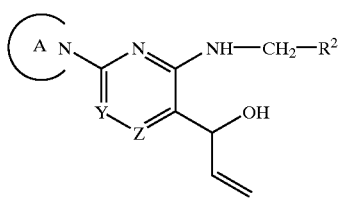
(XXII)

wherein the symbols are as defined above, oxidizing the compound (XXII) to give a compound of the formula (XXIII):

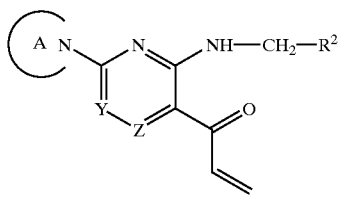
(XXIII)

wherein the symbols are as defined above, followed by reacting the compound (XXIII) with a compound of the formula (XXIV):

(XXIV)

wherein $R^6$ is as defined above.

Process C

The compound (I-a) can be prepared by reacting a compound of the formula (XXV):

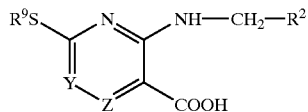
(XXV)

wherein the symbols are as defined above, which is obtained by removing the protecting group $R^5$ for a carboxyl group of the compound (IV), with the compound (IX-a) to give a compound of the formula (XXVI-a):

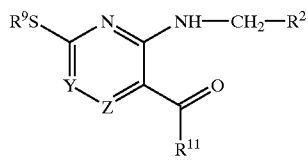
(XXVI-a)

wherein the symbols are as defined above, oxidizing the compound (XXVI-a) to give a compound of the formula (XXVII-a):

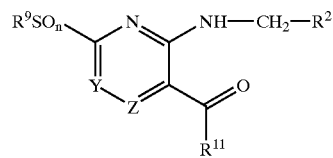
(XXVII-a)

wherein the symbols are as defined above,
followed by reacting the compound (XXVII-a) with the compound (VI).

Process D

The compound (I-b) can be prepared by oxidizing a compound of the formula (XXVIII):

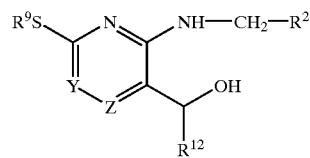
(XXVIII)

wherein the symbols are as defined above, which is obtained by reacting the compound (XVII) with a metal salt of the compound (IX-b), to give a compound of the formula (XXVI-b):

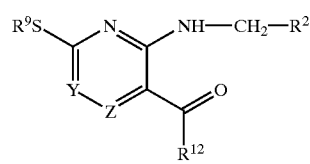
(XXVI-b)

wherein the symbols are as defined above,
further oxidizing the compound (XXVI-b) to give a compound of the formula (XXVII-b):

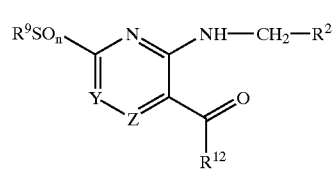
(XXVII-b)

wherein the symbols are as defined above,
followed by reacting the compound (XXVII-b) with the compound (VI).

Process E

The compound (I-b) can be prepared by oxidizing a compound of the formula (XXX):

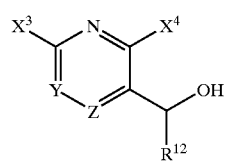
(XXX)

wherein the symbols are as defined above, which is obtained by reacting the dihalogeno compound (XI) with a compound of the formula (XXIX):

$R^{12}$—CHO (XXIX)

wherein $R^{12}$ is as defined above, to give a compound of the formula (XXXI):

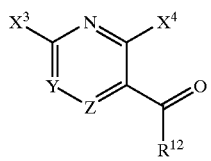

(XXXI)

wherein the symbols are as defined above,
reacting the compound (XXXI) with the compound (III) to give a compound of the formula (XXXII):

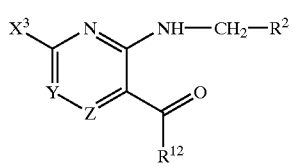

(XXXII)

wherein the symbols are as defined above,
followed by reacting the compound (XXXII) with the compound (VI).

The above compound (XXXII) can also be prepared by reacting the compound (XXX) with the compound (III) to give a compound of the formula (XXXIII):

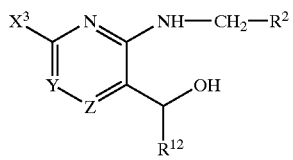

(XXXIII)

wherein the symbols are as defined above,
followed by oxidizing the compound (XXXIII).

Process F

The compound (I-a) can be prepared by
reacting the compound (XIII) with a compound of the formula (XXXIV):

RSH (XXXIV)

wherein R is a substituted or unsubstituted lower alkyl group or a substituted or unsubstituted aryl group, to give a compound of the formula (XXXV):

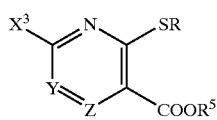

(XXXV)

wherein the symbols are as defined above,
reacting the compound (XXXV) with the compound (VI) or a salt thereof to give a compound of the formula (XXXVI):

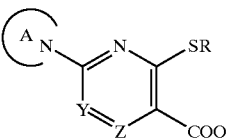

(XXXVI)

wherein the symbols are as defined above,
removing the protecting group $R^5$ for a carboxyl group of the compound (XXXVI) to give a compound of the formula (XXXVII):

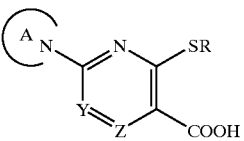

(XXXVII)

wherein the symbols are as defined above,
reacting the compound (XXXVII) with the compound (IX-a) to give a compound of the formula (XXXIX):

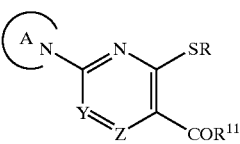

(XXXIX)

wherein the symbols are as defined above,
subjecting the compound (XXXIX) to oxidation to give a sulfonyl or sulfinyl compound,
followed by reacting the resultant with the compound (III).

The above Processes A to F can be carried out as follows.

Process A

The reaction of the compound (II) with the compound (III) is carried out in the presence or absence of an acid scavenger in a solvent. The acid scavenger includes, for example, an organic base such as N,N-diisopropylethylamine, N-methylmorpholine, triethylamine, pyridine, etc., and an inorganic base such as sodium hydride, sodium carbonate, potassium carbonate, sodium hydrogen carbonate, etc. The solvent may be any solvents which do not disturb the reaction, for example, dimethylsulfoxide, tetrahydrofuran, toluene, ethyl acetate, chloroform, dimethoxyethane, xylene, N,N-dimethylformamide, etc. The reaction is carried out at a temperature of from −10° C. to room temperature, preferably at a temperature of from 0° C. to room temperature.

The reaction of oxidizing the compound (IV) to give the sulfonyl (or sulfinyl) compound (V) is carried out in the presence of an oxidizing agent in a solvent. The oxidizing agent includes, for example, peracids such as m-chloroperbenzoic acid, peracetic acid, etc., and an inorganic oxidizing agent such as manganese dioxide, sodium periodate, hydrogen peroxide, dinitrogen tetroxide, halogen, hydroperoxide, iodobenzene acetate, t-butyl hypochlorite, sulfuryl chloride, potassium peroxymonosulfate, etc. The solvent may be any solvent which does not disturb the reaction, for example, chloroform, methylene chloride, dichloroethane, acetic acid, etc. The reaction is carried out at a temperature of from −78° C. to 50° C., preferably at a temperature of from −10° C. to 10° C.

The reaction of the compound (V) with the compound (VI) or a salt thereof can be carried out in the presence or absence of an acid scavenger in a solvent. The acid scavenger includes, for example, an organic base such as N,N-diisopropylethylamine, N-methylmorpholine, triethylamine, pyridine, etc., and an inorganic base such as sodium hydride, sodium carbonate, potassium carbonate, sodium hydrogen carbonate, etc. The salt of the compound (VI) is preferably an alkali metal salt such as sodium salt, potassium salt, etc. The solvent may be any solvent which does not disturb the reaction, for example, N,N-dimethylformamide, tetrahydrofuran, dimethoxyethane, dimethylsulfoxide, etc. The reaction is carried out at a temperature of from 0° C. to 150° C., preferably at a temperature of from room temperature to 60° C.

The reaction of removing the protecting group $R^5$ for a carboxyl group of the compound (VII) to give the compound (VIII) can be carried out by a conventional method such as hydrolysis, catalytic reduction, etc. which is selected according to the types of the protecting group for a carboxyl group to be removed. When a protecting group for a carboxyl group is removed by hydrolysis, the hydrolysis is carried out, for example, in the presence of a base in a solvent. The base is preferably, for example, an alkali metal hydroxide such as sodium hydroxide, potassium hydroxide, lithium hydroxide, etc., or an alkali metal carbonate such as sodium carbonate, potassium carbonate, etc. The solvent may be water or a mixture of water and methanol, ethanol, tetrahydrofuran, dioxane, N,N-dimethyformamide, dimethylsulfoxide, etc. The reaction is carried out at a temperature of from 0 to 80° C., preferably at a temperature of from 5° C. to 60° C. The protecting group for a carboxyl group represented by $R^5$ may be any conventional protecting group for a carboxyl group, such as a lower alkyl group, benzyl group, etc.

The reaction of the compound (VIII) with the compound (IX-a) can be carried out in the presence or absence of a condensing agent, a base or an activating agent in a suitable solvent. The condensing agent includes, for example, dicyclohexylcarbodiimide, 1-ethyl-3-(3-dimethylaminopropyl)carbodiimide, diphenylphosphoryl azide, diethylcyanophosphonate, etc., which is usually used in the peptide synthesis. The base includes, for example, an organic base such as triethylamine, N-methymorpholine, etc., and the activating agent includes, for example, 1-hydroxybenzotriazole, etc. The solvent may be any solvent which does not disturb the reaction, for example, methylene chloride, tetrahydrofuran, N,N-dimethylformamide, acetonitrile, N,N-dimethylacetamide, ethyl acetate, etc. The reaction is carried out at a temperature of from –30° C. to 50° C., preferably at a temperature of from –10° C. to 10° C.

The alternative process of converting the compound (VIII) into the compound (X), which is further reacted with the compound (IX-a) can be carried out by firstly reacting the compound (VIII) with a halogenating agent in the presence or absence of an activating agent by a conventional method, and reacting the resulting compound (X) with the compound (IX-a). The reaction of the compound (VIII) with a halogenating agent is carried out in a solvent. The halogenating agent is preferably thionyl chloride, oxalyl chloride, phosphorus pentachloride, etc. The activating agent is preferably an amide compound such as N,N-dimethylformamide, etc. The solvent may be any solvent which does not disturb the reaction, for example, methylene chloride, chloroform, tetrahydrofuran, benzene, toluene, dioxane, etc. The reaction is carried out at a temperature of from –30° C. to 100° C., preferably at a temperature of from –5° C. to 10° C.

The subsequent reaction with the compound (IX-a) is carried out in the presence of an acid scavenger in a solvent. The acid scavenger includes, for example, an organic base such as N,N-diisopropylethylamine, N-methylmorpholine, triethylamine, pyridine, dimethylaminopyridine, etc., and an inorganic base such as sodium hydride, sodium carbonate, potassium carbonate, sodium hydrogen carbonate, etc. The solvent may be any solvent which does not disturb the reaction, for example, tetrahydrofuran, methylene chloride, chloroform, toluene, benzene, dioxane, ethyl acetate, etc. The reaction is carried out at a temperature of from –30° C. to 100° C., preferably at a temperature of from –5° C. to 10° C.

The reaction of treating the dihalogeno compound (XI) with carbon dioxide to give the compound (XII) can be carried out in the presence of a base in a solvent. The base includes, for example, an alkali metal salt of an organic base such as lithium diisopropylamide, lithium 2,2,6,6-tetramethylpiperidide, etc. The solvent may be any solvent which does not disturb the reaction, for example, tetrahydrofuran, 1,2-dimethoxyethane, diethyl ether, etc. The reaction is carried out at a temperature of from –100° C. to –30° C., preferably at a temperature of from –100° C. to –70° C.

The reaction of protecting the carboxyl group of the compound (XII) to give the compound (XIII) can be carried out by a conventional method, for example, by reacting with an alkylating agent in the presence of a base in a solvent, when the protecting group is a lower alkyl group. The alkylating agent is preferably a lower alkyl halide such as methyl iodide. The base is preferably an alkali metal hydrogen carbonate such as sodium hydrogen carbonate, and the solvent may be any solvent which does not disturb the reaction, for example, N,N-dimethylformamide, tetrahydrofuran, etc. The reaction is carried out at a temperature of from 0° C. to 100° C., preferably at a temperature of from room temperature to 70° C.

The reaction of the compound (XIII) with the compound (III) to give the compound (XIV) can be carried out in the same manner as in the reaction of the compound (II) with the compound (III).

The reaction of the compound (XIV) with the compound (VI) to give the compound (VII) can be carried out in the same manner as in the reaction of the compound (V) with the compound (VI).

The hydrolysis reaction of the compound (V) to give the compound (XV) can be carried out in the presence of a base in a solvent. The base includes, for example, an alkali metal hydroxide such as sodium hydroxide, potassium hydroxide, lithium hydroxide, etc., and an alkali metal carbonate such as sodium carbonate, potassium carbonate, etc. The solvent is preferably water, or a mixture of water and methanol, ethanol, tetrahydrofuran, dioxane, N,N-dimethylformamide, dimethylsulfoxide, etc. The reaction is carried out at a temperature of from –20° C. to 80° C., preferably at a temperature of from –5° C. to 60° C.

The reaction of halogenating the compound (XV) to give the compound (XIV) can be carried out in the same manner as in the reaction of obtaining the compound (X) by halogenating the compound (XIII) by a halogenating agent.

Process B

The reduction reaction of the compound (IV) to give the compound (XVI) can be carried out in the presence of a reducing agent in a suitable solvent. The reducing agent is preferably an alkali metal aluminum hydride such as lithium aluminum hydride, and an alkali metal borohydride such as lithium borohydride, etc. The solvent may be any solvent which does not disturb the reaction, for example, tetrahydrofuran, dioxane, diethyl ether, dimethoxyethane, etc. The reaction is carried out at a temperature of from −78° C. to a boiling point of the solvent to be used, preferably at a temperature of from −10° C. to room temperature.

The oxidation reaction of the compound (XVI) to give the compound (XVII) can be carried out in the presence of an oxidizing agent in a solvent. The oxidizing agent may be any one which can convert an alcohol into a carbonyl compound, for example, manganese dioxide, barium permanganate, potassium permanganate, 2,3-dichloro-5,6-dicyano-1,4-benzoquinone, pyridinium chlorochromate, pyridinium dichromate, etc. The solvent may be any solvent which does not disturb the reaction, for example, chloroform, toluene, ethyl acetate, 1,2-dichloroethane, methylene chloride, tetrahydrofuran, etc. The reaction is carried out at a temperature of from 0° C. to 100° C., preferably at a temperature of from room temperature to 70° C.

The oxidation reaction of the compound (XVII) to give the compound (XVIII) is carried out in the same manner as in the reaction of obtaining the compound (V) by oxidizing the compound (IV).

The reaction of the compound (XVIII) with the compound (VI) to give the compound (XIX) is carried out in the same manner as in the reaction of the compound (V) with the compound (IV).

The reaction of the compound (XIX) with a metal salt of the compound (IX-b) to give the compound (XX) may be carried out in a suitable solvent. The metal salt of the compound (IX-b) is preferably lithium salt, etc. The solvent may be any solvent which does not disturb the reaction, for example, tetrahydrofuran, dioxane, diethyl ether, dimethoxyethane, etc. The reaction may preferably proceed at a temperature of from −78° C. to room temperature.

The oxidation reaction of the compound (XX) to give the compound (I-b) may be carried out in the same manner as in the reaction of obtaining (XVII) by oxidizing the compound (XVI).

The reaction of the compound (XIX) with the Grignard compound can be carried out in a suitable solvent. The solvent is preferably tetrahydrofuran, dioxane, diethyl ether, etc. The reaction may preferably proceed at a temperature of from −78° C. to 60° C., preferably at a temperature of from −78° C. to room temperature.

The oxidation reaction of the compound (XXII) to give the compound (XXIII) is carried out in the same manner as in the reaction of obtaining the compound (XVII) by oxidizing the compound (XVI).

The reaction of the compound (XXIII) with the compound (XXIV) wherein $R^6$ is a morpholino group, a 4-lower alkylpiperazinyl group, a 3-pyridylamino group, a 2-pyrimidyl-lower alkylamino group, or a di-lower alkylamino group to give the compound (I-c) wherein $R^6$ is a morpholino group, a 4-lower alkylpiperazinyl group, a 3-pyridylamino group, a 2-pyrimidinyl-lower alkylamino group, or a di-lower alkylamino group can be carried out in the presence or absence of a base in a suitable solvent. The base includes, for example, an organic base such as N,N-diisopropylethylamine, N-methylmorpholine, triethylamine, pyridine, etc., and an inorganic base such as sodium hydroxide, sodium carbonate, potassium carbonate, sodium hydrogen carbonate, etc. The solvent may preferably be ethanol, N,N-dimethylformamide, tetrahydrofuran, dimethoxyethane, dimethylsulfoxide, etc. The reaction may preferably proceed at a temperature of from 0° C. to 150° C., preferably at a temperature of from room temperature to 60° C.

On the other hand, the reaction of the compound (XXIII) with the compound (XXIV) wherein $R^6$ is a hydroxy group or a lower alkoxy group to give the compound (XXI) wherein $R^6$ is a hydroxy group or a lower alkoxy group can be carried in the presence of an acid in a solvent or without a solvent. The acid includes, for example, an inorganic acid such as sulfuric acid, etc., or an organic acid such as methanesulfonic acid, camphorsulfonic acid, toluenesulfonic acid, benzenesulfonic acid, etc. The solvent may preferably be diethyl ether, toluene, benzene, N,N-dimethylformamide, dimethoxyethane, dimethylsulfoxide, etc. The reaction may preferably proceed at a temperature of from 0° C. to 150° C., preferably at a temperature of from room temperature to 60° C.

Process C

The reaction of removing the protecting group $R^5$ for a carboxyl group of the compound (IV) to give the compound (XXV) can be carried out in the same manner as in the reaction of obtaining the compound (VIII) by removing the protecting group $R^5$ for a carboxyl group of the compound (VII).

The reaction of the compound (XXV) with the compound (IX-a) to give the compound (XXVI-a) can be carried out in the same manner as in the reaction of the compound (VIII) with the compound (IX-a).

The reaction of oxidizing the compound (XXVI-a) to give the compound (XXVII-1) can be carried out in the same manner as in the reaction of obtaining the compound (V) by oxidizing the above compound (IV).

The reaction of the compound (XXVII-a) with the compound (VI) to give the compound (I-a) of the present invention can be carried out in the same manner as in the reaction of the compound (V) with the compound (VI).

Process D

The reaction of the compound (XVII) with a metal salt of the compound (IX-b) to give the compound (XXVIII) can be carried out in the same manner as in the reaction of the compound (XIX) with a metal salt of the compound (IX-b).

The reaction of oxidizing the compound (XXVIII) to give the it compound (XXVI-b) can be carried out in the same manner as in the reaction of obtaining the compound (XVII) by oxidizing the compound (XVI).

The process wherein the compound (XXVI-b) is oxidized to give the compound (XXVII-b) which is further converted into the compound (I-b) of the present invention can be carried out in the same manner as in the process wherein the compound (XXVI-a) is oxidized to give the compound (XXVII-a) which is further converted into the compound (I-a) of the present invention.

Process E

The reaction of the compound (XI) with the compound (XXIX) to give the compound (XXX) is carried out in the presence of a base in a suitable solvent. The base includes, for example, an alkali metal salt of an organic base such as lithium diisopropylamide, lithium 2,2,6,6-tetramethylpiperidide, etc. The solvent may be any solvent which does not disturb the reaction, for example, tetrahydrofuran, 1,2-dimethoxyethane, diethyl ether, etc. The reaction is carried out at a temperature of from −100° C. to −30° C., preferably at a temperature of from −100° C. to −70° C.

The reaction of oxidizing the compound (XXX) to give the compound (XXXI) can be carried out in the same manner as in the reaction of oxidizing the compound (XVI) to give the compound (XVII).

The reaction of the compound (XXXI) with the compound (III) to give the compound (XXXII) can be carried out in the same manner as in the reaction of the compound (II) with the compound (III).

The reaction of the compound (XXXII) with the compound (VI) or a salt thereof to give the compound (I-b) of the present invention can be carried out in the same manner as in the reaction of the compound (V) with the compound (VI).

The reaction of the compound (XXX) with the compound (III) to give the compound (XXXIII) can be carried out in the same manner as in the reaction of the compound (II) with the compound (III). Besides, the reaction of oxidizing the compound (XXXIII) to give the compound (XXXII) can be carried out in the same manner as in the reaction of oxidizing the compound (XVI) to give the compound (XVII).

Process F

The reaction of the compound (XIII) with the compound (XXXIV) can be carried out in the presence or absence of an acid scavenger in a solvent. The acid scavenger includes, for example, an organic base such as N,N-diisopropylethylamine, N-methylmorpholine, triethylamine, pyridine, etc., or an inorganic base such as sodium hydride, sodium carbonate, potassium carbonate, sodium hydrogen carbonate, etc. The solvent may be any solvent which does not disturb the reaction, for example, N,N-dimethylformamide, tetrahydrofuran, toluene, ethyl acetate, chloroform, dimethoxyethane, xylene, dimethylformamide, etc. The reaction is carried out at a temperature of from $-10°$ C. to room temperature, preferably at a temperature of from $0°$ C. to room temperature.

The reaction of the compound (XXXV) with the compound (VI) or a salt thereof can be carried out in the same manner as in the reaction of the compound (V) with the compound (VI).

The reaction of removing the protecting group $R^5$ for a carboxyl group of the compound (XXXVI) to give the compound (XXXVII) can be carried out in the same manner as in the reaction of removing the protecting group $R^5$ for a carboxyl group of the compound (VII) to give the compound (VIII).

The reaction of the compound (XXXVII) with the compound (IX-a) can be carried out in the same manner as in the reaction of the compound (VIII) with the compound (IX-a).

The oxidation reaction of the compound (XXXIX) can be carried out in the same manner as the reaction of the compound (IV) to give the compound (V). The oxidating agent is preferably m-chloroperbenzoic acid, etc. The solvent may be any solvent which does not disturb the reaction, for example, chloroform, methylene chloride, dichloroethane, acetic acid, etc. The reaction is carried out at a temperature of from $-78°$ C. to $50°$ C., preferably at a temperature of from $-10°$ C. to $10°$ C.

The subsequent reaction with the compound (III) can be carried out in the same manner as in the reaction of the compound (II) and the compound (III).

The compound (I) thus obtained can be converted into a pharmaceutically acceptable salt thereof.

The starting compound (II) can be prepared, for example, according to the method disclosed in Journal of American Chemical Society, p. 350, vol. 65, 1943.

Examples of the compound (I) of the present invention which can be prepared by the above exemplified methods are illustrated below, but the present invention should not be construed to be limited thereto.

EXAMPLE 1

(1) To a solution of 4-chloro-5-ethoxycarbonyl-2-methylthiopyrimidine (25.33 g) in N,N-dimethylformamide (85 ml) are added a solution of 3-chloro-4-methoxybenzylamine (19.62 g) in N,N-dimethylformamide (15 ml) and triethylamine (16.7 ml) under ice-cooling. The mixture is stirred at room temperature for 20 minutes, and thereto is added 3-chloro-4-methoxybenzylamine (940 mg), and the mixture is further stirred for 15 minutes. To the mixture is further added said amine (940 mg), and the mixture is stirred for 15 minutes. The reaction mixture is poured into a mixture of ice water and citric acid, and the mixture is extracted with ethyl acetate. The extract is washed successively with a 10% aqueous citric acid solution, water and brine, and dried over anhydrous sodium sulfate. The solvent is evaporated under reduced pressure, and the residue is washed with n-hexane to give 4-(3-chloro-4-methoxybenzylamino)-5-ethoxycarbonyl-2-methylthiopyrimidine (38.34 g), m.p. 86° C.

(2) To a solution of the compound (5.00 g) obtained in the above (1) in chloroform (50 ml) is added a solution of m-chloroperbenzoic acid (4.00 g) in chloroform (50 ml) under ice-cooling, and the mixture is stirred for 2 hours. The reaction mixture is washed with a saturated aqueous sodium hydrogen carbonate solution and brine, and the organic layer is dried over anhydrous sodium sulfate, and the solvent is evaporated under reduced pressure to give crude 4-(3-chloro-4-methoxybenzylamino)-5-ethoxycarbonyl-2-methylsulfinylpyrimidine, MS (m/z): 447 (MH$^+$).

(3) The crude product obtained in the above (2) is dissolved in tetrahydrofuran (40 ml), and thereto is added a solution of L-prolinol (1.50 g) and triethylamine (1.60 g) in tetrahydrofuran (10 ml) at room temperature. The mixture is stirred overnight, and the reaction mixture is diluted with ethyl acetate, and washed with aqueous sodium hydrogen carbonate solution and brine. The organic layer is dried over anhydrous sodium sulfate, and the solvent is evaporated under reduced pressure. The residue is purified by silica gel column chromatography (solvent; chloroform) and crystallized from a mixture of ether and n-hexane to give (S)-4-(3-chloro-4-methoxybenzylamino)-5-ethoxycarbonyl-2-(2-hydroxymethyl-1-pyrrolidinyl)pyrimidine (4.72 g), m.p. 88–90° C., MS (m/z): 421 (MH$^+$).

(4) A mixture of the compound (3.4 g) obtained in the above (3), a 10% aqueous sodium hydroxide solution (23 ml), and dimethylsulfoxide (34 ml) is stirred at room temperature for 15 hours. The reaction mixture is poured into a 10% aqueous citric acid solution, and the precipitates are crystallized from a mixture of tetrahydrofuran and ether to give (S)-4-(3-chloro-4-methoxybenzylamino)-5-carboxy-2-(2-hydroxymethyl-1-pyrrolidinyl)pyrimidine (2.52 g), m.p. 205–208° C., MS (m/z): 391 (M–H)$^-$.

(5) A mixture of the compound (600 mg) obtained in the above (4), 2-aminomethylpyrimidine (217 mg), 1-(3-dimethylaminopropyl)-3-ethylcarbodiimide hydrochloride (323 mg), 1-hydroxybenzotriazole monohydrate (227 mg) and N,N-dimethylformamide (12 ml) is stirred at room temperature for 8 hours, and the reaction mixture is poured into aqueous sodium hydrogen carbonate solution. The mixture is extracted with ethyl acetate, washed with brine, and dried over anhydrous sodium sulfate. The solvent is evaporated under reduced pressure, and the residue is purified by silica gel column chromatography (solvent; chloroform:methanol=50:1) to give (S)-2-(2-hydroxymethyl-1-pyrrolidinyl)-4-(3-chloro-4-methoxybenzylamino)-5-[N-(2-pyrimidylmethyl)carbamoyl]pyrimidine (610 mg), m.p. 160–163° C.

EXAMPLE 2

(1) To a suspension of lithium aluminum hydride (4.15 g) in tetrahydrofuran (150 ml) is added a solution of 2-methylthio-4-(3-chloro-4-methoxybenzylamino)-5-ethoxycarbonylpyrimidine (38.32 g) in tetrahydrofuran (100 ml) under ice-cooling at 5° C. to 10° C. over a period of one hour. After the addition, the ice bath is removed, and the reaction mixture is stirred at room temperature for one hour. To the reaction mixture is added water (4.15 ml) under ice-cooling, and thereto is further added 3N aqueous sodium hydroxide solution (4.15 ml). To the mixture is added water (4.15 ml) three times, and the mixture is stirred at room temperature for one hour. The reaction mixture is treated with magnesium sulfate, and the solid precipitates obtained are filtered. The precipitates are washed with tetrahydrofuran. The filtrate and the washings are combined, and concentrated under reduced pressure, and triturated with a mixture of ethyl acetate and isopropyl ether. The resulting crystals are collected by filtration, and washed well with isopropyl ether to give 2-methylthio-4-(3-chloro-4-methoxybenzylamino)-5-hydroxymethylpyrimidine as pale yellow crystalline powder.

First production: yield; 25.10 g, m.p. 162–163° C.
Second production: yield; 2.32 g, m.p. 159–160° C.

In addition, the above solid precipitates are washed again with isopropyl ether, and the filtrate is concentrated under reduced pressure to give colorless crystals. The resulting solid is suspended in isopropyl ether, filtered, and the precipitates are washed well with isopropyl ether and hexane to give 2-methylthio-4-(3-chloro-4-methoxybenzylamino)-5-hydroxymethylpyrimidine (4.26 g) as colorless crystals, m.p. 161–162° C.

(2) To a suspension of 2-methylthio-4-(3-chloro-4-methoxybenzylamino)-5-hydroxymethylpyrimidine (25.10 g) obtained in the above (1) in chloroform (150 ml) is added manganese dioxide powder (37.6 g), and the mixture is vigorously stirred at room temperature for one day. To the mixture is further added manganese dioxide powder (12.6 g, 0.5 time amount of the starting compound), and the mixture is stirred for three days. The insoluble materials are quickly removed by filtration on celite, and the filtrate is concentrated under reduced pressure. The residue is suspended in a mixture of ethyl acetate and isopropyl ether. The precipitates are filtered, and washed successively with isopropyl ether and hexane to give 2-methylthio-4-(3-chloro-4-methoxybenzylamino)-5-formylpyrimidine (22.43 g) as colorless crystals, m.p. 124–125° C.

(3) A solution of 2-methylthio-4-(3-chloro-4-methoxybenzylamino)-5-formylpyrimidine (2.057 g) in chloroform (20 ml) is treated with m-chloroperbenzoic acid (80%, 1.468 g) at 0° C. for 30 minutes. To the reaction mixture are is added L-prolinol (0.901 g), and then triethylamine (1.33 ml), and the mixture is reacted at 0° C. for one hour. The reaction mixture is warmed to room temperature, and diluted with ethyl acetate. The mixture is washed successively with a saturated aqueous sodium hydrogen carbonate solution, water and a saturated sodium chloride solution, and dried over anhydrous sodium sulfate. The precipitates are removed by filtration through a silica plug. The filtrate is concentrated under reduced pressure to give (S)-2-(2-hydroxymethyl-1-pyrrolidinyl)-4-(3-chloro-4-methoxybenzylamino)-5-formylpyrimidine (1.9990 g) as colorless amorphous, MS (m/z): 377 (MH$^+$).

(4) To a solution of (S)-2-(2-hydroxymethyl-1-pyrrolidinyl)-4-(3-chloro-4-methoxybenzylamino)-5-formylpyrimidine (91.0 mg) in tetrahydrofuran (20 ml) is added 1.10 M solution of methyl lithium in ether (1.1 ml) at −78° C., and the mixture is reacted for 10 minutes, and thereto is added aqueous sodium hydrogen carbonate solution. The reaction mixture is extracted with ethyl acetate to give crude (S)-2-(2-hydroxymethyl-1-pyrrolidinyl)-4-(3-chloro-4-methoxybenzylamino)-5-(1-hydroxyethyl)pyrimidine, MS (m/z): 393 (MH$^+$).

(5) The crude product obtained in the above (4) is treated with manganese dioxide (0.5 g) at room temperature, and the mixture is stirred overnight. The reaction mixture is heated under reflux for 5 hours, and the insoluble materials are removed by filtration. The filtrate is concentrated under reduced pressure, and purified by silica gel column chromatography (solvent; chloroform:ethyl acetate=3:1) to give (S)-(2-hydroxymethyl-1-pyrrolidinyl)-4-(3-chloro-4-methoxybenzylamino)-5-acetylpyrimidine (56.7 mg) as colorless oil, MS (m/z): 391 (MH$^+$).

EXAMPLE 3

(1) To a solution of (S)-2-(2-hydroxymethyl-1-pyrrolidinyl)-4-(3-chloro-4-methoxybenzylamino)-5-formylpyrimidine (84 mg) in tetrahydrofuran (about 1 ml) is added dropwise a 1.0M solution of vinyl magnesium bromide in tetrahydrofuran in a dry ice-acetone bath. The reaction mixture is stirred at −78° C. for 10 minutes, and stirred at room temperature for 10 minutes. The reaction mixture is poured into a mixture of ice and a saturated aqueous sodium hydrogen carbonate solution, and the mixture is extracted with ethyl acetate. The organic layer is washed successively with water and brine, dried over anhydrous sodium sulfate, and concentrated under reduced pressure.

The obtained crude product is subjected to preparative thin layer chromatography (solvent; ethyl acetate:methanol= 20:1) to give (S)-2-(2-hydroxymethyl-1-pyrrolidinyl)-4-(3-chloro-4-methoxybenzylamino)-5-(1-hydroxy-2-propen-1-yl)pyrimidine (30 mg) as colorless oil, MS (m/z): 405 (MH$^+$).

(2) To a solution of (S)-2-(2-hydroxymethyl-1-pyrrolidinyl)-4-(3-chloro-4-methoxybenzylamino)-5-(1-hydroxy-2-propen-1-yl)pyrimidine (144 mg) in chloroform (2.5 ml) is added manganese dioxide (432 mg), and the mixture is vigorously stirred at room temperature for three days. The insoluble materials are removed by filtration on celite, and the filtrate is concentrated under reduced pressure to give pale yellow oil (124 mg). The resulting crude product is purified by silica gel column chromatography (silica gel 20 g, solvent; chloroform:ethyl acetate=2:1) to give (S)-2-(2-hydroxymethyl-1-pyrrolidinyl)-4-(3-chloro-4-methoxybenzylamino)-5-(acryloyl)pyrimidine (90 mg) as colorless crystals, m.p. 113–115° C., MS (m/z): 403 (MH$^+$).

(3) To a solution of (S)-2-(2-hydroxymethyl-1-pyrrolidinyl)-4-(3-chloro-4-methoxybenzylamino)-5-(acryloyl) pyrimidine (72 mg) in ethanol (2 ml) is added morpholine (78 μl) at room temperature, and the mixture is stirred at room temperature for 40 minutes. The reaction mixture is concentrated under reduced pressure, and the residue is poured into water, and the mixture is extracted with ethyl acetate. The organic layer is washed successively with water and brine, dried over anhydrous magnesium sulfate, and concentrated to dryness under reduced pressure to give (S)-2-(2-hydroxymethyl-1-pyrrolidinyl)-4-(3-chloro-4-methoxybenzylamino)-5-[(2-morpholinoethyl) carbonyl]-pyrimidine (91 mg).

The obtained crude product is dissolved in ethyl acetate (10 ml), and the solution is treated with a saturated solution of hydrochloric acid in methanol (5 ml), and concentrated under reduced pressure. To the residue is added ethyl acetate, and the mixture is filtered. The resulting solid is washed well with hexane to give (S)-2-(2-hydroxymethyl-1-pyrrolidinyl)-4-(3-chloro-4-methoxybenzylamino)-5-[(2-morpholinoethyl)carbonyl]pyrimidine dihydrochloride (65 mg), MS (m/z): 490 (MH$^+$).

EXAMPLE 4

(1) To a solution of 4-(3-chloro-4-methoxybenzylamino)-5-ethoxycarbonyl-2-methylthiopyrimidine (972 mg) obtained in the above Example 1-(1) in chloroform (8 ml) is added a solution of m-chloroperbenzoic acid (80%, 598 mg) in chloroform (10 ml) under ice-cooling over a period of 30 minutes. The reaction mixture is stirred under ice-cooling for one hour. The reaction mixture is diluted with a saturated aqueous sodium hydrogen carbonate solution, and the chloroform layer is collected, washed successively with a saturated aqueous sodium hydrogen carbonate solution, water and a saturated aqueous sodium chloride solution, dried over anhydrous sodium sulfate, and concentrated under reduced pressure to quantitatively give 2-methylsulfinyl-4-(3-chloro-4-methoxybenzylamino)-5-ethoxycarbonylpyrimidine as colorless caramels, MS (m/z): 384 (MH$^+$).

(2) To a solution of 2-methylsulfinyl-4-(3-chloro-4-methoxybenzylamino)-5-ethoxycarbonylpyrimidine (whole amount) obtained in the above (1) in tetrahydrofuran (6 ml) is added dropwise a 2N aqueous sodium hydroxide solution (1.32 ml) under ice-cooling over a period of 2 minutes. The reaction mixture is stirred under ice-cooling for 30 minutes, and thereto are added tetrahydrofuran (8 ml) and N,N-dimethylacetamide (6 ml). The reaction mixture is stirred under ice-cooling for 30 minutes, and thereto are added water (5 ml) and N,N-dimethylacetamide (2 ml), and stirred under ice-cooling for one hour. The reaction mixture is acidified with a 10% aqueous citric acid solution, diluted with water, and extracted twice with ethyl acetate. The extracts are combined, washed with water and a saturated aqueous sodium chloride solution, dried over anhydrous sodium sulfate, and concentrated under reduced pressure. The residue is separated by silica gel column chromatography (silica gel: 20 g, solvent; chloroform: ethyl acetate= 5:1→chloroform:isopropanol=30:1) to give 2-hydroxy-4-(3-chloro-4-methoxybenzylamino)-5-ethoxycarbonylpyrimidine (618 mg) as slightly yellow crystalline powder, m.p. 195–197° C.

(3) A mixture of 2-hydroxy-4-(3-chloro-4-methoxybenzylamino)-5-ethoxycarbonylpyrimidine (500 mg) obtained in the above (2), diethylaminobenzene (2 ml) and phosphorus oxychloride (4 ml) is stirred at 80° C. for 30 minutes, and stirred at 100° C. for 5 hours. After cooling, the reaction solution is poured into ice-water, and the mixture is stirred at room temperature for 30 minutes. The resulting mixture is extracted with ethyl acetate, and the organic layer is washed with water and a saturated aqueous sodium chloride solution, dried over anhydrous sodium sulfate, and concentrated under reduced pressure. The residue is purified by silica gel column chromatography (silica gel: 7 g, solvent; chloroform) to give 2-chloro-4-(3-chloro-4-methoxybenzylamino)-5-ethoxycarbonylpyrimidine (375 mg) as slightly yellow crystalline powder, m.p. 114–115°, MS (m/z): 356 (MH$^+$).

(4) A mixture of 2-chloro-4-(3-chloro-4-methoxybenzylamino)-5-ethoxycarbonylpyrimidine (285 mg) obtained in the above (3), 5,6,7,8-tetrahydroimidazo[1,2-a]pyrazine (197 mg), triethylamine (0.22 ml) and chloroform (3 ml) is stirred at room temperature for 2.5 hours, and stirred at 60° C. for 2.5 hours. The reaction mixture is diluted with ethyl acetate, and washed with water. The aqueous layer is extracted with ethyl acetate, and the organic layer is washed with water and a saturated aqueous sodium chloride solution, dried over anhydrous sodium sulfate, and concentrated under reduced pressure. The residue is purified by silica gel column chromatography (silica gel: 10 g, solvent; chloroform:methanol= 50:1), and concentrated under reduced pressure. The resultant is triturated with isopropyl ether to give 2-(5,6,7,8-tetrahydroimidazo[1,2-a]pyrazin-7-yl)-4-(3-chloro-4-methoxybenzylamino)-5-ethoxycarbonylpyrimidine (290 mg) as colorless crystalline powder, m.p. 179–182° C., MS (m/z): 443 (MH$^+$).

(5) A suspension of 2-(5,6,7,8-tetrahydroimidazo[1,2-a]pyrazin-7-yl)-4-(3-chloro-4-methoxybenzylamino)-5-ethoxycarbonylpyrimidine (290 mg) obtained in the above (4) and 2N aqueous sodium hydroxide solution (1.64 ml) in a mixture of dimethylsulfoxide (5 ml) and water (1 ml) is stirred at room temperature for one hour. To the mixture is added tetrahydrofuran (5 ml), and the mixture is stirred at room temperature for 13 hours. Tetrahydrofuran is evaporated under reduced pressure, and the resulting solution is diluted with water, and neutralized with a 10% aqueous citric acid solution. The precipitates are collected by filtration, washed with water, methanol and isopropyl ether to give 2-(5,6,7,8-tetrahydroimidazo[1,2-a]pyrazin-7-yl)-4-(3-chloro-4-methoxybenzylamino)-5-carboxypyrimidine (187 mg) as colorless crystalline powder, m.p. 223–226° C. (decomposed), MS (m/z): 413 (M–H)$^-$.

(6) A mixture of 2-(5,6,7,8-tetrahydroimidazo[1,2-a]pyrazin-7-yl)-4-(3-chloro-4-methoxybenzylamino)-5-carboxypyrimidine (60 mg), 4-methyl-2-aminomethylmorpholine (22.7 mg), 1-(3-dimethylaminopropyl)-3-ethylcarbodiimide hydrochloride (30.6 mg), 1-hydroxybenzotriazole (21.6 mg) and N,N-dimethylformamide (3 ml) is stirred at room temperature for 22 hours. Water is poured into the reaction mixture, and the mixture is extracted with ethyl acetate. The organic layer is washed successively with water, a saturated aqueous sodium hydrogen carbonate solution, water and brine, dried over anhydrous sodium sulfate, and concentrated under reduced pressure to give the colorless crystals (70.0 mg), which are further recrystallized from a mixture of chloroform and hexane to give 2-(5,6,7,8-tetrahydroimidazo[1,2-a]-pyrazin-7-yl)-4-(3-chloro-4-methoxybenzylamino)-5-[N-[(4-methyl-2-morpholinyl)methyl]carbamoyl]pyrimidine (51.7 mg) as colorless needles, m.p. 132–134° C., MS (m/z): 527 (MH$^+$).

EXAMPLES 5–6

The corresponding starting materials are treated in a similar manner as in Example 4-(6) to give the compounds as listed in the following Table 1.

TABLE 1

[Structure: pyrimidine core with imidazo-pyrazine group, NH-CH2-(3-chloro-4-methoxyphenyl), and COR¹ substituent]

| Ex. No. | R¹ | Physiochemical properties |
|---|---|---|
| 5 | [CH2-NH- linked to pyrimidin-2-yl] | Powder MS(m/z):506 (MH⁺) |
| 6 | [trans-4-hydroxycyclohexyl-NH-] | Powder MS(m/z):512 (MH⁺) |

EXAMPLE 7–21

The corresponding starting materials are treated in a similar give the compounds as listed in the following Table 2.

TABLE 2

[General structure: pyrimidine with A-N- group at 2-position, NH-CH2-(4-methoxy-3-R⁰-phenyl) at 4-position, and C(=O)R¹ at 5-position]

| Ex. No. | A-N— | R⁰ | R¹ | Physiochemical properties |
|---|---|---|---|---|
| 7 | [tetrahydro-1,7-naphthyridinyl] | Cl | —NH—CH2CH2—morpholinyl | Amorphous MS(m/z):538 (MH⁺) |
| 8 | [methyl-imidazo-tetrahydropyrazinyl] | Cl | —NH—(trans-4-methoxycyclohexyl) | Amorphous MS(m/z):526 (MH⁺) |
| 9 | [methyl-dihydropyrrolo-pyridinyl] | CN | —NH—CH2-(pyrimidin-2-yl) | M.p. 243–245° C. |
| 10 | [methyl-dihydropyrrolo-pyridinyl] | CN | —NH—(trans-4-hydroxycyclohexyl) | Amorphous MS(m/z):500 (MH⁺) |
| 11 | [methyl-dihydropyrrolo-pyridinyl] | CN | —NH—CH2CH2—morpholinyl | M.p. 129–132° C. |

TABLE 2-continued

| Ex. No. | A N— | R⁰ | R¹ | Physiochemical properties |
|---|---|---|---|---|
| 12 | imidazo[1,2-a]piperazine (N-Me) | Cl | -NH-CH2CH2-morpholine | M.p. 150–152° C. |
| 13 | (S)-1-methyl-2-(hydroxymethyl)pyrrolidine | Cl | -NH-CH2-(2-pyridyl) | Powder (HCl) MS(m/z):483 (MH⁺) |
| 14 | (S)-1-methyl-2-(hydroxymethyl)pyrrolidine | Cl | -NH-CH2-(5-pyrimidinyl) | Amorphous MS(m/z):484 (MH⁺) |
| 15 | (S)-1-methyl-2-(hydroxymethyl)pyrrolidine | Cl | -NH-CH2CH2-morpholine | Caramel MS(m/z):505 (MH⁺) |
| 16 | 1,4-dimethyl-piperazin-2-one | Cl | trans-HN-cyclohexyl-OH | Amorphous MS(m/z):503 (MH⁺) |
| 17 | (S)-1-methyl-2-(hydroxymethyl)pyrrolidine | Cl | -NH-CH2-(4-pyridazinyl) | Amorphous MS(m/z):484 (MH⁺) |
| 18 | (S)-1-methyl-2-(hydroxymethyl)pyrrolidine | Cl | -NH-CH2-(4-pyrimidinyl) | Amorphous MS(m/z):484 (MH⁺) |
| 19 | (S)-1-methyl-2-(hydroxymethyl)pyrrolidine | Cl | -NH-CH2-(4-Me-morpholin-2-yl) | Amorphous MS(m/z):505 (MH⁺) |
| 20 | 4-formyl-1-methyl-piperazine | Cl | trans-HN-cyclohexyl-OH | Foam MS(m/z):503 (MH⁺) |
| 21 | (2S,5S)-1-methyl-2,5-bis(hydroxymethyl)pyrrolidine | Cl | -NH-CH2-(2-pyrimidinyl) | Amorphous MS(m/z):514 (MH⁺) |

EXAMPLE 22

To a solution of diisopropylamine (0.78 g) in tetrahydrofuran (40 ml) is added dropwise a 1.6M solution of n-butyl lithium in hexane (4.82 ml) in a dry ice-acetone bath over a period of 3 minutes. The mixture is stirred in the same bath for 30 minutes. To the mixture is added dropwise a solution of 2,6-dichloropyrazine (0.50 g) in tetrahydrofuran (5 ml) at the same temperature over a period of 15 minutes, and the mixture is stirred for one hour. The reaction mixture is poured into dry ice, and the mixture is stirred at room temperature for one hour. The reaction mixture is diluted with a 10% aqueous hydrochloric acid solution in order to adjust the pH value thereof to about 2, and then extracted with ethyl acetate. The combined organic layers are extracted with a saturated aqueous sodium hydrogen carbonate solution, and the aqueous extract is washed with ethyl acetate, acidified with a 10% aqueous hydrochloric acid, and extracted with ethyl acetate. The combined organic layer is washed with water and a saturated aqueous sodium chloride solution, dried over anhydrous sodium sulfate, and concentrated under reduced pressure. The residue is triturated with a mixture of chloroform and hexane (1:1) to give 2-carboxy-3,5-dichloropyrazine (234 mg) as a slightly brown crystalline powder, m.p. 139–141° C., MS (m/z): 191 $(M-H)^-$.

(2) A mixture of 2-carboxy-3,5-dichloropyrazine (226 mg) obtained in the above (1), sodium hydrogen carbonate (118 mg), methyl iodide (0.5 ml) and N,N-dimethylformamide (1.8 ml) is stirred at room temperature for 14 hours. The mixture is diluted with a 10% aqueous citric acid solution, and extracted with ethyl acetate. The combined organic layer is washed with water and a saturated aqueous sodium chloride solution, dried over anhydrous sodium sulfate, and concentrated under reduced pressure to give 2-methoxycarbonyl-3,5-dichloropyrazine (245 mg) as pale brown crystalline powder, m.p. 60–63° C., MS (m/z): 206 $(M^+)$.

(3) A mixture of 2-methoxycarbonyl-3,5-dichloropyrazine (234 mg) obtained in the above (2), 3-chloro-4-methoxybenzylamine (204 mg), triethylamine (0.17 ml) and dry toluene (3 ml) is stirred at room temperature for 7 hours. The reaction mixture is diluted with a 10% aqueous citric acid solution, and extracted with ethyl acetate. The extract is washed with water and a saturated aqueous sodium chloride solution, dried over sodium sulfate, and concentrated under reduced pressure. The residue is separated and purified by silica gel column chromatography (silica gel: 5 g, solvent; hexane:chloroform=1:1), and the desired fractions are concentrated under reduced pressure to give 2-methoxycarbonyl-3-(3-chloro-4-methoxybenzylamino)-5-chloropyrazine (102 mg) as pale yellow crystalline powder, m.p. 149–151° C., MS (m/z): 342 $(MH^+)$.

(4) A mixture of 2-methoxycarbonyl-3-(3-chloro-4-methoxybenzylamino)-5-chloropyrazine (150 mg), 2-hydroxymethylpyrrolidine (88.6 mg), and triethylamine (0.12 ml) in tetrahydrofuran (5 ml) is stirred at room temperature for 4 hours, and the mixture is heated at 50° C. for 2 hours. To the mixture is added 2-hydroxymethylpyrrolidine (44.3 mg), and the mixture is stirred at 50° C. for one hour. After cooling, water is added to the reaction mixture, and the mixture is extracted with ethyl acetate. The extract is washed with water and brine, dried over anhydrous sodium sulfate, and concentrated under reduced pressure. The resulting yellow oil is purified by silica gel column chromatography (solvent; chloroform:hexane=1:1) to give (S)-2-methoxycarbonyl-3-(3-chloro-4-methoxybenzylamino)-5-(2-hydroxymethyl-1-pyrrolidinyl)-pyrazine (123 mg) as pale yellow powder, MS (m/z): 407 $(MH^+)$.

(5) To a solution of (S)-2-methoxycarbonyl-3-(3-chloro-4-methoxybenzylamino)-5-(2-hydroxymethyl-1-pyrrolidinyl)pyrazine (775 mg) obtained in the above (4) in ethanol (8 ml) is added a 4N aqueous sodium hydroxide solution (1.43 ml), and the mixture is stirred at room temperature for 24 hours. The reaction mixture is acidified with 10% aqueous hydrochloric acid solution, and extracted with ethyl acetate. The organic layer is washed with water and brine, dried over anhydrous sodium sulfate, concentrated under reduced pressure, and washed with diisopropyl alcohol to give (S)-2-carboxy-3-(3-chloro-4-methoxybenzylamino)-5-(2-hydroxymethyl-1-pyrrolidinyl)pyrazine (537 mg) as yellow crystals, m.p. 169–171° C., MS (m/z): 391 $(M-H)^-$.

(6) A mixture of (S)-2-carboxy-3-(3-chloro-4-methoxybenzylamino)-5-(2-hydroxymethyl-1-pyrrolidinyl)pyrazine (80 mg) obtained in the above (5), 2-aminomethylpyrimidine (26.7 mg), 1,2-dichloroethane (43 mg), 1-hydroxybenzotriazole (30.3 mg) in N,N-dimethylformamide (3 ml) is stirred at room temperature for 18 hours. Water is poured into the reaction mixture, and extracted with ethyl acetate. The extract is washed with water, a saturated aqueous sodium hydrogen carbonate solution, and brine, dried over anhydrous sodium sulfate, and concentrated under reduced pressure. The residue is purified by silica gel column chromatography (solvent; ethyl acetate) to give (S)-2-[N-(2-pyrimidinylmethyl)carbamoyl]-3-(3-chloro-4-methoxybenzylamino)-5-(2-hydroxymethyl-1-pyrrolidinyl)pyrazine (87.6 mg), MS (m/z): 484 $(MH^+)$.

EXAMPLES 23–24

The corresponding starting materials are treated in a similar manner as in Example 22 to give the compounds as listed in the following Table 3.

TABLE 3

| Ex. No. | 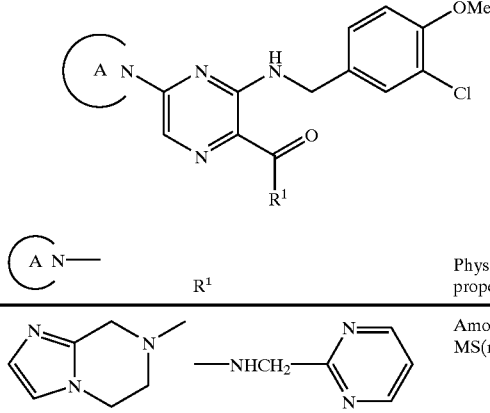 | R¹ | Physiochemical properties |
|---|---|---|---|
| 23 |  | —NHCH₂— 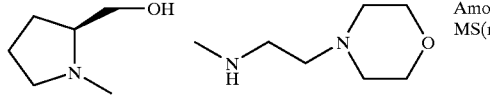 | Amorphous MS(m/z):506 (MH⁺) |
| 24 |  |  | Amorphous MS(m/z):505 (MH⁺) |

EXAMPLE 25

A mixture of (S)-2-(2-hydroxymethyl-1-pyrrolidinyl)-4-(3-chloro-4-methoxybenzylamino)-5-(acryloyl)pyrimidine (31 mg), methanol (1 ml) and conc. sulfuric acid (one drop) is heated under reflux for 2 days. After the reaction is complete, the solvent is evaporated under reduced pressure, and the residue is separated by silica gel thin layer chromatography (solvent; chloroform:methanol=30:1) to give (S)-2-(2-hydroxymethyl-1-pyrrolidinyl)-4-(3-chloro-4-methoxybenzylamino)-5-[(2-methoxyethyl)carbonyl]pyrimidine (27 mg) as colorless oil, MS (m/z): 435 (MH⁺).

EXAMPLE 26

A solution of (S)-2-(2-hydroxymethyl-1-pyrrolidinyl)-4-(3-chloro-4-methoxybenzylamino)-5-[N-(2-pyrimidinylmethyl)carbamoyl]-pyrimidine (82.48 g) and benzenesulfonic acid monohydrate (60.06 g) in methanol (1000 ml) is concentrated, and recrystallized from a mixture of methanol and acetone to give (S)-2-(2-hydroxymethyl-1-pyrrolidinyl)-4-(3-chloro-4-methoxybenzylamino)-5-[N-(2-pyrimidinylmethyl)-carbamoyl]pyrimidine dibenzenesulfonate (121.8 g) as colorless crystals, m.p. 158.5–161.5° C.

EXAMPLE 27

A mixture of (S)-4-(3-chloro-4-methoxybenzylamino)-5-carboxy-2-(2-hydroxymethyl-1-pyrrolidinyl)pyrimidine (100 mg) obtained in Example 1-(4), 4-amino-1,3,5-trimethylpyrazole (47.9 mg), 1-(3-dimethylaminopropyl)-3-ethylcarbodiimide hydrochloride (58.7 mg), 1-hydroxybenzotriazole monohydrate (41.3 mg), and N,N-dimethylformamide (3 ml) is stirred at room temperature for 8 hours, and poured into aqueous sodium hydrogen carbonate solution. The mixture is extracted with ethyl acetate, and the organic layer is washed with water and saturated brine, and dried over anhydrous sodium sulfate. The solvent is evaporated under reduced pressure, and the residue is purified by silica gel column chromatography (solvent; chloroform:methanol=5:1) to give (S)-2-(2-hydroxymethyl-1-pyrrolidinyl)-4-(3-chloro-4-methoxybenzylamino)-5-[N-(1,3,5-trimethyl-4-pyrazolyl)carbamoyl]pyrimidine (115 mg), MS (m/z): 500 (MH⁺).

EXAMPLE 28

(1) A solution of 4-chloro-5-ethoxycarbonyl-2-methylthiopyrimidine (5.0 g) in sulfuryl chloride (20 ml) is heated at 50° C. for one hour. The reaction mixture is concentrated, and thereto is poured a saturated aqueous sodium hydrogen carbonate solution. The mixture is extracted with ethyl acetate, and the organic layer is washed with water and brine, dried over sodium sulfate, and concentrated. The residue is purified by silica gel flash column chromatography (solvent; ethyl acetate=hexane=1:10) to quantitatively give 2,4-dichloro-5-ethoxycarbonylpyrimidine (4.87 g) as yellow oil, MS (m/z): 220 (M⁺).

(2) To a solution of 2,4-dichloro-5-ethoxycarbonylpyrimidine (4.2 g) obtained in the above (1) and mercaptobenzene (2.30 g) in toluene (40 ml) is added potassium carbonate (3.94 g) at 0° C., and the mixture is stirred at room temperature for one hour, stirred at 50° C. for one hour, and further stirred at 100° C. for 10 minutes. To the mixture is poured water, and the mixture is extracted with ethyl acetate. The organic layer is washed with brine, dried over sodium sulfate, and concentrated. The residue is purified by silica gel flash column chromatography (solvent; ethyl acetate:hexane=1:20→ethyl acetate:hexane=1:10) to give 2-chloro-4-phenylthio-5-ethoxycarbonylpyrimidine (4.16 g) as colorless crystals, MS (m/z): 295 (MH⁺).

(3) To a solution of 2-chloro-4-phenylthio-5-ethoxycarbonylpyrimidine (4.05 g) obtained in the above (2) in tetrahydrofuran (40 ml) are added L-prolinol (1.66 g) and triethylamine (2.77 g), and the mixture is stirred at room temperature for 20 hours. Water is poured into the reaction mixture, and the mixture is extracted with ethyl acetate. The organic layer is washed with brine, dried over sodium sulfate, and concentrated under reduced pressure. The residue is purified by silica gel flash column chromatography (solvent; ethyl acetate:hexane=1:2) to give (S)-2-(2-hydroxymethyl-1-pyrrolidinyl)-4-phenylthio-5-ethoxycarbonylpyrimidine (4.16 g) as colorless viscous oil, MS (m/z): 360 (MH$^+$).

(4) To a solution of (S)-2-(2-hydroxymethyl-1-pyrrolidinyl)-4-phenylthio-5-ethoxycarbonylpyrimidine (4.10 g) obtained in the above (3) in ethanol (50 ml) is added a 4N aqueous sodium hydroxide solution (8.6 ml), and the mixture is stirred at room temperature for 15 hours. To the reaction solution is added a 10% aqueous citric acid solution (30 ml) until the solution becomes weak acidic, and the mixture is extracted with ethyl acetate. The organic layer is washed with water and brine, dried over sodium sulfate, and concentrated to give (S)-2-(2-hydroxymethyl-1-pyrrolidinyl)-4-phenylthio-5-carboxypyrimidine (3.65 g) as colorless crystals, MS (m/z): 330 (M–H)$^-$.

(5) A mixture of (S)-2-(2-hydroxymethyl-1-pyrrolidinyl)-4-phenylthio-5-carboxypyrimidine (2.55 g) obtained in the above (4), 2-aminomethylpyrimidine (1.09 g), 1,2-dichloroethane (1.77 g) and 1-hydroxybenzotriazole (1.25 g) in N,N-dimethylformamide (40 ml) is stirred at room temperature for 16 hours. To the mixture is poured water, and the mixture is extracted with ethyl acetate. The organic layer is washed with water, a saturated aqueous sodium hydrogen carbonate solution and brine, dried over sodium sulfate, and concentrated to give pale yellow crystals (4.05 g), which is further purified by silica gel flash column chromatography (solvent; ethyl acetate) to give 2-(2-hydroxymethyl-1-pyrrolidinyl)-4-phenylthio-5-[N-(2-pyrimidylmethyl)carbamoyl]pyrimidine (2.39 g) as colorless crystals, m.p., 154–156° C., IR (Nujol): 1633 cm$^{-1}$, MS (m/z): 423 (MH$^+$).

(6) To a solution of (S)-2-(2-hydroxymethyl-1-pyrrolidinyl)-4-phenylthio-5-[N-(2-pyrimidylmethyl)carbamoyl]pyrimidine (100 mg) obtained in the above (5) in chloroform (3 ml) is added m-chloroperbenzoic acid (70.1 mg) at 0° C., and the mixture is stirred at 0° C. for 30 minutes. To the mixture are added 3-chlorobenzylamine (50.3 mg) and triethylamine (48.0 mg) at 0° C., and the mixture is stirred at room temperature for 17 hours. To the mixture is poured water, and the mixture is extracted with chloroform. The organic layer is washed with brine, dried over sodium sulfate, and concentrated under reduced pressure to give yellow oil (169 mg), which is purified by silica gel flash column chromatography (solvent; ethyl acetate), and triturated with a mixture of ethyl acetate and hexane to give (S)-2-(2-hydroxymethyl-1-pyrrolidinyl)-4-(3-chlorobenzylamino)-5-[N-(2-pyrimidylmethyl)-carbamoyl]pyrimidine (95.3 mg) as colorless powder, m.p. 153–156° C., IR (Nujol): 3241, 1637 cm$^{-1}$, MS (m/z): 454 (MH$^+$).

(7) To a solution of (S)-2-(2-hydroxymethyl-1-pyrrolidinyl)-4-phenylthio-5-[N-(2-pyrimidylmethyl)carbamoyl] pyrimidine (100 mg) obtained in the above (5) in chloroform (3 ml) is added m-chloroperbenzoic acid (70%, 70.1 mg) at 0° C., and the mixture is stirred at 0° C. for 30 minutes. To the mixture are added 4-methoxybenzylamine (48.8 mg) and triethylamine (48.0 mg) at 0° C., and the mixture is stirred at room temperature for 20 minutes. To the mixture is poured water, and the mixture is extracted with chloroform, and the organic layer is washed with brine, dried over sodium sulfate, and concentrated to give a yellow oil (143 mg), which is purified by silica gel flash column chromatography (solvent; ethyl acetate) to give (S)-2-(2-hydroxymethyl-1-pyrrolidinyl)-4-(4-methoxybenzylamino)-5-[N-(2-pyrimidylmethyl)-carbamoyl]pyrimidine (88.2 mg) as colorless powder, IR (Neat): 3296, 1633 cm$^{-1}$, MS (m/z): 450 (MH$^+$).

EXAMPLE 29

(1) A solution of (S)-2-(2-hydroxymethyl-1-pyrrolidinyl)-4-(3-chloro-4-methoxybenzylamino)-5-formylpyrimidine (10.0 mg) in tetrahydrofuran (1.0 ml) obtained in Example 2 (3) is treated with a 1.6M solution of n-butyl lithium in hexane (83 μl) at –78° C. for 3 minutes, and thereto is added an aqueous sodium hydrogen carbonate solution. The reaction mixture is extracted with ethyl acetate to give (S)-2-(2-hydroxymethyl-1-pyrrolidinyl)-4-(3-chloro-4-methoxybenzylamino)-5-(1-hydroxypentyl) pyrimidine (13.7 mg) as oil.

(2) (S)-2-(2-Hydroxymethyl-1-pyrrolidinyl)-4-(3-chloro-4-methoxybenzylamino)-5-(1-hydroxypentyl)pyrimidine obtained in the above is treated with manganese dioxide (25 mg) at room temperature, and thereto is added gradually additional manganese dioxide (100 mg), and the mixture is stirred overnight. The reaction mixture is heated under reflux for 5 hours, and the insoluble materials are removed by filtration. The filtrate is concentrated under reduced pressure, and separated with preparative thin layer chromatography to give (S)-2-(2-hydroxymethyl-1-pyrrolidinyl)-4-(3-chloro-4-methoxybenzylamino)-5-pentanoylpyrimidine (5.8 mg) as colorless oil, MS (m/z): 433 (MH$^+$).

EXAMPLES 30–83

The corresponding starting compounds are treated in a similar manner to give the compounds as listed in the following Table 4.

TABLE 4

| Ex. No. | A N— | R⁰ | R¹ | Physiochemical properties |
|---|---|---|---|---|
| 30 | 2-methyl-1,2,3,4-tetrahydroisoquinolin-yl | Cl | —NH-CH₂-(pyridin-2-yl) | M.p. 210–214° C. |
| 31 | 7-methyl-5,6,7,8-tetrahydro-1,7-naphthyridin-yl | Cl | HN-CH₂-(pyrimidin-2-yl) | Amorphous MS(m/z):517 (MH⁺) |
| 32 | 2-methyl-2,3-dihydro-1H-pyrrolo[3,4-b]pyridin-yl | Cl | HN-CH₂-(pyrimidin-2-yl) | Amorphous MS(m/z):503 (MH⁺) |
| 33 | 7-methyl-5,6,7,8-tetrahydro-1,7-naphthyridin-yl | Cl | —NH-CH₂-(4-methylmorpholin-2-yl) | Amorphous MS(m/z):538 (MH⁺) |
| 34 | (2-hydroxymethyl-1-methylpyrrolidin-yl) | Cl | —NH-CH₂-(4-amino-2-methylpyrimidin-5-yl) | HCl salt M.p. 223–226° C. |
| 35 | (2-hydroxymethyl-1-methylpyrrolidin-yl) | Cl | —NH-CH₂-(4-amino-2-methylpyrimidin-5-yl) | Amorphous MS(m/z):513 (MH⁺) |
| 36 | (2-hydroxymethyl-1-methylpyrrolidin-yl) | Cl | HN-(trans-4-methoxycyclohexyl) | Amorphous MS(m/z):504 (MH⁺) |
| 37 | 2-methyl-2,3-dihydro-1H-pyrrolo[3,4-b]pyridin-yl | Cl | —NH-CH₂CH₂-morpholino | MS(m/z):524 (MH⁺) |
| 38 | 2-methyl-2,3-dihydro-1H-pyrrolo[3,4-b]pyridin-yl | Cl | —NH-CH₂-(4-methylmorpholin-2-yl) | Amorphous MS(m/z):524 (MH⁺) |
| 39 | (2-hydroxymethyl-1-methylpyrrolidin-yl) | Cl | HN-(trans-4-hydroxycyclohexyl) | Foam MS(m/z):490 (MH⁺) |

TABLE 4-continued
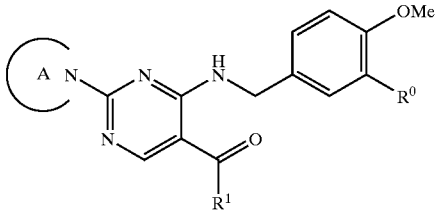
| Ex. No. | A N— | R⁰ | R¹ | Physiochemical properties |
|---|---|---|---|---|
| 40 | 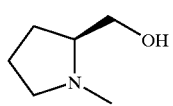 | Cl | 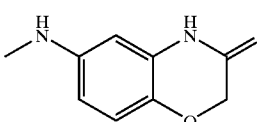 | Amorphous MS(m/z):539 (MH⁺) |
| 41 | 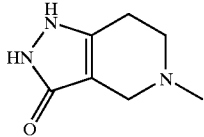 | Cl |  | Amorphous MS(m/z):528 (MH⁺) |
| 42 | 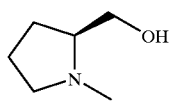 | Cl | 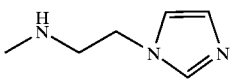 | Amorphous MS(m/z):500 (MH⁺) |
| 43 | 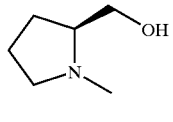 | Cl | 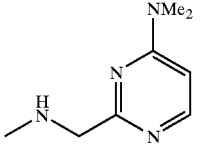 | Amorphous MS(m/z):527 (MH⁺) |
| 44 | 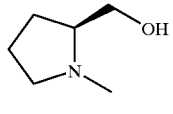 | Cl | 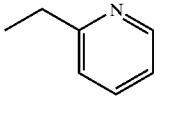 | Amorphous MS(m/z):468 (MH⁺) |
| 45 | 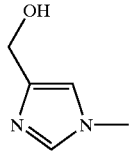 | Cl | 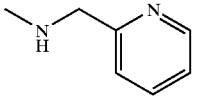 | M.p. 220–222° C. |
| 46 | 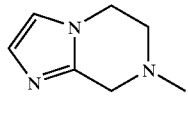 | NO₂ |  | Amorphous MS(m/z):523 (MH⁺) |
| 47 | 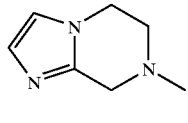 | NO₂ | 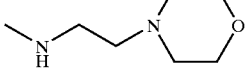 | M.p. 188–190° C. |
| 48 | 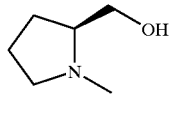 | Cl | 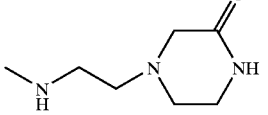 | Amorphous MS(m/z):518 (MH⁺) |

TABLE 4-continued
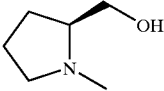
| Ex. No. | A N— | R⁰ | R¹ | Physiochemical properties |
|---|---|---|---|---|
| 49 | 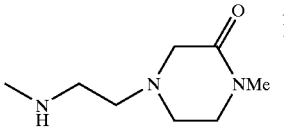 | Cl | 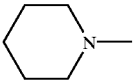 | Amorphous MS(m/z):532 (MH⁺) |
| 50 | 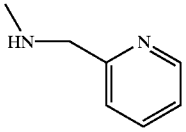 | Cl | 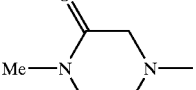 | M.p. 179–183° C. |
| 51 | 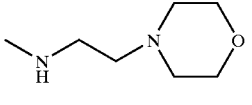 | Cl | 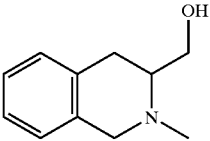 | Amorphous MS(m/z):518 (MH⁺) |
| 52 | 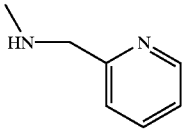 | Cl | 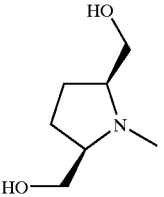 | Powder (HCl) MS(m/z):545 (MH⁺) |
| 53 |  | Cl | 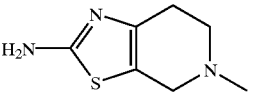 | Amorphous MS(m/z):520 (MH⁺) |
| 54 | 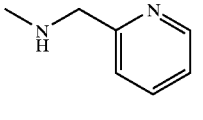 | Cl | 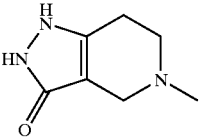 | Powder (HCl) MS(m/z):537 (MH⁺) |
| 55 | 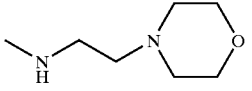 | Cl | 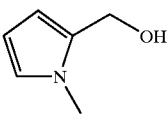 | Amorphous MS(m/z):543 (MH⁺) |
| 56 | 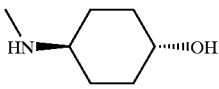 | Cl | | M.p. 181–183° C. |

TABLE 4-continued

| Ex. No. | A N— | R⁰ | R¹ | Physiochemical properties |
|---|---|---|---|---|
| 57 | OHCN-piperazine-N-Me | Cl | -NH-CH₂-(2-pyridyl) | Powder (HCl) MS(m/z):496 (MH⁺) |
| 58 | N-Me pyrrolidine-CH₂OH | Cl | -CH₂CH₂-SO₂Me | M.p. 199–200° C. |
| 59 | N-Me pyrrolidine-CH₂OH | NO₂ | HN-cyclohexyl-OH (trans) | M.p. 209.5–211.5° C. |
| 60 | Me-N-piperazin-2-one-N- | Cl | -NH-CH₂-(2-pyrimidyl) | M.p. 228–230.5° C. |
| 61 | tetrahydropyrido[4,3-d]pyrimidine N-Me | Cl | HN-cyclohexyl-OH (trans) | Amorphous MS(m/z):524 (MH⁺) |
| 62 | tetrahydropyrazolo[4,3-c]pyridin-3-one N-Me | Cl | -NH-CH₂-(2-pyrimidyl) | Amorphous MS(m/z):522 (MH⁺) |
| 63 | tetrahydroimidazo-pyridine-CO₂Me, N-Me | Cl | -NH-CH₂-(2-pyridyl) | Amorphous MS(m/z):563 (MH⁺) |
| 64 | N-Me-piperazin-2-one | Cl | HN-cyclohexyl-OH (trans) | Amorphous MS(m/z):489 (MH⁺) |

TABLE 4-continued
| Ex. No. | A N— | R⁰ | R¹ | Physiochemical properties |
|---|---|---|---|---|
| 65 |  | Cl | 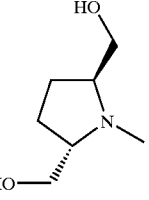 | Amorphous MS(m/z):520 (MH⁺) |
| 66 | 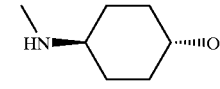 | Cl | 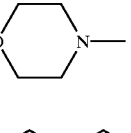 | M.p. 176–180° C. |
| 67 | 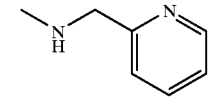 | CN | 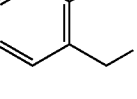 | Powder (HCl) MS(m/z):543 (MH⁺) |
| 68 | 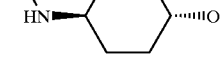 | Cl | 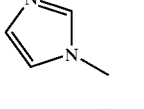 | M.p. 143–145° C. |
| 69 | 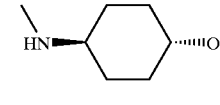 | Cl | 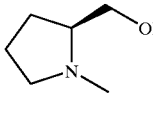 | Powder (HCl) MS(m/z):504 (MH⁺) |
| 70 | 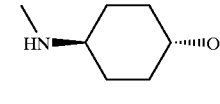 | Cl | 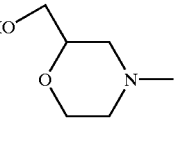 | M.p. 130° C. |
| 71 | 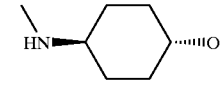 | CN | 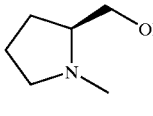 | Powder (HCl) MS(m/z):474 (MH⁺) |
| 72 | 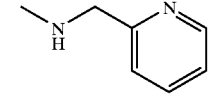 | Cl | 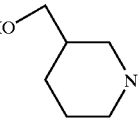 | Amorphous MS(m/z):519 (MH⁺) |
| 73 | 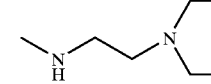 | CN | 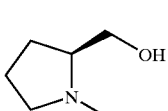 | Powder (HCl) MS(m/z):481 (MH⁺) |
| 74 | 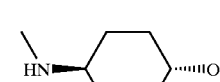 | Cl | 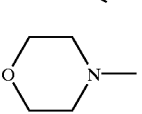 | M.p. 116–119° C. |

TABLE 4-continued

| Ex. No. | A N— | R⁰ | R¹ | Physiochemical properties |
|---|---|---|---|---|
| 75 | HO—, OHCN, N-Me piperazine | Cl | HN-cyclohexyl-OH (trans) | M.p. 159–161° C. |
| 76 | HO, HO, pyrrolidine-N-Me-CH₂OH | Cl | HN-cyclohexyl-OH (trans) | Powder (HCl) MS(m/z):506 (MH⁺) |
| 77 | HN, MeO₂C, tetrahydroimidazo-pyridine N-Me | Cl | HN-CH₂-pyridin-2-yl | Amorphous MS(m/z):563 (MH⁺) |
| 78 | piperidine N-Me, 2-CH₂OH | Cl | HN-CH₂-pyridin-2-yl | Powder (HCl) MS(m/z):497 (MH⁺) |
| 79 | HO-piperidine-N-Me (4-OH) | Cl | HN-CH₂-pyridin-2-yl | M.p. 210–214° C. |
| 80 | HO-CH₂-piperidine-N-Me (3-) | Cl | HN-CH₂-pyrimidin-2-yl | M.p. 149–151.5° C. |
| 81 | pyrrolidine-N-Me-CH₂OH | NO₂ | HN-CH₂-pyrimidin-2-yl | Amorphous MS(m/z):495 (MH⁺) |
| 82 | isoindoline N-Me | Cl | HN-CH₂-pyridin-2-yl | M.p. 215° C. |
| 83 | HO-CH₂-piperidine-N-Me (3-) | Cl | HN-cyclohexyl-OH (trans) | M.p. 151–152° C. |

EXAMPLE 84–86

The corresponding starting compounds are treated in a similar manner to give the compounds as listed in the following Table 5.

TABLE 5

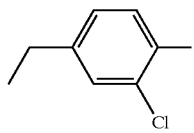

| Ex. No. | R⁸ | R¹ | Physiochemical properties |
|---|---|---|---|
| 84 | 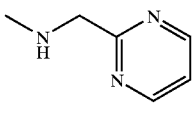 | 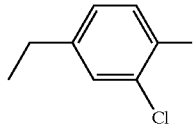 | Foam<br>MS(m/z):470 (MH⁺) |
| 85 | 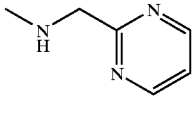 | 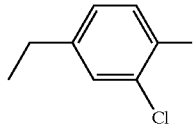 | Powder<br>MS(m/z):488 (MH⁺) |
| 86 | 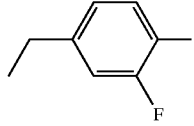 | 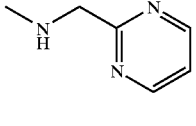 | Powder<br>MS(m/z):468 (MH⁺) |

EXAMPLE 87

A mixture of (S)-2-carboxy-3-(3-chloro-4-methoxybenzylamino)-5-(2-hydroxymethyl-1-pyrrolidinyl)pyrazine (80 mg) obtained in Example 22 (5), 2-aminomethyl-4-methylmorpholine (31.9 mg), 1-ethyl-3-(3-dimethylaminopropyl)carbodiimide hydrochloride (43 mg), 1-hydroxybenzotriazole (30.3 mg) in N,N-dimethylformamide (3 ml) is stirred at room temperature for 18 hours. To the reaction mixture is poured water, and the mixture is extracted with ethyl acetate. The extract is washed with water, a saturated aqueous sodium hydrogen carbonate solution and brine, dried over anhydrous sodium sulfate, and concentrated under reduced pressure. The residue is purified by silica gel flash column chromatography (solvent; ethyl acetate) to give (S)-2-[N-(4-methyl-2-morpholinyl)methylcarbamoyl]-3-(3-chloro-4-methoxybenzylamino)-5-(2-hydroxymethyl-1-pyrrolidinyl)pyrazine (80.5 mg), MS (m/z): 505 (MH⁺), IR (Nujol): 3295, 1635 cm⁻¹.

EXAMPLES 88–91

The corresponding starting compounds are treated in a similar manner to give the compounds as listed in the following Table 6.

TABLE 6
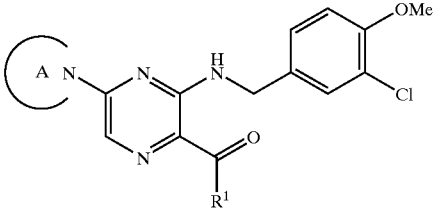
| Ex. No. | A N— | R¹ | Physiochemical properties |
|---|---|---|---|
| 88 |  | 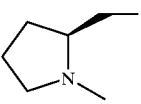 | M.p. 177–179° C, MS(m/z):490 (MH⁺) |
| 89 | 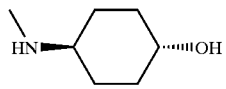 | 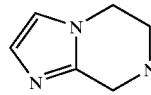 | M.p. 167–169° C. MS(m/z):512 (MH⁺) |
| 90 | 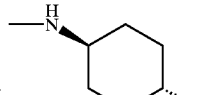 | 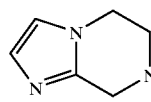 | M.p. 140.5–141.5° C. |
| 91 | 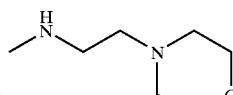 | 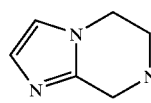 | Amorphous MS(m/z):527 (MH⁺) |
EXAMPLES 92–145
The corresponding starting compounds are treated in a similar give the compounds as listed in the following Table 7.
TABLE 7
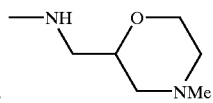
| Ex. No. | A N— | R¹ | Physiochemical properties |
|---|---|---|---|
| 92 | 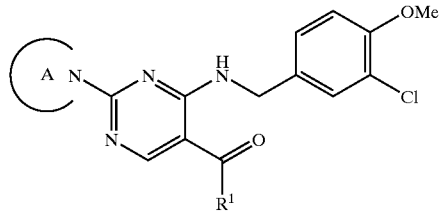 |  | Powder MS(m/z):475 (MH⁺) |
| 93 | 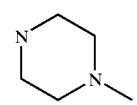 | 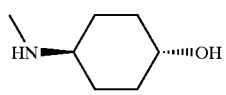 | Powder MS(m/z):509 (MH⁺) |

TABLE 7-continued
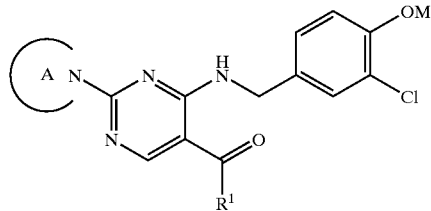
| Ex. No. | A N— | R[1] | Physiochemical properties |
|---|---|---|---|
| 94 |  | 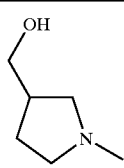 | Amorphous MS(m/z):512 (MH[+]) |
| 95 | 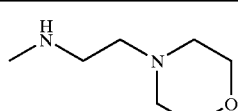 | 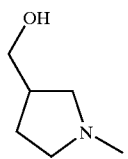 | M.p. 150–152° C. |
| 96 | 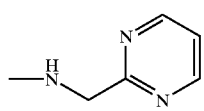 | 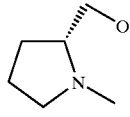 | M.p. 162–163° C. |
| 97 | 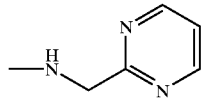 | 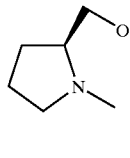 | Amorphous MS(m/z):486 (MH[+]) |
| 98 | 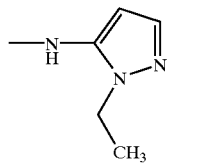 | 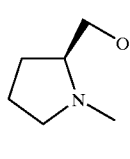 | Amorphous MS(m/z):484 (MH[+]) |
| 99 | 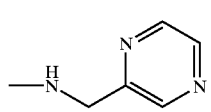 | 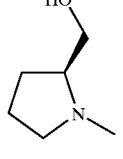 | Amorphous MS(m/z):483 (MH[+]) |
| 100 | 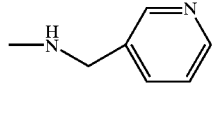 | 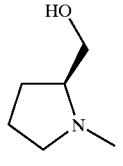 | Amorphous MS(m/z):497 (MH[+]) |
| 101 | 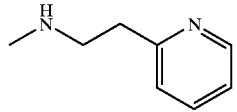 | 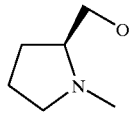 | M.p. 148–150° C. |

TABLE 7-continued
| Ex. No. | A N— | R¹ | Physiochemical properties |
|---|---|---|---|
| 102 | 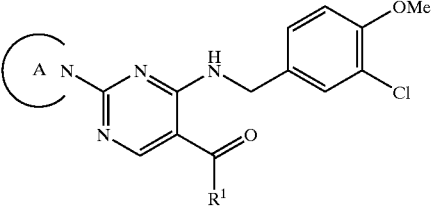 | 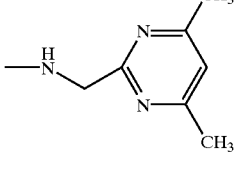 | Amorphous MS(m/z):512 (MH⁺) |
| 103 | 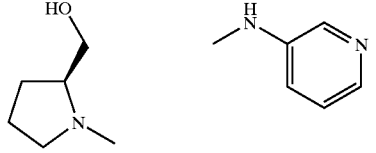 | 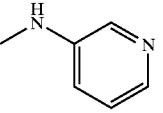 | M.p. 210–213° C. |
| 104 | 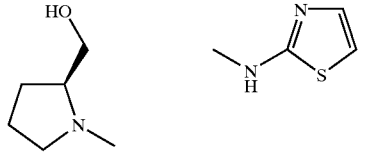 | 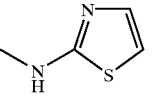 | M.p. 195–198° C. |
| 105 | 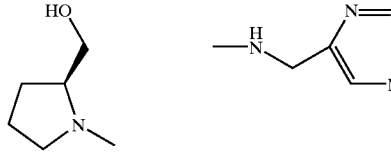 | 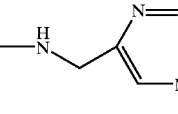 | Amorphous MS(m/z):498 (MH⁺) |
| 106 | 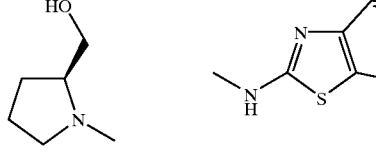 | 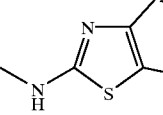 | M.p. 232–235° C. |
| 107 | 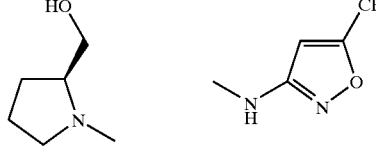 | 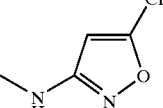 | M.p. 207–208° C. |
| 108 | 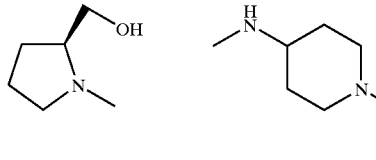 | 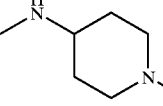 | Amorphous MS(m/z):547 (MH⁺) |

TABLE 7-continued

| Ex. No. | A N— | R¹ | Physiochemical properties |
|---|---|---|---|
| 109 | (S)-2-(hydroxymethyl)-1-methylpyrrolidine | —NH—CH₂—(3,5-dimethylisoxazol-4-yl) | Amorphous MS(m/z):501 (MH⁺) |
| 110 | (S)-2-(hydroxymethyl)-1-methylpyrrolidine | —NH—CH₂—(quinolin-2-yl) | M.p. 172–173° C. |
| 111 | (S)-2-(hydroxymethyl)-1-methylpyrrolidine | —NH—CH₂—(6-methylpyridin-2-yl) | M.p. 145–147° C. |
| 112 | (S)-2-(hydroxymethyl)-1-methylpyrrolidine | —NH—CH₂—(2-methylpyridin-3-yl) | Amorphous MS(m/z):497 (MH⁺) |
| 113 | (S)-2-(hydroxymethyl)-1-methylpyrrolidine | —NH—CH₂—(2-methylthiazol-4-yl) | M.p. 148–150° C. |
| 114 | (R)-2-(hydroxymethyl)-1-methylpyrrolidine | —NH—(1,3,4-thiadiazol-2-yl) | M.p. 217–219° C. |
| 115 | (S)-2-(hydroxymethyl)-1-methylpyrrolidine | —NH—CH₂—(pyridazin-3-yl) | Amorphous MS(m/z):484 (MH⁺) |
| 116 | (R)-2-(hydroxymethyl)-1-methylpyrrolidine | —NH—CH₂—(6-methoxypyrimidin-4-yl) | Amorphous MS(m/z):514 (MH⁺) |

TABLE 7-continued

| Ex. No. | A N— | R¹ | Physiochemical properties |
|---|---|---|---|
| 117 | (S)-1-methyl-2-(hydroxymethyl)pyrrolidinyl | NH-cyclohexyl-O-pyrimidin-2-yl | Amorphous MS(m/z):568 (MH⁺) |
| 118 | (S)-1-methyl-2-(hydroxymethyl)pyrrolidinyl | NH-(4-methylthiazol-2-yl) | M.p. 217–220° C. |
| 119 | (S)-1-methyl-2-(hydroxymethyl)pyrrolidinyl | NH-CH₂-(6-methyl-4-oxo-1H-pyrimidin-2-yl) | M.p. 212–214° C. |
| 120 | (S)-1-methyl-2-(hydroxymethyl)pyrrolidinyl | NH-(1-cyanomethylpiperidin-4-yl) | Amorphous MS(m/z):514 (MH⁺) |
| 121 | (S)-1-methyl-2-(hydroxymethyl)pyrrolidinyl | NH-CH₂-(5-oxo-2,5-dihydro-1H-pyrazol-3-yl) | Amorphous MS(m/z):488 (MH⁺) |
| 122 | (S)-1-methyl-2-(hydroxymethyl)pyrrolidinyl | NH-CH₂-(1-methyl-1H-pyrazol-4-yl) | M.p. 142–144° C. |
| 123 | (S)-1-methyl-2-(hydroxymethyl)pyrrolidinyl | NH-(5-methyl-1H-pyrazol-3-yl) | Amorphous MS(m/z):472 (MH⁺) |
| 124 | (S)-1-methyl-2-(hydroxymethyl)pyrrolidinyl | NH-CH₂-(5-methylpyridin-2-yl) | Amorphous MS(m/z):497 (MH⁺) |

TABLE 7-continued
| Ex. No. | 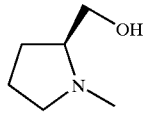 A N— | R¹ | Physiochemical properties |
|---|---|---|---|
| 125 | 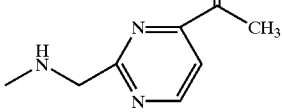 | 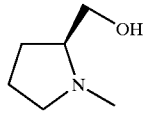 | M.p. 143–146° C. |
| 126 | 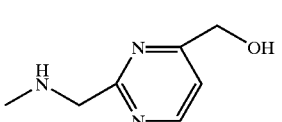 | 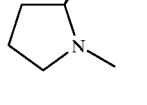 | Amorphous MS(m/z):514 (MH⁺) |
| 127 | 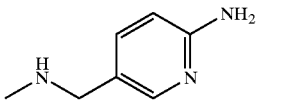 | 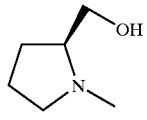 | Amorphous MS(m/z):498 (MH⁺) |
| 128 | 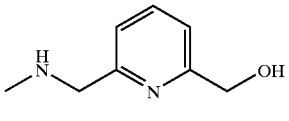 | 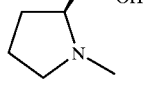 | Amorphous MS(m/z):513 (MH⁺) |
| 129 | 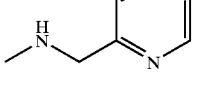 | 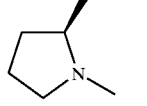 | M.p. 101–103° C. |
| 130 | 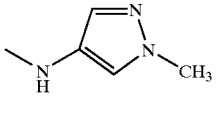 | 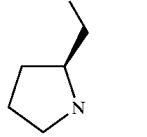 | M.p. 215–217° C. |
| 131 | 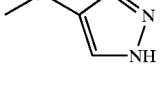 | 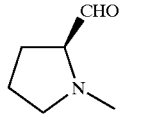 | M.p. 180–183° C. |
| 132 | 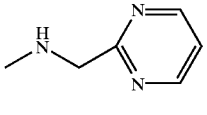 |  | Oil MS(m/z):482 (MH⁺) |

TABLE 7-continued
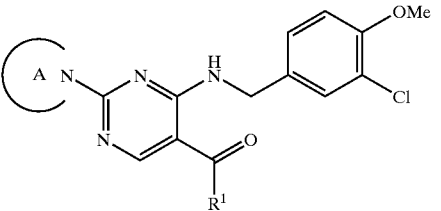
| Ex. No. | A N— | R[1] | Physiochemical properties |
|---|---|---|---|
| 133 | 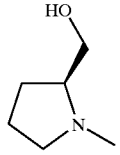 | 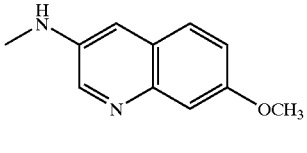 | M.p. 176–179° C. |
| 134 | 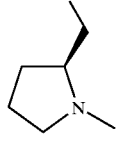 | 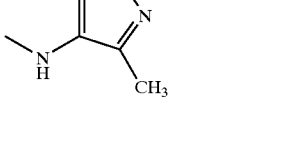 | M.p. 224–227° C. |
| 135 | 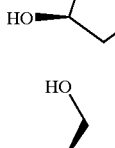 | 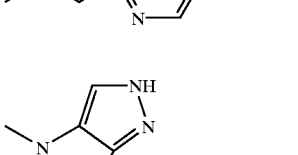 | Amorphous MS(m/z):500 (MH[+]) |
| 136 | 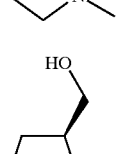 | 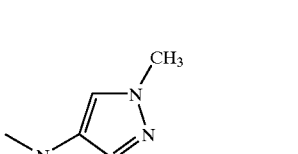 | M.p. 177–180° C. |
| 137 | 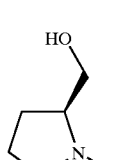 | 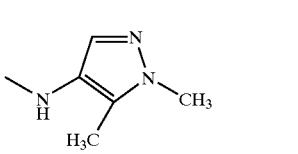 | Powder MS(m/z):486 (MH[+]) |
| 138 | 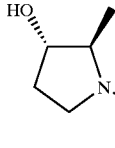 | 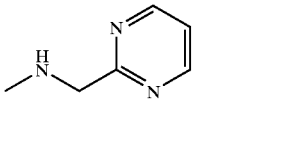 | Powder MS(m/z):486 (MH[+]) |
| 139 | 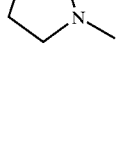 |  | Powder MS(m/z):500 (MH[+]) |
| 140 |  |  | Amorphous MS(m/z):499 (MH[+]) |

TABLE 7-continued

| Ex. No. | A N— | R¹ | Physiochemical properties |
|---|---|---|---|
| 141 | (2-hydroxymethyl-1-methylpyrrolidine) | propyl-N(CH₃)₂ | Amorphous MS(m/z):448 (MH⁺) |
| 142 | (2-hydroxymethyl-1-methylpyrrolidine) | propyl-(4-methylpiperazin-1-yl) | Amorphous MS(m/z):503 (MH⁺) |
| 143 | (2-hydroxymethyl-1-methylpyrrolidine) | propyl-NH-(pyridin-3-yl) | M.p. 112–114° C. |
| 144 | (2-hydroxymethyl-1-methylpyrrolidine) | propyl-NH-CH₂-(pyrimidin-2-yl) | Amorphous MS(m/z):512 (MH⁺) |
| 145 | (2-hydroxymethyl-1-methylpyrrolidine) | propyl-OH | M.p. 123–125° C. |

EXAMPLE 146

The corresponding starting compounds are treated in a similar manner to give the compound of the following formula as foam, MS (m/z): 464 (MH⁺).

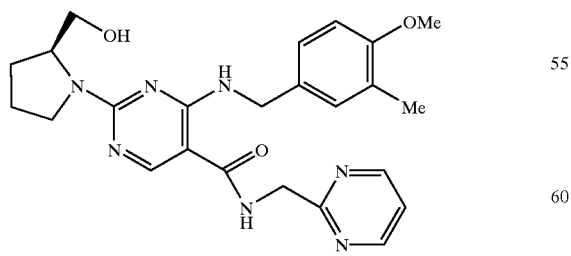

EXAMPLE 147

The corresponding starting compounds are treated in a similar manner to give the compound of the following formula, m.p. 140–144° C.

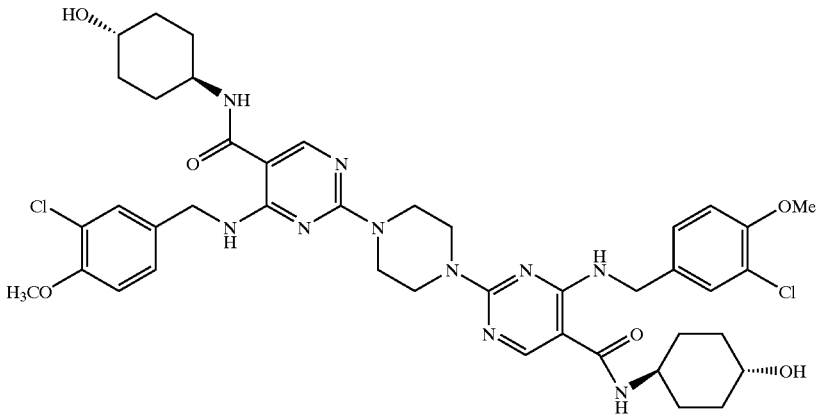

EXAMPLE 148

To a solution of (S)-2-(2-hydroxymethyl-1-pyrrolidinyl)-4-(3-chloro-4-methoxybenzylamino)-5-[N-(2-pyrimidylmethyl)carbamoyl]-pyrimidine (307 mg) obtained in Example 1-(5) in methylene chloride (6 ml) is added dropwise boron bromide (300 µl) under ice-cooling. The reaction mixture is stirred at 0° C. for 4 hours, and thereto is added methanol, and then a saturated aqueous sodium hydrogen carbonate solution under ice-cooling. The mixture is extracted with a mixture of ethyl acetate and tetrahydrofuran, and the organic layer is washed successively with water and brine. The mixture is dried over sodium sulfate, and concentrated under reduced pressure to give a slightly brown amorphous (227 mg). The resultant is suspended in chloroform, and the resulting insoluble materials are removed by filtration. The filtrate is subjected to silica gel column chromatography, and further purified by NH-silica gel column chromatography to give (S)-2-(2-hydroxymethyl-1-pyrrolidinyl)-4-(3-chloro-4-hydroxybenzylamino)-5-[N-(2-pyrimidylmethyl) carbamoyl]pyrimidine (129 mg) as a colorless foam, MS (m/z): 470 (MH$^+$), IR (Nujol): 3279, 1632, 1593, 1569, 1518, 1463 cm$^{-1}$.

EXAMPLE 149

(1) A suspension of 2-methylthio-4-(3-chloro-4-methoxybenzylamino)-5-ethoxycarbonylpyrimidine (2.00 g) obtained in Example 1 (1) in dimethylsulfoxide (10 ml) is treated with 10% aqueous sodium hydroxide solution (10 ml) at room temperature. To the reaction mixture is added dimethylsulfoxide (5 ml), and the mixture is stirred at room temperature overnight. To the resulting colorless solution is added citric acid until the solution becomes acidic. To the solution is added an excess amount of water (about 50 ml), and the resulting precipitates are collected by filtration. The precipitates are washed with isopropyl alcohol and isopropyl ether successively, and dried under reduced pressure to give 2-methylthio-4-(3-chloro-4-methoxybenzylamino)-5-carboxypyrimidine (1.864 g) as pale yellow impalpable powder, m.p. 238–240° C. (dec.).

(2) To a suspension of 4-(3-chloro-4-methoxybenzylamino)-5-carboxy-2-methylthiopyrimidine (200 mg) in methylene chloride (5 ml) are added oxalyl chloride (150 mg) and N,N-dimethylformamide, and the mixture is stirred at room temperature for 30 minutes, and concentrated. To a suspension of the resulting acid chloride compound and 5-aminopyrimidine (84.0 mg) in methylene chloride (5 ml) is added dimethylaminopyridine (144 mg) at room temperature, and the mixture is stirred at room temperature. To the mixture is poured water, and the mixture is extracted with ethyl acetate. The extract is washed with a saturated aqueous sodium hydrogen carbonate solution, water and brine, dried over sodium sulfate, and concentrated. The residue is triturated with a mixture of ethyl acetate and n-hexane to give 4-(3-chloro-4-methoxybenzylamino)-5-(5-pyrimidinylaminocarbonyl)-2-methylthiopyrimidine (216 mg) as pale yellow needles, m.p. 238–240° C., IR (Nujol): 3251, 1666 cm$^{-1}$, MS (m/z): 416 (M$^+$).

(3) To a suspension of the compound (150 mg) obtained in the above (2) in chloroform (10 ml) is added m-chloroperbenzoic acid (107 mg) at 0° C., and the mixture is stirred at 0° C. for one hour, and stirred at room temperature for one hour. To the mixture is added m-chloroperbenzoic acid (53 mg) at 0° C., and the mixture is stirred at 0° C. for 30 minutes. To the mixture are added L-prolinol (43.7 mg) and triethylamine (72.9 mg) at 0° C., and the mixture is stirred at room temperature for 20 hours. To the mixture is poured water, and the mixture is extracted with chloroform. The organic layer is washed with brine, dried over sodium sulfate, and concentrated under reduced pressure to give yellow viscous oil (201 mg), which is purified by NH-silica gel flash column chromatography (solvent; ethyl acetate), washed with a mixture of ethyl acetate and hexane to give (S)-4-(3-chloro-4-methoxybenzylamino)-5-(5-pyrimidinylaminocarbonyl)-2-(hydroxymethyl-1-pyrrolidinyl)pyrimidine (81 mg) as colorless needles, m.p. 192–195° C., IR (Nujol): 3279, 1669 cm$^{-1}$, MS (m/z): 470 (MH$^+$).

EXAMPLES 150–157

The corresponding starting compounds are treated in a similar manner as in Example 149 to give the compounds as listed in the following Table 8.

TABLE 8

| Ex. No. | (A N—) | R¹ | Physicochemical properties |
|---|---|---|---|
| 150 | pyrrolidinyl-CH(OH)- | -NH-(2-pyridyl) | Powder MS(m/z):469 (MH+) |
| 151 | pyrrolidinyl-CH(OH)- | -NH-(2-pyrimidinyl) | Powder MS(m/z):470 (MH+) |
| 152 | pyrrolidinyl-CH(OH)- | -NH-(4-pyrimidinyl) | M.p. 182–185° C. |
| 153 | pyrrolidinyl-CH(OH)- | -NH-(pyrimidinyl) | M.p. 176–178° C. |
| 154 | pyrrolidinyl-CH(OH)- | -NH-(3,4-dimethylisoxazol-5-yl) | Powder MS(m/z):487 (MH+) |
| 155 | pyrrolidinyl-CH(OH)- | -NH-(4,6-dimethyl-2-pyridyl) | M.p. 161–163° C. |
| 156 | pyrrolidinyl-CH(OH)- | -NH-(4,6-dimethyl-1-oxide-2-pyridyl) | Powder MS(m/z):513 (MH+) |
| 157 | pyrrolidinyl-CH(OH)- | -NH-(4,6-dimethyl-2-pyrimidinyl) | Powder MS(m/z):498 (MH+) |

EXAMPLE 158

(1) A suspension of 4-(3-chloro-4-methoxybenzylamino)-5-carboxy-2-methylthiopyrimidine (154.0 mg) obtained in Example 149 (1) in methylene chloride (5 ml) is treated with oxalyl chloride (119 μl) at room temperature, and thereto is added N,N-dimethylformamide. The mixture is stirred for one hour, and the solvent is evaporated under reduced pressure. The residue is treated with ether, and kept in a refrigerator overnight. The volatile materials are removed under reduced pressure, and the residue is treated with an excess amount of diazomethane at 0° C. and kept in a refrigerator overnight. The reaction is quenched with methanol, and the mixture is purified by silica gel chromatography (solvent; hexane:ethyl acetate= 2:1) to give 4-(3-chloro-4-methoxybenzylamino)-5-(diazomethylcarbonyl)-2-methylthiopyrimidine (21.5 mg) as pale yellow solid, IR (Nujol): 3277, 2115, 1607, 1567, 1461, 1377, 1357, 1141 cm¹, MS (m/z): 364 (MH+), m.p. 162–165° C. (dec.).

(2) A suspension of the compound obtained in the above (1) (16.5 mg) in methanol (3 ml) is treated with toluenesulfonic acid monohydrate (16.5 mg) at room temperature. The solvent is evaporated under reduced pressure, and the residue is purified by preparative TLC (solvent; hexane:ethyl acetate=2:1) to give 4-(3-chloro-4-methoxybenzylamino)-5-(methoxymethylcarbonyl)-2-methylthiopyrimidine (11.0 mg) as colorless oil.

(3) A solution of the compound (11.0 mg) obtained in the above (2) in chloroform (1 ml) is treated with m-chloroperbenzoic acid (7.4 mg) at 0° C. The mixture is treated with triethylamine (8.3 μl) and L-prolinol (36 mg) at room temperature, and the reaction mixture is stirred overnight. The reaction mixture is diluted with ethyl acetate, washed with a saturated aqueous sodium hydrogen carbonate solution and a saturated aqueous sodium chloride solution, and dried over sodium sulfate. The residue is purified by preparative TLC (solvent; chloroform:ethyl acetate 1:1) to give (S)-4-(3-chloro-4-methoxybenzylamino)-5-(methoxymethylcarbonyl)-2-(2-hydroxymethyl-1-pyrrolidinyl)pyrimidine (8.5 mg) as colorless oil, MS (m/z): 421 (MH+).

Industrial Applicability

The compound (I) of the present invention and a pharmaceutically acceptable salt thereof exhibit excellent PDE V inhibitory activities, and they are useful pharmaceutical compounds for the prophylaxis or treatment of penile erectile dysfunction, etc.

What is claimed is:

1. An aromatic nitrogen-containing 6-membered cyclic compound of the formula (I):

(I)

wherein Ring A is a substituted or unsubstituted nitrogen-containing heterocyclic group; $R^1$ is a substituted or unsubstituted lower alkyl group, a group of the formula: —NH—Q—$R^3$ (in which $R^3$ is a substituted or unsubstituted nitrogen containing heterocyclic group, and Q is a lower alkylene group or a single bond), or a group of the formula: —NH—$R^4$ (in which $R^4$ is a substituted or unsubstituted cycloalkyl group); R² is a substituted or unsubstituted aryl group; Z is a group of the formula: =CH—, and Y is a group of the formula: =N—, or a pharmaceutically acceptable salt thereof.

2. The compound according to claim 1, wherein the nitrogen-containing heterocyclic group of the "substituted or unsubstituted nitrogen-containing heterocyclic group" for Ring A is a 5- or 6-membered nitrogen-containing heteromonocyclic group or a 8- to 10-membered nitrogen-containing heterobicyclic group, and the substituent of the above "substituted or unsubstituted nitrogen-containing heterocyclic group" is selected from the group consisting of (1) a lower alkyl group, (2) a hydroxy-substituted lower alkyl group, (3) a formyl group, (4) an oxo group, (5) an amino group, (6) a hydroxy group, (7) a lower alkoxycarbonyl group, and (8) a pyrimidinyl group substituted by (i) a benzylamino group substituted by a halogen atom and a lower alkoxy group, and (ii) a cycloalkylcarbamoyl group substituted by a hydroxy group, R¹ is a lower alkyl group which may optionally be substituted by a group selected from the group consisting of a lower alkoxy group, a hydroxy group, a morpholinyl group, a lower alkylsulfonyl group, a di-(lower alkyl)phosphino group, a di-(lower alkyl)amino group, a pyrimidinyl-substituted lower alkylamino group, a pyridyl group, a pyridylamino group and a lower alkyl-substituted piperazinyl group, a group of the formula: —NH—Q—R³, or a group of the formula: —NH—R⁴, the nitrogen-containing heterocyclic group of the "substituted or unsubstituted nitrogen-containing heterocyclic group" for R³ is a 5- or 6-membered nitrogen-containing heteromonocyclic group or a 8- to 10-membered nitrogen-containing heterobicyclic group, and the substituent of the above "substituted or unsubstituted nitrogen-containing heterocyclic group" is selected from the group consisting of a lower alkyl group, a hydroxy-substituted lower alkyl group, an oxo group, an amino group, a di-(lower alkyl)amino group, a lower alkanoyl group and a cyano-substituted lower alkyl group, R⁴ is a cycloalkyl group being substituted by a group selected from the group consisting of hydroxy group, a lower alkoxy group and a pyrimidinyloxy group, R² is a phenyl group being substituted by a group selected from the group consisting of a lower alkoxy group, a halogen atom, a cyano group, a nitro group, a hydroxy group and a lower alkyl group.

3. The compound according to claim 2, wherein the nitrogen-containing heterocyclic group of the "substituted or unsubstituted nitrogen-containing heterocyclic group" for Ring A is a 5- or 6-membered nitrogen-containing heteromonocyclic group of the formula:

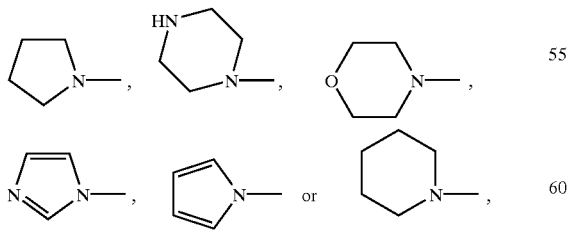

or a nitrogen-containing heterobicyclic group of the following formula wherein the above-mentioned 5- or 6-membered nitrogen-containing heteromonocyclic group and a 5- or 6-membered cyclic group are fused:

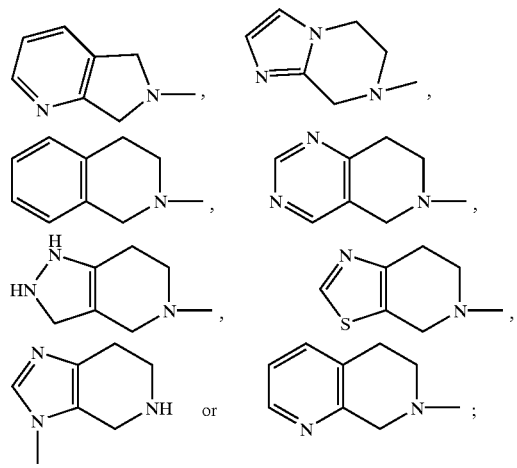

and the nitrogen-containing heterocyclic group of the "substituted or unsubstituted nitrogen-containing heterocyclic group" for R³ is a nonaromatic nitrogen-containing heteromonocyclic group of the formula:

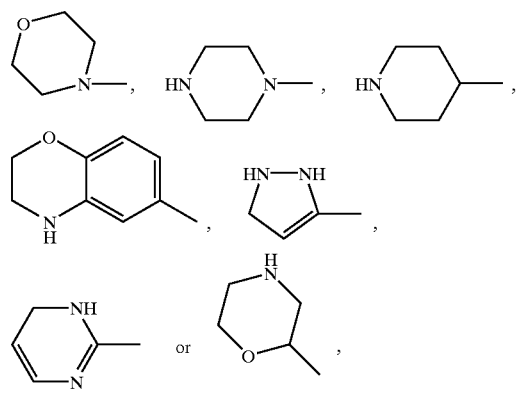

or an aromatic nitrogen-containing heterocyclic group of the formula:

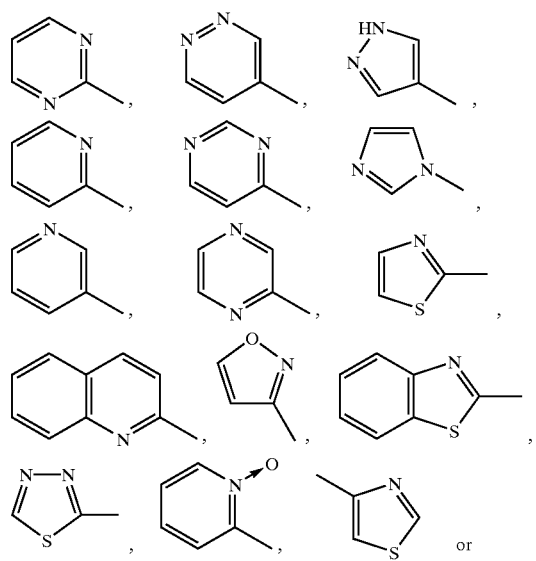

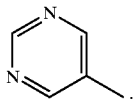

or a pharmaceutically acceptable salt thereof.

4. The compound according to claim 1, wherein the nitrogen-containing heterocyclic group of the "substituted or unsubstituted nitrogen-containing heterocyclic group" for Ring A is a 5- or 6-membered nitrogen-containing heteromonocyclic group or a 8- to 10-membered nitrogen-containing heterobicyclic group, and the substituent of the above "substituted or unsubstituted nitrogen-containing heterocyclic group" is selected from the group consisting of a lower alkyl group, a hydroxy-substituted lower alkyl group, a formyl group and an oxo group, $R^1$ is a lower alkyl group which may optionally be substituted by a group selected from the group consisting of a lower alkoxy group and a morpholinyl group, a group of the formula: —NH—Q—$R^3$, or a group of the formula: —NH—$R^4$, the "substituted or unsubstituted nitrogen-containing heterocyclic group" for $R^3$ is a 5- or 6-membered nitrogen-containing heteromonocyclic group which may optionally be substituted by a lower alkyl group, $R^4$ is a cycloalkyl group being substituted by a group selected from the group consisting of hydroxy group and a lower alkoxy group, $R^2$ is a phenyl group being substituted by a group selected from the group consisting of a lower alkoxy group, a halogen atom and a cyano group.

5. The compound according to claim 4, wherein the nitrogen-containing heterocyclic group of the "substituted or unsubstituted nitrogen-containing heterocyclic group" for Ring A is a 5- or 6-membered non-aromatic nitrogen-containing heteromonocyclic group of the formula:

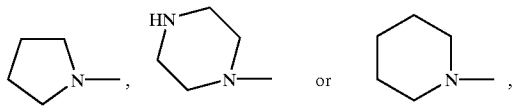

or a nitrogen-containing heterobicyclic group of the following formula wherein the above-mentioned 5- or 6-membered non-aromatic nitrogen-containing heteromonocyclic group and a 5- or 6-membered aromatic nitrogen-containing heteromonocyclic group are fused:

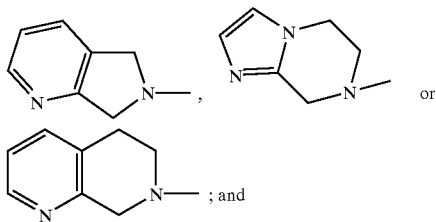

the nitrogen-containing heterocyclic group of the "substituted or unsubstituted nitrogen-containing heterocyclic group" for $R^3$ is a non-aromatic nitrogen-containing heteromonocyclic group of the formula:

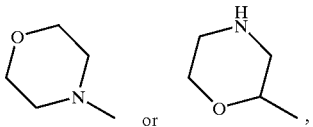

or an aromatic nitrogen-containing heteromonocyclic group of the formula:

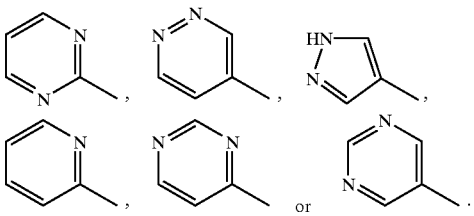

6. The compound according to claim 1, wherein Ring A is a group of the formula:

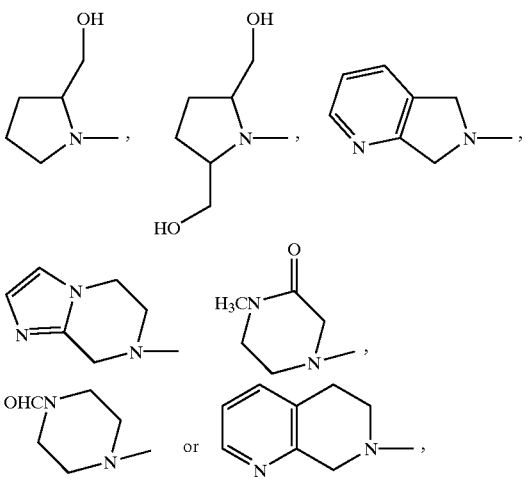

$R^1$ is a lower alkyl group, a lower alkoxy-substituted lower alkyl group, a morpholinyl-substituted lower alkyl group, a group of the formula: —NH—Q—$R^3$, or a group of the formula: —NH—$R^4$, $R^3$ is a group of the formula:

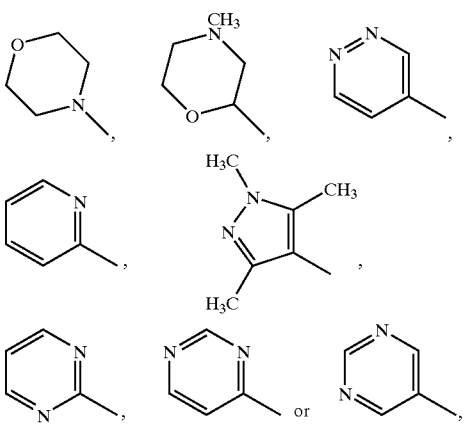

$R^4$ is a group of the formula:

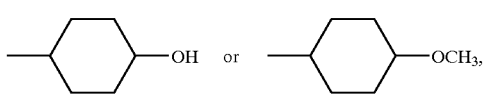

and $R^2$ is a group of the formula:

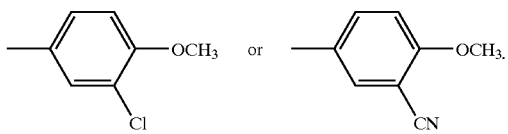

7. The compound according to claim 1, wherein the nitrogen-containing heterocyclic group of the "substituted or unsubstituted nitrogen-containing heterocyclic group" for Ring A is a 5- or 6-membered nitrogen-containing heteromonocyclic group or a 8- to 10-membered nitrogen-containing heterobicyclic group, and the substituent of the above "substituted or unsubstituted nitrogen-containing heterocyclic group" is a group selected from the group consisting of a lower alkyl group, a hydroxy-substituted lower alkyl group, a formyl group and an oxo group, $R^1$ is a lower alkoxy-substituted lower alkyl group, a group of the formula: —NH—Q—$R^3$, or a group of the formula: —NH—$R^4$, the "substituted or unsubstituted nitrogen-containing heterocyclic group" for $R^3$ is a 5- or 6-membered nitrogen-containing heteromonocyclic group which may optionally be substituted by a lower alkyl group, $R^4$ is a hydroxy-substituted cycloalkyl group, and $R^2$ is a phenyl group being substituted by a group selected from the group consisting of a lower alkoxy group and a halogen atom.

8. The compound according to claim 7, wherein the nitrogen-containing heterocyclic group of the "substituted or unsubstituted nitrogen-containing heterocyclic group" for Ring A is a 5- or 6-membered non-aromatic nitrogen-containing heteromonocyclic group of the formula:

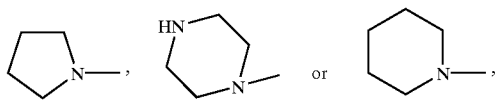

a group of the formula:

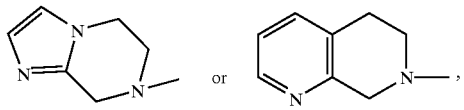

the nitrogen-containing heterocyclic group of the "substituted or unsubstituted nitrogen-containing heterocyclic group" for $R^3$ is a non-aromatic nitrogen-containing heteromonocyclic group of the formula:

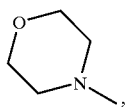

or an aromatic nitrogen-containing heteromonocyclic group of the formula:

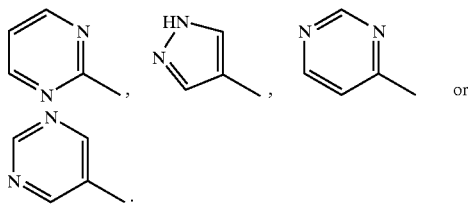

9. The compound according to claim 1, wherein Ring A is a group of the formula:

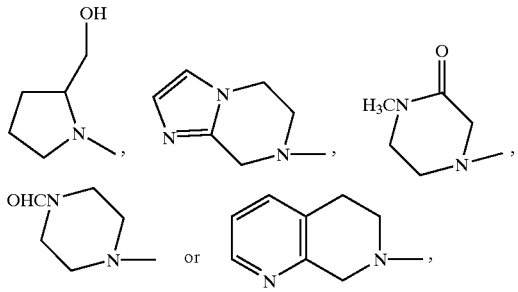

$R^1$ is a lower alkoxy-substituted lower alkyl group, a group of the formula: —NH—Q—$R^3$, or a group of the formula: —NH—$R^4$, $R^3$ is a group of the formula:

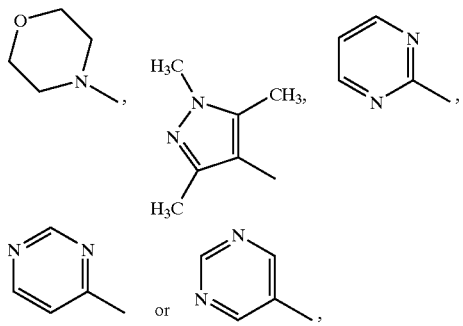

$R^4$ is a group of the formula:

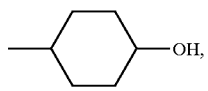

and $R^2$ is a group of the formula:

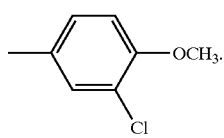

10. The compound according to claim 1, wherein the nitrogen-containing heterocyclic group of the "substituted or unsubstituted nitrogen-containing heterocyclic group" for Ring A is a 5- or 6-membered nitrogen-containing heteromonocyclic group or a 8- to 10-membered nitrogen-containing heterobicyclic group, and the substituent of the above "substituted or unsubstituted nitrogen-containing heterocyclic group" is a hydroxy-substituted lower alkyl group, $R^1$ is a group of the formula: —NH—Q—$R^3$, the "substituted or unsubstituted nitrogen-containing heterocyclic group" for R³ is a 5- or 6-membered nitrogen-containing heteromonocyclic group which may optionally be substituted by a lower alkyl group, and R² is a phenyl group being substituted by a group selected from the group consisting of a lower alkoxy group and a halogen atom.

11. The compound according to claim 10, wherein the nitrogen-containing heterocyclic group of the "substituted or unsubstituted nitrogen-containing heterocyclic group" for Ring A is a 5- or 6-membered non-aromatic nitrogen-containing heteromonocyclic group of the formula:

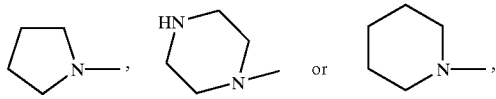

or a group of the formula:

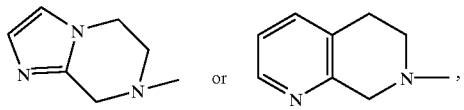

the nitrogen-containing heterocyclic group of the "substituted or unsubstituted nitrogen-containing heterocyclic group" for R³ is a non-aromatic nitrogen-containing heteromonocyclic group of the formula:

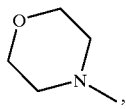

or an aromatic nitrogen-containing heteromonocyclic group of the formula:

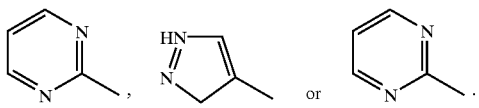

12. The compound according to claim 1, wherein Ring A is a group of the formula:

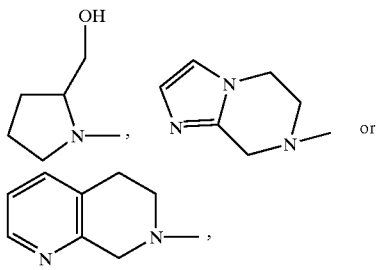

R¹ is a group of the formula: —NH—Q—R³, R³ is a group of the formula:

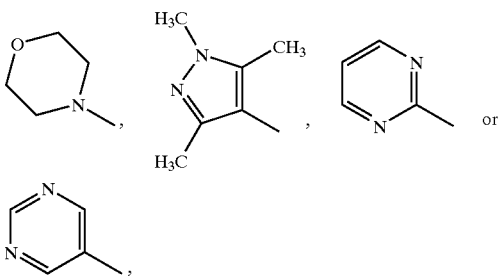

and R² is a group of the formula:

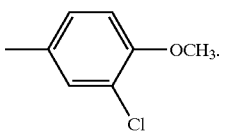

13. The compound according to claim 1, wherein said compound is selected from the group consisting of:

(S)-2-(2-hydroxymethyl-1-pyrrolidinyl)-4-(3-chloro-4-methoxybenzylamino)-5-[N-(2-pyrimidinylmethyl)carbamoyl]pyrimidime;

2-(6,7-dihydro-5H-pyrrolo[3,4-b]pyridin-6-yl)-4-(3-cyano-4-methoxybenzylamino)-5-[N-(2-pyrimidinylmethyl)carbamoyl]pyrimidine;

2-(5,6,7,8-tetrahydroimidazo[1,2-a]pyrazin-7-yl)-4-(3-chloro-4-methoxybenzylamino)-5-[N-(trans-4-methoxycyclohexyl)carbamoyl]pyrimidine;

2-(6,7-dihydro-5H-pyrrolo[3,4-b]pyridin-6-yl)-4-(3-cyano-4-methoxybenzylamino)-5-[N-(trans-4-hydroxycyclohexyl)carbamoyl]pyrimidine;

2-(6,7-dihydro-5H-pyrrolo[3,4-b]pyridin-6-yl)-4-(3-cyano-4-methoxybenzylamino)-5-[N-(2-morpholinoethyl)carbamoyl]pyrimidine;

(S)-2-(2-hydroxymethyl-1-pyrrolidinyl)4-(3-chloro-4-methoxy-benzylamino)-5-[N-(2-morpholinoethyl)carbamoyl]pyrimidine;

2-[(2S)-2-hydroxymethyl-1-pyrrolidinyl]-4-(3-chloro-4-methoxy-benzylamino)-5-[N-[[(2R)-4-methyl-2-morpholinyl]methyl]carbamoyl]pyrimidine;

2-[(2S)-2-hydroxymethyl-1-pyrrolidinyl]-4-(3-chloro-4-methoxy-benzylamino)-5-[N-[[(2S)-4-methyl-2-morpholinyl]methyl]carbamoyl]pyrimidine;

(S)-2-(2-hydroxymethyl-1-pyrrolidinyl)-4-(3-chloro-4-methoxy-benzylamino)-5-[N-(4-pyrimidinylmethyl)carbamoyl]pyrimidine;

2-(4-methyl-3-oxo-I-piperazinyl)-4-(3-chloro-4-methoxybenzyl-amino)-5-[N-(trans-4-hydroxycyclohexyl)carbamoyl]pyrimidine;

2-(4-formyl-1-piperazinyl)-4-(3-chloro-4-methoxybenzylamino)-5-[N-(trans-4-hydroxycyclohexyl)carbamoyl]pyrimidine;

2-(5,6,7,8-tetrahydroimidazo[1,2-a]pyrazin-7-yl)-4-(3-chloro-4-methoxybenzylamino)-5-[N-(trans-4-hydroxycyclohexyl)carbamoyl]pyrimidine;

2-[cis-2,5-bis(hydroxymethyl)-1-pyrrolidinyl]-4-(3-chloro-4-methoxybenzylamino)-5-[N-(2-pyrimidinylmethyl)carbamoyl]pyrimidine, 2-(5,6,7,8-tetrahydroimidazo[1,2-a]pyrazin-7-yl)-4-(3-chloro-4-methoxy-benzylamino)-5-[N-(2-pyrimidinylmethyl)carbamoyl]pyrimidine;

2-(5,6,7,8-tetrahydroimidazo[1,2-a]pyrazin-7-yl)-4-(3-chloro-4-methoxy-benzylamino)-5-[N-(2-morpholinoethyl)carbamoyl]pyrimidine;

2-(5,6,7,8-tetrahydro-1,7-naphthyridin-7-yl)-4-(3-chloro-4-methoxybenzylamino)-5-[N-(2-morpholinoethyl)carbamoyl]pyrimidine;

(S)-2-(2-hydroxymethyl-1-pyrrolidinyl)-4-(3-chloro-4-methoxybenzylamino)-5-acethylpyrimidine;

(S)-2-(2-hydroxymethyl-1-pyrrolidinyl)-4-(3-chloro-4-methoxybenzylamino)-5-[N-(4-pyridazinylmethyl)carbamoyl]pyrimidine;

(S)-2-(2-hydroxymethyl-1-pyrrolidinyl)-4-(3-chloro-4-methoxybenzylamino)-5-[N-(5-pyridazinylmethyl)carbamoyl]pyrimidine;

(S)-2-(2-hydroxymethyl-1-pyrrolidinyl)-4-(3-chloro-4-methoxybenzylamino)-5-[N-(2-pyrimidinylmethyl)carbamoyl]pyrimidine;

(S)-2-(2-hydroxymethyl-1-pyrrolidinyl)-4-(3-chloro-4-methoxybenzylamino)-5-[N-(2-morpholinoethyl)carbamoyl]pyrimidine;

2-(5,6,7,8-tetrahydroimidazo[1,2-a]pyrazin-7-yl)-4-(3-chloro-4-methoxy-benzylamino)-5-[N-[(4-methyl-2-morpholinyl)methyl]carbamoyl]pyrimidine;

(S)-2-(2-hydroxymethyl-1-pyrrolidinyl)-4-(3-chloro-4-methoxybenzylamino)-5-[(2-methoxyethyl)carbonyl]pyrimidine; and (S)-2-(2-hydroxymethyl-1-pyrrolidinyl)-4-(3-chloro-4-methoxybenzylamino)-5-[N-(1,3,5-trimethyl-4-pyrazolyl)carbamoyl]pyrimidine, or a pharmaceutically acceptable salt thereof.

14. The compound according to claim 13, wherein said compound is selected from the group consisting of:

(S)-2-(2-hydroxymethyl-1-pyrrolidinyl)-4-(3-chloro-4-methoxybenzylamino)-5-[N-(2-pyrimidinylmethyl)carbamoyl]pyrimidine;

(S)-2-(2-hydroxymethyl-1-pyrrolidinyl)-4-(3-chloro-4-methoxybenzylamino)5-[N-(4-pyrimidinylmethyl)carbamoyl]pyrimidine;

2-(4-methyl-3-oxo-1-piperazinyl)-4-(3-chloro-4-methoxybenzylamino)-5-[N-(trans-4-hydroxycyclohexyl)carbamoyl]pyrimidine;

2-(4-formyl-1-piperazinyl)-4-(3-chloro-4-methoxybenzylamino)-5-[N-(trans-4-hydroxycyclohexyl)carbamoyl]pyrimidine;

2-(5,6,7,8-tetrahydroimidazo[1,2-a]pyrazin-7-yl)-4-(3-chloro-4-methoxy-benzylamino)-5-[N-(2-pyrimidinylmethyl)carbamoyl]pyrimidine;

2-(5,6,7,8-tetrahydroimidazo[1,2-a]pyrazin-7-yl)-4-(3-chloro-4-methoxy-benzylamino)-5-[N-(2-morpholinoethyl)carbamoyl]pyrimidine;

2-(5,6,7,8-tetrahydro-1,7-naphthyridin-7-yl)-4-(3-chloro-4-methoxybenzylamino)5-[N-(2-morpholinoethyl)carbamoyl]pyrimidine;

(S)-2-(2-hydroxymethyl-1-pyrrolidinyl)-4-(3-chloro-4-methoxybenzylamino)-5-[N-pyrimidinylmethyl)carbamoyl]pyrimidine;

(S)-2-(2-hydroxymethyl-1-pyrrolidinyl)-4-(3-chloro-4-methoxybenzylamino)-5-[(2-methoxyethyl)carbonyl]pyrimidine; and (S)-2-(2-hydroxymethyl-1-pyrrolidinyl)-4-(3-chloro-4-methoxy-benzylamino)-5-[N-(1,3,5-trimethyl-4-pyrazolyl)carbamoyl]pyrimidine, or a pharmaceutically acceptable salt thereof.

15. The compound according to claim 13, wherein said compound is selected from the group consisting of:

(S)-2-(2-hydroxymethyl-1-pyrrolidinyl)-4-(3-chloro-4methoxybenzylamino)-5-[N-(2-pyrimidinylmethyl)carbamoyl]pyrimidine;

(S)-2-(2-hydroxymethyl-1-pyrrolidinyl)-4-(3-chloro-4-methoxybenzylamino)-5-[N-(2-morpholinoethyl)carbamoyl]pyrimidine;

2-(5,6,7,8-tetrahydroimidazo[1,2-a]pyrazin-7-yl)-4-(3-chloro-4-methoxybenzylamino)-5-[N-(2-pyrimidinylmethyl)carbamoyl]pyrimidine;

2-(5,6,7,8-tetrahydro-1,7-naphthyridin-7-yl)-4-(3-chloro-4-methoxybenzylamino)-5-[N-(2-morpholinoethyl)carbamoyl]pyrimidine;

(S)-2-(2-hydroxymethyl-1-pyrrolidinyl)-4-(3-chloro-4-methoxybenzylamino)-5[N-(5-pyrimidinylmethyl)carbamoyl]pyrimidine; and (S)-2-(2-hydroxymethyl-1-pyrrolidinyl)-4-(3-chloro-4-methoxybenzylamino)-5-[N-(1,3,5-trimethyl-4-pyrazolyl)carbamoyl]pyrimidine, or a pharmaceutically acceptable salt thereof.

16. The compound of claim 13, wherein said compound is (S)-2-(2-hydroxymethyl-1-pyrrolidinyl)-4-(3-chloro-4-methoxybenzylamino)-5-[N-(2-pyrimidinylmethyl)carbamoyl]pyrimidine, or a pharmaceutically acceptable salt thereof.

17. The compound of claim 13, wherein said compound is 2-(5,6,7,8-tetrahydro-1,7-naphthyridin-7-yl)-4-(3-chloro-4-methoxybenzylamino)-5-[N-(2-morpholinoethyl)carbamoyl]pyrimidine, or a pharmaceutically acceptable salt thereof.

18. The compound of claim 13, wherein said compound is (S)-2-(2-hydroxymethyl-1-pyrrolidinyl)-4-(3-chloro-4-methoxybenzylamino)-5-[N-(1,3,5-trimethyl-4-pyrazolyl)carbamoyl]pyrimidine, or a pharmaceutically acceptable salt thereof.

19. A pharmaceutical composition, which contains as an active ingredient the compound as set forth in any one of claims 1–12 and 13–18, or a pharmaceutically acceptable salt thereof and a pharmaceutically acceptable carrier therefor.

20. A method for treatment of penile erectile dysfunction, which comprises administering to a patient in need thereof an effective amount of the compound as set forth in any one of claims 1–12 and 13–18, or a pharmaceutically acceptable salt thereof.

21. A method for treatment of pulmonary hypertension, which comprises administering to a patient in need thereof an effective amount of the compound as set forth in any one of claims 1–12 and 13–18, or a pharmaceutically acceptable salt thereof.

22. A method for treatment of diabetic gastroparesis, which comprises administering to a patient in need thereof an effective amount of the compound as set forth in any one of claims 1–12 and 13–18, or a pharmaceutically acceptable salt thereof.

* * * * *

UNITED STATES PATENT AND TRADEMARK OFFICE
CERTIFICATE OF CORRECTION

PATENT NO.   : 6,656,935 B2  
DATED        : December 2, 2003  
INVENTOR(S)  : Koichiro Yamada et al.

It is certified that error appears in the above-identified patent and that said Letters Patent is hereby corrected as shown below:

Column 76,
Lines 51-60, in the structure for formula (I):

should read 

Column 79,
Line 5, after the structure 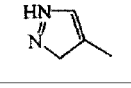 delete the period.

Column 81,
Line 47, before "a group", insert -- or --.

Column 83,
Lines 43-47, 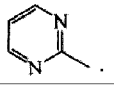 should read 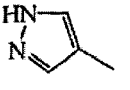

Column 84,
Lines 24-26, "(S)-2-(2-hydroxymethyl-1-pyrrolidinyl)-4-(3-chloro-4-methoxybenzylamino)-5-[N-(2-pyrimidinylmethyl)carbamoyl]pyrimidime;" should read -- (S)-2-(2-hydroxymethyl-1-pyrrolidinyl)-4-(3-chloro-4-methoxybenzylamino)-5-[N-(2-pyrimidinylmethyl)carbamoyl]pyrimidine; --.
Lines 40-42, "(S)-2-(2-hydroxymethyl-1-pyrrolidinyl)4-(chloro-4-methoxybenzylamino)-5-[N-(2-morpholinoethyl)carbamoyl]pyrimidine;" should read -- (S)-2-(hydroxymethyl-1-pyrrolidinyl)-4-methoxybenzylamino)-5-[N-(2-morpholinoethyl)carbamoyl]pyrimidine; --.
Lines 43-45, "2-[(2S)-2-hydroxymethyl-1-pyrrolidinyl]-4-(3-chloro-4-methoxybenzylamino)-5-[N-[[(2R)-4-methyl-2-morpholinyl]methyl]carbamoyl]pyrimidine;" should read -- 2-[(2S)-2-hydroxymethyl-1-pyrrolidinyl]-4-(3-chloro-4-methoxybenzylamino)-5-[N-[[(2R)-4-methyl-2-morpholinyl]methyl]carbamoyl]pyrimidine; --
Lines 46-48, "2-[(2S)-2-hydroxymethyl-1-pyrrolidinyl]-4-(3-chloro-4-methoxybenzylamino)-5-[N-[[(2S)-4-methyl-2-morpholinyl]methyl]carbamoyl]pyrimidine;" should read -- 2-[(2S)-2-hydroxymethyl-1-pyrrolidinyl]-4-(3-chloro-4-methoxybenzylamino)-5-[N-[[(2S)-4-methyl-2-morpholinyl]methyl]carbamoyl]pyrimidine; --
Lines 49-51, "(S)-2-(2-hydroxymethyl-1-pyrrolidinyl)-4-(3-chloro-4-methoxybenzylamino)-5-[N-pyrimidinylmethyl)carbamoyl]pyrimidine;" should read -- (S)-2-(2-hydroxymethyl-1-pyrrolidinyl)-4-(3-chloro-4-methoxybenzylamino)-5-[N-(pyrimidinylmethyl)carbamoyl]pyrimidine; --

UNITED STATES PATENT AND TRADEMARK OFFICE
CERTIFICATE OF CORRECTION

PATENT NO. : 6,656,935 B2
DATED : December 2, 2003
INVENTOR(S) : Koichiro Yamada et al.

It is certified that error appears in the above-identified patent and that said Letters Patent is hereby corrected as shown below:

Column 84 (cont'd),
Lines 52-54, "2-(4methyl-3-oxo-I-piperazinyl)-4-(3-chloro-4-methoxybenzyl-amino)-5-[N-(trans-4-hydroxycyclohexyl)carbamoyl]pyrimidine;" should read -- 2-(4methyl-3-oxo-1-piperazinyl)-4-(3-chloro-4-methoxybenzyl-amino)-5-[N-(trans-4-hydroxycyclohexyl)carbamoyl]pyrimidine; --
Line 64, replace the comma "," with a semicolon -- ; --.
Lines 65-67, "2-(5,6,7,8-tetrahydroimidazo[1,2-a]pyrazin-7-yl)-4-(3-chloro-4-methoxy-benzylamino)-5-[N-(2-pyrimidinylmethyl)carbamoyl]pyrimidine;" should read -- 2-(5,6,7,8-tetrahydroimidazo[1,2-a]pyrazin-7-yl)-4-(3chloro-4-methoxybenzylamino)-5-[N-(2-pyrimidinylmethyl)carbamoyl]pyrimidine; --.

Column 85,
Lines 1-3, "2-(5,6,7,8-tetrahydroimidazo[1,2-a]pyrazin-7-yl)-4-(3-chloro-4-methoxy-benzylamino)-5-[N-2-morpholinoethyl)carbamoyl]pyrimidine;" should read -- 2-(5,6,7,8-tetrahydroimidazo[1,2-a]pyrazin-7-yl)-4-(3-chloro-4-methoxybenzylamino)-5-[N-2-morpholinoethyl)carbamoyl]pyrimidine; --.
Lines 13-15, "(S)-2-(2-hydroxymethyl-1-pyrrolidinyl)-4-(3-chloro-4-methoxybenzylamino)-5-[N-(5-pyridazinylmethyl)carbamoyl]pyrimidine;" should read -- (S)-2-(2-hydroxymethyl-1-pyrrolidinyl)-4-(3-chloro-4-methoxybenzylamino)-5-[N-(5-pyrimidinylmethyl)carbamoyl]pyrimidine; --
Lines 16-18, "(S)-2-(hydroxymethyl-1-pyrrolidinyl)-4-(3-chloro-4-methoxybenzylamino)-5-[N-(2-pyrimidinylmethyl)carbomoyl]pyrimidine;" should read -- (S)-2-(hydroxymethyl-1-pyrrolidinyl)-4-(3-chloro-4-methoxybenzylamino)-5-[N-(2-pyridylmethyl)carbomoyl]pyrimidine; --.
Lines 19-21, "(S)-2-(2-hydroxymethyl-1-pyrrolidiny)-4-(3-chloro-4-methoxybenzylamino)-5-[N-(2-morpholinoethyl)carbamoyl]pyrimidine;" should read -- (S)-2-(2-hydroxymethyl-1-pyrrolidiny)-4-(3-chloro-4-methoxybenzylamino)-5-[(2-morpholinoethyl)carbonoy]pyrimidine; --.
Lines 22-24, "2-(5,6,7,8-tetrahydroimidazo[1,2-a]pyrazin-7-yl)-4-(3-chloro-4-methoxy-benzylamino)-5-[N-[(4-methyl-2-morpholiny)methyl]pyrimidine;" should read -- 2-(5,6,7,8-tetrahydroimidazo[1,2-a]pyrazin-7-yl)-4-(3-chloro-4-methoxybenzylamino)-5-[N-[(4-methyl-2-morpholiny)methyl]pyrimidine; --
Lines 38-40, "(S)-2-(2-hydroxymethyl-1-pyrrolidinyl)-4-(3-chloro-4-methoxybenzylamino) 5-[N-(4-pyrimidinylmethyl)carbamoyl]pyrimidine;" should read -- (S)-2-(2-hydroxymethyl-1-pyrrolidinyl)-4-(3-chloro-4-methoxybenzylamino)-5-[N-(4-pyrimidinylmethyl)carbamoyl]pyrimidine; --.
Lines 48-50, "2-(5,6,7,8-tetrahydroimidazo[1,2-a]pyrazin-7-yl)-4-(3-chloro-4-methoxy-benzylamino)-5-[N-(2-pyrimidinylmethyl)carbamoyl]pyrimidine;" should read -- 2-(5,6,7,8-tetrahydroimidazo[1,2-a]pyrazin-7-yl)-4-(3-chloro-4-methoxybenzylamino)-5-[N-(2-pyrimidinylmethyl)carbamoyl]pyrimidine; --.

UNITED STATES PATENT AND TRADEMARK OFFICE
CERTIFICATE OF CORRECTION

PATENT NO. : 6,656,935 B2
DATED : December 2, 2003
INVENTOR(S) : Koichiro Yamada et al.

It is certified that error appears in the above-identified patent and that said Letters Patent is hereby corrected as shown below:

Column 85 (cont'd),
Lines 51-53, "2-(5,6,7,8-tetrahydroimidazo[1-2-a]pyrazine-7-yl)-4-(3-chloro-4-methoxy-benzylamino)-5-[N-(2-morpholinoethyl)carbamoyl]pyridine;" should read -- 2-(5,6,7,8-tetrahydroimidazo[1-2-a]pyrazine-7-yl)-4-(3-chloro-4-methoxybenzylamino)-5-[N-(2-morpholinoethyl)carbamoyl]pyridine; --.
Lines 54-56, "2-(5,6,7,8-tetrahydro-1,7-naphthyridin-7-yl)-4-(3-chloro-4-methoxybenzylamino)5-[N-(2-morpholinoethyl)carbamoyl]pyrimidine;" should read -- 2-(5,6,7,8-tetrahydro-1,7-naphthyridin-7-yl)-4-(3-chloro-4-methoxybenzylamino)-5-[N-(2-morpholinoethyl)carbamoyl]pyrimidine; --.
Lines 57-59, "(S)-2-(2-hydroxymethyl-1-pyrrolidinyl)-4-(3-chloro-4-methoxybenzylamino)-5-[N-pyridinylmethyl)carbamoyl]pyrimidine;" should read -- (S)-2-(2-hydroxymethyl-1-pyrrolidinyl)-4-(3-chloro-4-methoxybenzylamino)-5-[N-(5-pyridinylmethyl)carbamoyl]pyrimidine; --.

Column 86,
Lines 1-3, "(S)-2-(2-hydroxymethyl-1-pyrrolidinyl)-4-(3-chloro-4-methoxy-benzylamino)-5-[N-(1,3,5-trimethyl-4-pyrazolyl)carbamoyl]pyrimidine;" should read -- (S)-2-(2-hydroxymethyl-1-pyrrolidinyl)-4-(3-chloro-4-methoxybenzylamino)-5-[N-(1,3,5-trimethyl-4-pyrazolyl)carbamoyl]pyrimidine, --.
Lines 19-21, "(S)-2-(2-hydroxymethyl-1-pyrrolidinyl)-4-(3-chloro-4-methoxybenzylamino)-5[N-(5-pyrimidinylmethyl)carbamoyl]pyrimidine;" should read -- (S)-2-(2-hydroxymethyl-1-pyrrolidinyl)-4-(3-chloro-4-methoxybenzylamino)-5-[N-(5-pyrimidinylmethyl)carbamoyl]pyrimidine; --.

Signed and Sealed this

Twenty-eighth Day of September, 2004

JON W. DUDAS
*Director of the United States Patent and Trademark Office*

UNITED STATES PATENT AND TRADEMARK OFFICE
CERTIFICATE OF CORRECTION

PATENT NO. : 6,656,935 B2
DATED : December 2, 2003
INVENTOR(S) : Koichiro Yamada et al.

It is certified that error appears in the above-identified patent and that said Letters Patent is hereby corrected as shown below:

Column 76,
Lines 51-60, in the structure for formula (I):

should read 

Column 79,
Line 5, after the structure 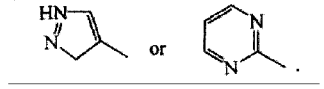 delete the period.

Column 81,
Line 47, before "a group", insert -- or --.

Column 83,
Lines 43-47, 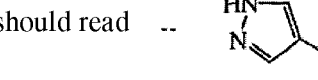 should read 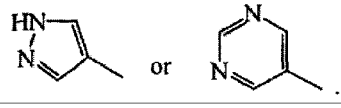

Column 84,
Lines 24-26, "(S)-2-(2-hydroxymethyl-1-pyrrolidinyl)-4-(3-chloro-4-methoxybenzylamino)-5-[N-(2-pyrimidinylmethyl)carbamoyl]pyrimidime;" should read -- (S)-2-(2-hydroxymethyl-1-pyrrolidinyl)-4-(3-chloro-4-methoxybenzylamino)-5-[N-(2-pyrimidinylmethyl)carbamoyl]pyrimidine; --.
Lines 40-42, "(S)-2-(2-hydroxymethyl-1-pyrrolidinyl)4-(chloro-4-methoxy-benzylamino)-5-[N-(2-morpholinoethyl)carbamoyl]pyrimidine;" should read -- (S)-2-(hydroxymethyl-1-pyrrolidinyl) (3-chloro-4-methoxybenzylamino)-5-[N-(2-morpholinoethyl)carbamoyl]pyrimidine; --.
Lines 43-45, "2-[(2S)-2-hydroxymethyl-1-pyrrolidinyl]-4-(3-chloro-4-methoxy-benzylamino)-5-[N-[[(2R)-4-methyl-2-morpholinyl]methyl]carbamoyl]pyrimidine;" should read -- 2-[(2S)-2-hydroxymethyl-1-pyrrolidinyl]-4-(3-chloro-4-methoxybenzylamino)-5-[N-[[(2R)-4-methyl-2-morpholinyl]methyl]carbamoyl] pyrimidine; --
Lines 46-48, "2-[(2S)-2-hydroxymethyl-1-pyrrolidinyl]-4-(3-chloro-4-methoxy-benzylamino)-5-[N-[[(2S)-4-methyl-2-morpholinyl]methyl]carbamoyl]pyrimidine;" should read -- 2-[(2S)-2-hydroxymethyl-1-pyrrolidinyl]-4-(3-chloro-4-methoxybenzylamino)-5-[N-[[(2S)-4-methyl-2-morpholinyl]methyl]carbamoyl] pyrimidine; --
Lines 49-51, "(S)-2-(2-hydroxymethyl-1-pyrrolidinyl)-4-(3-chloro-4-methoxy-benzylamino)-5-[N-pyrimidinylmethyl)carbamoyl]pyrimidine;" should read -- (S)-2-(2-hydroxymethyl-1-pyrrolidinyl)-4-(3-chloro-4-methoxybenzylamino)-5-[N-(pyrimidinylmethyl)carbamoyl]pyrimidine; --

UNITED STATES PATENT AND TRADEMARK OFFICE
CERTIFICATE OF CORRECTION

PATENT NO.    : 6,656,935 B2
DATED         : December 2, 2003
INVENTOR(S)   : Koichiro Yamada et al.

Page 2 of 3

It is certified that error appears in the above-identified patent and that said Letters Patent is hereby corrected as shown below:

Column 84 (cont'd),
Lines 52-54, "2-(4methyl-3-oxo-I-piperazinyl)-4-(3-chloro-4-methoxybenzyl-amino)-5-[N-(trans-4-hydroxycyclohexyl)carbamoyl]pyrimidine;" should read -- 2-(4methyl-3-oxo-1-piperazinyl)-4-(3-chloro-4-methoxybenzyl-amino)-5-[N-(trans-4-hydroxycyclohexyl)carbamoyl]pyrimidine; --
Line 64, replace the comma "," with a semicolon -- ; --.
Lines 65-67, "2-(5,6,7,8-tetrahydroimidazo[1,2-a]pyrazin-7-yl)-4-(3-chloro-4-methoxy-benzylamino)-5-[N-(2-pyrimidinylmethyl)carbamoyl]pyrimidine;" should read -- 2-(5,6,7,8-tetrahydroimidazo[1,2-a]pyrazin-7-yl)-4-(3chloro-4-methoxybenzylamino)-5-[N-(2-pyrimidinylmethyl)carbamoyl]pyrimidine; --.

Column 85,
Lines 1-3, "2-(5,6,7,8-tetrahydroimidazo[1,2-a]pyrazin-7-yl)-4-(3-chloro-4-methoxy-benzylamino)-5-[N-2-morpholinoethyl)carbamoyl]pyrimidine;" should read -- 2-(5,6,7,8-tetrahydroimidazo[1,2-a]pyrazin-7-yl)-4-(3-chloro-4-methoxybenzylamino)-5-[N-2-morpholinoethyl)carbamoyl]pyrimidine; --.
Lines 13-15, "(S)-2-(2-hydroxymethyl-1-pyrrolidinyl)-4-(3-chloro-4-methoxybenzylamino)-5-[N-(5-pyridazinylmethyl)carbamoyl]pyrimidine;" should read -- (S)-2-(2-hydroxymethyl-1-pyrrolidinyl)-4-(3-chloro-4-methoxybenzylamino)-5-[N-(5-pyrimidinylmethyl)carbamoyl]pyrimidine; --
Lines 16-18, "(S)-2-(hydroxymethyl-1-pyrrolidinyl)-4-(3-chloro-4-methoxybenzylamino)-5-[N-(2-pyrimidinylmethyl)carbomoyl]pyrimidine;" should read -- (S)-2-(hydroxymethyl-1-pyrrolidinyl)-4-(3-chloro-4-methoxybenzylamino)-5-[N-(2-pyridylmethyl)carbomoyl]pyrimidine; --.
Lines 19-21, "(S)-2-(2-hydroxymethyl-1-pyrrolidinyl)-4-(3-chloro-4-methoxybenzylamino)-5-[N-(2-morpholinoethyl)carbamoyl]pyrimidine;" should read -- (S)-2-(2-hydroxymethyl-1-pyrrolidinyl)-4-(3-chloro-4-methoxybenzylamino)-5-[(2-morpholinoethyl)carbonyl]pyrimidine; --.
Lines 22-24, "2-(5,6,7,8-tetrahydroimidazo[1,2-a]pyrazin-7-yl)-4-(3-chloro-4-methoxy-benzylamino)-5-[N-[(4-methyl-2-morpholiny)methyl]pyrimidine;" should read -- 2-(5,6,7,8-tetrahydroimidazo[1,2-a]pyrazin-7-yl)-4-(3-chloro-4-methoxybenzylamino)-5-[N-[(4-methyl-2-morpholiny)methyl]pyrimidine; --
Lines 38-40, "(S)-2-(2-hydroxymethyl-1-pyrrolidinyl)-4-(3-chloro-4-methoxybenzylamino) 5-[N-(4-pyrimidinylmethyl)carbamoyl]pyrimidine;" should read -- (S)-2-(2-hydroxymethyl-1-pyrrolidinyl)-4-(3-chloro-4-methoxybenzylamino)-5-[N-(4-pyrimidinylmethyl)carbamoyl]pyrimidine; --.
Lines 48-50, "2-(5,6,7,8-tetrahydroimidazo[1,2-a]pyrazin-7-yl)-4-(3-chloro-4-methoxy-benzylamino)-5-[N-(2-pyrimidinylmethyl)carbamoyl]pyrimidine;" should read -- 2-(5,6,7,8-tetrahydroimidazo[1,2-a]pyrazin-7-yl)-4-(3-chloro-4-methoxybenzylamino)-5-[N-(2-pyrimidinylmethyl)carbamoyl]pyrimidine; --.

UNITED STATES PATENT AND TRADEMARK OFFICE
CERTIFICATE OF CORRECTION

PATENT NO. : 6,656,935 B2
DATED : December 2, 2003
INVENTOR(S) : Koichiro Yamada et al.

It is certified that error appears in the above-identified patent and that said Letters Patent is hereby corrected as shown below:

Column 85 (cont'd),
Lines 51-53, "2-(5,6,7,8-tetrahydroimidazo[1-2-a]pyrazine-7-yl)-4-(3-chloro-4-methoxy-benzylamino)-5-[N-(2-morpholinoethyl)carbamoyl]pyridine;" should read -- 2-(5,6,7,8-tetrahydroimidazo[1-2-a]pyrazine-7-yl)-4-(3-chloro-4-methoxybenzylamino)-5-[N-(2-morpholinoethyl)carbamoyl]pyridine; --.
Lines 54-56, "2-(5,6,7,8-tetrahydro-1,7-naphthyridin-7-yl)-4-(3-chloro-4-methoxybenzylamino)5-[N-(2-morpholinoethyl)carbamoyl]pyrimidine;" should read -- 2-(5,6,7,8-tetrahydro-1,7-naphthyridin-7-yl)-4-(3-chloro-4-methoxybenzylamino)-5-[N-(2-morpholinoethyl)carbamoyl]pyrimidine; --.
Lines 57-59, "(S)-2-(2-hydroxymethyl-1-pyrrolidinyl)-4-(3-chloro-4-methoxybenzylamino)-5-[N-pyridinylmethyl)carbamoyl]pyrimidine;" should read -- (S)-2-(2-hydroxymethyl-1-pyrrolidinyl)-4-(3-chloro-4-methoxybenzylamino)-5-[N-(5-pyridinylmethyl)carbamoyl]pyrimidine; --.

Column 86,
Lines 1-3, "(S)-2-(2-hydroxymethyl-1-pyrrolidinyl)-4-(3-chloro-4-methoxy-benzylamino)-5-[N-(1,3,5-trimethyl-4-pyrazolyl)carbamoyl]pyrimidine;" should read -- (S)-2-(2-hydroxymethyl-1-pyrrolidinyl)-4-(3-chloro-4-methoxybenzylamino)-5-[N-(1,3,5-trimethyl-4-pyrazolyl)carbamoyl]pyrimidine, --.
Lines 19-21, "(S)-2-(2-hydroxymethyl-1-pyrrolidinyl)-4-(3-chloro-4-methoxybenzylamino)-5[N-(5-pyrimidinylmethyl)carbamoyl]pyrimidine;" should read -- (S)-2-(2-hydroxymethyl-1-pyrrolidinyl)-4-(3-chloro-4-methoxybenzylamino)-5-[N-(5-pyrimidinylmethyl)carbamoyl]pyrimidine; --.

This certificate supersedes Certificate of Correction issued September 28, 2004.

Signed and Sealed this

Thirtieth Day of November, 2004

JON W. DUDAS
*Director of the United States Patent and Trademark Office*

UNITED STATES PATENT AND TRADEMARK OFFICE
CERTIFICATE OF CORRECTION

PATENT NO.   : 6,656,935 B2
DATED        : December 2, 2003
INVENTOR(S)  : Koichiro Yamada et al.

It is certified that error appears in the above-identified patent and that said Letters Patent is hereby corrected as shown below:

Column 76,
Lines 51-60, in the structure for formula (I):

Column 79,
Line 5, after the structure  delete the period.

Column 81,
Line 47, before "a group", insert -- or --.

Column 83,
Lines 43-47, 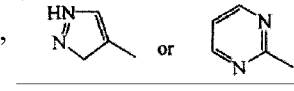 should read 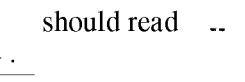

Column 84,
Lines 24-26, "(S)-2-(2-hydroxymethyl-1-pyrrolidinyl)-4-(3-chloro-4-methoxybenzylamino)-5-[N-(2-pyrimidinylmethyl)carbamoyl]pyrimidime;" should read -- (S)-2-(2-hydroxymethyl-1-pyrrolidinyl)-4-(3-chloro-4-methoxybenzylamino)-5-[N-(2-pyrimidinylmethyl)carbamoyl]pyrimidine; --.
Lines 40-42, "(S)-2-(2-hydroxymethyl-1-pyrrolidinyl)4-(chloro-4-methoxy-benzylamino)-5-[N-(2-morpholinoethyl)carbamoyl]pyrimidine;" should read -- (S)-2-(hydroxymethyl-1-pyrrolidinyl)-4-(3-chloro-4-methoxybenzylamino)-5-[N-(2-morpholinoethyl)carbamoyl]pyrimidine; --.
Lines 43-45, "2-[(2S)-2-hydroxymethyl-1-pyrrolidinyl]-4-(3-chloro-4-methoxy-benzylamino)-5-[N-[[(2R)-4-methyl-2-morpholinyl]methyl]carbamoyl]pyrimidine;" should read -- 2-[(2S)-2-hydroxymethyl-1-pyrrolidinyl]-4-(3-chloro-4-methoxybenzylamino)-5-[N-[[(2R)-4-methyl-2-morpholinyl]methyl]carbamoyl]pyrimidine; --
Lines 46-48, "2-[(2S)-2-hydroxymethyl-1-pyrrolidinyl]-4-(3-chloro-4-methoxy-benzylamino)-5-[N-[[(2S)-4-methyl-2-morpholinyl]methyl]carbamoyl]pyrimidine;" should read -- 2-[(2S)-2-hydroxymethyl-1-pyrrolidinyl]-4-(3-chloro-4-methoxymethoxybenzylamino)-5-[N-[[(2S)-4-methyl-2-morpholinyl]methyl]carbamoyl]pyrimidine; --
Lines 49-51, "(S)-2-(2-hydroxymethyl-1-pyrrolidinyl)-4-(3-chloro-4-methoxy-benzylamino)-5-[N-pyrimidinylmethyl)carbamoyl]pyrimidine;" should read -- (S)-2-(2-hydroxymethyl-1-pyrrolidinyl)-4-(3-chloro-4-methoxybenzylamino)-5-[N-(pyrimidinylmethyl)carbamoyl]pyrimidine; --

UNITED STATES PATENT AND TRADEMARK OFFICE
CERTIFICATE OF CORRECTION

PATENT NO. : 6,656,935 B2
DATED : December 2, 2003
INVENTOR(S) : Koichiro Yamada et al.

It is certified that error appears in the above-identified patent and that said Letters Patent is hereby corrected as shown below:

Column 84 (cont'd),
Lines 52-54, "2-(4methyl-3-oxo-I-piperazinyl)-4-(3-chloro-4-methoxybenzyl-amino)-5-[N-(trans-4-hydroxycyclohexyl)carbamoyl]pyrimidine;" should read -- 2-(4methyl-3-oxo-1-piperazinyl)-4-(3-chloro-4-methoxybenzyl-amino)-5-[N-(trans-4-hydroxycyclohexyl) carbamoyl]pyrimidine; --
Line 64, replace the comma "," with a semicolon -- ; --.
Lines 65-67, "2-(5,6,7,8-tetrahydroimidazo[1,2-a]pyrazin-7-yl)-4-(3-chloro-4-methoxy-benzylamino)-5-[N-(2-pyrimidinylmethyl)carbamoyl]pyrimidine;" should read -- 2-(5,6,7,8-tetrahydroimidazo[1,2-a]pyrazin-7-yl)-4-(3chloro-4-methoxybenzylamino)-5-[N-(2-pyrimidinylmethyl)carbamoyl]pyrimidine; --.

Column 85,
Lines 1-3, "2-(5,6,7,8-tetrahydroimidazo[1,2-a]pyrazin-7-yl)-4-(3-chloro-4-methoxy-benzylamino)-5-[N-2-morpholinoethyl)carbamoyl]pyrimidine;" should read -- 2-(5,6,7,8-tetrahydroimidazo[1,2-a]pyrazin-7-yl)-4-(3-chloro-4-methoxybenzylamino)-5-[N-2-morpholinoethyl)carbamoyl]pyrimidine; --.
Lines 13-15, "(S)-2-(2-hydroxymethyl-1-pyrrolidinyl)-4-(3-chloro-4-methoxybenzylamino)-5-[N-(5-pyridazinylmethyl)carbamoyl]pyrimidine;" should read -- (S)-2-(2-hydroxymethyl-1-pyrrolidinyl)-4-(3-chloro-4-methoxybenzylamino)-5-[N-(5-pyrimidinylmethyl)carbamoyl]pyrimidine; --
Lines 16-18, "(S)-2-(hydroxymethyl-1-pyrrolidinyl)-4-(3-chloro-4-methoxybenzylamino)-5-[N-(2-pyrimidinylmethyl)carbomoyl]pyrimidine;" should read -- (S)-2-(hydroxymethyl-1-pyrrolidinyl)-4-(3-chloro-4-methoxybenzylamino)-5-[N-(2-pyridylmethyl)carbomoyl]pyrimidine; --.
Lines 19-21, "(S)-2-(2-hydroxymethyl-1-pyrrolidinyl)-4-(3-chloro-4-methoxybenzylamino)-5-[N-(2-morpholinoethyl)carbamoyl]pyrimidine;" should read -- (S)-2-(2-hydroxymethyl-1-pyrrolidinyl)-4-(3-chloro-4-methoxybenzylamino)-5-[(2-morpholinoethyl)carbonyl]pyrimidine; --.
Lines 22-24, "2-(5,6,7,8-tetrahydroimidazo[1,2-a]pyrazin-7-yl)-4-(3-chloro-4-methoxy-benzylamino)-5-[N-[(4-methyl-2-morpholiny)methyl]pyrimidine;" should read -- 2-(5,6,7,8-tetrahydroimidazo[1,2-a]pyrazin-7-yl)-4-(3-chloro-4-methoxybenzylamino)-5-[N-[(4-methyl-2-morpholiny)methyl]pyrimidine; --
Lines 38-40, "(S)-2-(2-hydroxymethyl-1-pyrrolidinyl)-4-(3-chloro-4-methoxybenzylamino) 5-[N-(4-pyrimidinylmethyl)carbamoyl]pyrimidine;" should read -- (S)-2-(2-hydroxymethyl-1-pyrrolidinyl)-4-(3-chloro-4-methoxybenzylamino)-5-[N-(4-pyrimidinylmethyl)carbamoyl]pyrimidine; --.
Lines 48-50, "2-(5,6,7,8-tetrahydroimidazo[1,2-a]pyrazin-7-yl)-4-(3-chloro-4-methoxy-benzylamino)-5-[N-(2-pyrimidinylmethyl)carbamoyl]pyrimidine;" should read -- 2-(5,6,7,8-tetrahydroimidazo[1,2-a]pyrazin-7-yl)-4-(3-chloro-4-methoxybenzylamino)-5-[N-(2-pyrimidinylmethyl)carbamoyl]pyrimidine; --.

UNITED STATES PATENT AND TRADEMARK OFFICE
CERTIFICATE OF CORRECTION

PATENT NO. : 6,656,935 B2
DATED : December 2, 2003
INVENTOR(S) : Koichiro Yamada et al.

It is certified that error appears in the above-identified patent and that said Letters Patent is hereby corrected as shown below:

Column 85 (cont'd),
Lines 51-53, "2-(5,6,7,8-tetrahydroimidazo[1-2-a]pyrazine-7-yl)-4-(3-chloro-4-methoxy-benzylamino)-5-[N-(2-morpholinoethyl)carbamoyl]pyridine;" should read -- 2-(5,6,7,8-tetrahydroimidazo[1-2-a]pyrazine-7-yl)-4-(3-chloro-4-methoxybenzylamino)-5-[N-(2-morpholinoethyl)carbamoyl]pyridine; --.
Lines 54-56, "2-(5,6,7,8-tetrahydro-1,7-naphthyridin-7-yl)-4-(3-chloro-4-methoxybenzylamino)5-[N-(2-morpholinoethyl)carbamoyl]pyrimidine;" should read -- 2-(5,6,7,8-tetrahydro-1,7-naphthyridin-7-yl)-4-(3-chloro-4-methoxybenzylamino)-5-[N-(2-morpholinoethyl)carbamoyl]pyrimidine; --.
Lines 57-59, "(S)-2-(2-hydroxymethyl-1-pyrrolidinyl)-4-(3-chloro-4-methoxybenzylamino)-5-[N-pyridinylmethyl)carbamoyl]pyrimidine;" should read -- (S)-2-(2-hydroxymethyl-1-pyrrolidinyl)-4-(3-chloro-4-methoxybenzylamino)-5-[N-(5-pyridinylmethyl)carbamoyl]pyrimidine; --.

Column 86,
Lines 1-3, "(S)-2-(2-hydroxymethyl-1-pyrrolidinyl)-4-(3-chloro-4-methoxy-benzylamino)-5-[N-(1,3,5-trimethyl-4-pyrazolyl)carbamoyl]pyrimidine;" should read -- (S)-2-(2-hydroxymethyl-1-pyrrolidinyl)-4-(3-chloro-4-methoxybenzylamino)-5-[N-(1,3,5-trimethyl-4-pyrazolyl)carbamoyl]pyrimidine, --.
Lines 19-21, "(S)-2-(2-hydroxymethyl-1-pyrrolidinyl)-4-(3-chloro-4-methoxybenzylamino)-5[N-(5-pyrimidinylmethyl)carbamoyl]pyrimidine;" should read -- (S)-2-(2-hydroxymethyl-1-pyrrolidinyl)-4-(3-chloro-4-methoxybenzylamino)-5-[N-(5-pyrimidinylmethyl)carbamoyl]pyrimidine; --.

This certificate supersedes Certificate of Correction issued September 28, 2004 and November 30, 2004.

Signed and Sealed this

Third Day of May, 2005

JON W. DUDAS
*Director of the United States Patent and Trademark Office*